(12) United States Patent
Dukes et al.

(10) Patent No.: US 9,499,677 B2
(45) Date of Patent: Nov. 22, 2016

(54) BLACK CERAMIC ADDITIVES, PIGMENTS, AND FORMULATIONS

(71) Applicant: Melior Innovations, Inc., Houston, TX (US)

(72) Inventors: Douglas M. Dukes, Troy, NY (US); Ashish P. Diwanji, New Albany, OH (US); Michael J. Mueller, Katy, TX (US); Michael Molnar, Summerfield, NC (US); Walter J. Sherwood, Glenville, NY (US); Andrew R. Hopkins, Sylvania, OH (US); Mark S. Land, Houston, TX (US); Brian L. Benac, Hadley, NY (US)

(73) Assignee: Melior Innovations, Inc., Houston, TX (US)

( * ) Notice: Subject to any disclaimer, the term of this patent is extended or adjusted under 35 U.S.C. 154(b) by 0 days.

(21) Appl. No.: 14/634,828

(22) Filed: Feb. 28, 2015

(65) Prior Publication Data

US 2015/0252166 A1     Sep. 10, 2015

Related U.S. Application Data

(63) Continuation-in-part of application No. 14/268,150, filed on May 2, 2014.

(60) Provisional application No. 61/946,598, filed on Feb. 28, 2014, provisional application No. 62/106,094, filed on Jan. 21, 2015, provisional application No. 61/818,906, filed on May 2, 2013, provisional application No. 61/818,981, filed on May 3, 2013.

(51) Int. Cl.
| | |
|---|---|
| C09D 133/14 | (2006.01) |
| C08K 3/00 | (2006.01) |
| C08K 3/34 | (2006.01) |
| C09D 7/12 | (2006.01) |
| C09D 163/00 | (2006.01) |
| C09D 101/28 | (2006.01) |
| C09D 101/18 | (2006.01) |
| C09D 105/00 | (2006.01) |
| C09D 11/00 | (2014.01) |
| A61K 8/25 | (2006.01) |
| A61Q 3/02 | (2006.01) |
| C08G 77/20 | (2006.01) |
| C08G 77/50 | (2006.01) |
| C08L 83/04 | (2006.01) |
| C01B 33/113 | (2006.01) |
| C08G 77/12 | (2006.01) |

(52) U.S. Cl.
CPC ............... *C08K 3/0033* (2013.01); *A61K 8/25* (2013.01); *A61Q 3/02* (2013.01); *C08G 77/20* (2013.01); *C08G 77/50* (2013.01); *C08K 3/34* (2013.01); *C08L 83/04* (2013.01); *C09D 7/1216* (2013.01); *C09D 11/00* (2013.01); *C09D 101/18* (2013.01); *C09D 101/28* (2013.01); *C09D 105/00* (2013.01); *C09D 133/14* (2013.01); *C09D 163/00* (2013.01); *C01B 33/113* (2013.01); *C08G 77/12* (2013.01)

(58) Field of Classification Search
CPC ...... C01B 33/113; C08K 3/0033; C08K 3/34; C09D 7/1216
See application file for complete search history.

(56) References Cited

U.S. PATENT DOCUMENTS

| | | | |
|---|---|---|---|
| 3,409,868 A | 11/1968 | Salathiel | |
| 3,520,656 A | 7/1970 | Meadows | |
| 4,208,471 A | 6/1980 | Bresak | |
| 4,298,063 A | 11/1981 | Regalbuto | |
| 4,433,069 A | 2/1984 | Harper | |
| 4,516,608 A | 5/1985 | Titus | |
| 4,546,163 A | 10/1985 | Haluska | |
| 4,547,468 A | 10/1985 | Jones | |
| 4,711,928 A | 12/1987 | Lee | |
| 4,833,220 A * | 5/1989 | Frey | C04B 35/571 525/475 |
| 4,840,781 A | 6/1989 | Noake | |
| 5,162,480 A | 11/1992 | Schilling | |

(Continued)

FOREIGN PATENT DOCUMENTS

| | | |
|---|---|---|
| EP | 0490401 | 6/1992 |
| EP | 0560485 | 4/2013 |

(Continued)

OTHER PUBLICATIONS

International Search Report and the Written Opinion of the International Searching Authority, PCT/US2015/018211, mailed May 27, 2015.

(Continued)

*Primary Examiner* — Margaret Moore
(74) *Attorney, Agent, or Firm* — Glen P. Belvis; Steptoe & Johnson LLP

(57) ABSTRACT

Ceramic black materials for use as, or in, colorants, inks, pigments, dyes, additives and formulations utilizing these black materials. Black ceramics having silicon, oxygen and carbon, and methods of making these ceramics; formulations utilizing these black ceramics; and devices, structures and apparatus that have or utilize these formulations. Plastics, paints, inks, coatings, formulations, liquids and adhesives containing ceramic black materials, preferably polymer derived black ceramic materials, and in particular polysilocarb polymer derived ceramic materials. The particular polysilocarb ceramics materials found in the claimed coatings and materials contain a specific amount of C, Si and O, as well as a specific amount of free and Si bonded carbon.

52 Claims, 11 Drawing Sheets

(56) References Cited

U.S. PATENT DOCUMENTS

| | | | |
|---|---|---|---|
| 5,180,694 A | 1/1993 | Renlund | |
| 5,188,175 A | 2/1993 | Sweet | |
| 5,225,123 A | 7/1993 | Torobin | |
| 5,225,283 A | 7/1993 | Leung | |
| 5,275,980 A | 1/1994 | Schilling, Jr. | |
| 5,328,976 A | 7/1994 | Leung | |
| 5,354,602 A | 10/1994 | Stranford | |
| 5,354,830 A | 10/1994 | Williams | |
| 5,356,471 A * | 10/1994 | Reynders | A61Q 1/02 106/415 |
| 5,358,674 A | 10/1994 | Rabe | |
| 5,376,595 A | 12/1994 | Zupancic | |
| 5,436,207 A | 7/1995 | Atwell | |
| 5,438,025 A | 8/1995 | Leung | |
| 5,552,466 A | 9/1996 | Beckley | |
| 5,588,491 A | 12/1996 | Brugman | |
| 5,635,250 A | 6/1997 | Blum | |
| 5,698,340 A | 12/1997 | Xue | |
| 5,714,025 A | 2/1998 | Brungardt | |
| 5,872,070 A | 2/1999 | Dismukes | |
| 5,955,194 A | 9/1999 | Campbell | |
| 6,329,487 B1 | 12/2001 | Abel | |
| 6,348,554 B1 | 2/2002 | Roos | |
| 6,624,228 B1 | 9/2003 | Dismukes | |
| 6,635,215 B2 | 10/2003 | Sugimoto | |
| 7,026,392 B2 * | 4/2006 | Nakajima | C08F 290/06 523/160 |
| 7,090,027 B1 | 8/2006 | Williams | |
| 7,175,694 B2 | 2/2007 | Ma | |
| 7,287,573 B2 | 10/2007 | McNulty | |
| 7,789,147 B2 | 9/2010 | Brannon | |
| 7,942,302 B2 | 5/2011 | Roby | |
| 8,006,759 B1 | 8/2011 | Cochran | |
| 8,173,568 B2 | 5/2012 | Nishimura | |
| 2002/0198353 A1 | 12/2002 | Chen | |
| 2003/0102071 A1 | 6/2003 | Mako | |
| 2003/0150614 A1 | 8/2003 | Brown | |
| 2004/0009865 A1 | 1/2004 | Nair | |
| 2004/0074648 A1 | 4/2004 | Legras | |
| 2005/0028979 A1 | 2/2005 | Brannon | |
| 2005/0244641 A1 | 11/2005 | Vincent | |
| 2006/0042171 A1 | 3/2006 | Radtke | |
| 2006/0046920 A1 | 3/2006 | Odaka | |
| 2006/0069176 A1 | 3/2006 | Bowman | |
| 2006/0177661 A1 | 8/2006 | Smith | |
| 2007/0022913 A1 | 2/2007 | Wang | |
| 2007/0099790 A1 | 5/2007 | Wan | |
| 2008/0095942 A1 | 4/2008 | Sherwood | |
| 2008/0241383 A1 | 10/2008 | Yoshino | |
| 2009/0202732 A1 | 8/2009 | Kruger | |
| 2009/0206025 A1 | 8/2009 | Ichikawa | |
| 2009/0209405 A1 | 8/2009 | Fei | |
| 2010/0156215 A1 | 6/2010 | Goertzen | |
| 2010/0160104 A1 | 6/2010 | Dinter | |
| 2011/0008236 A1 | 1/2011 | Hinman | |
| 2011/0033708 A1 | 2/2011 | Harimoto | |
| 2011/0045963 A1 * | 2/2011 | Harimoto | B82Y 30/00 501/154 |
| 2011/0077176 A1 | 3/2011 | Smith | |
| 2011/0091722 A1 | 4/2011 | Koehne | |
| 2011/0160104 A1 | 6/2011 | Wu | |
| 2011/0247822 A1 | 10/2011 | Dams | |
| 2012/0121981 A1 | 5/2012 | Harimoto | |
| 2012/0160520 A1 | 6/2012 | Lumbye | |
| 2012/0172475 A1 | 7/2012 | Meador | |
| 2013/0122763 A1 | 5/2013 | Fish | |
| 2013/0319677 A1 | 12/2013 | Hallundbaek | |
| 2014/0110110 A1 | 4/2014 | Rohring | |
| 2014/0264984 A1 | 9/2014 | Kosvintsev | |
| 2014/0274658 A1 | 9/2014 | Sherwood | |
| 2014/0308585 A1 | 10/2014 | Han | |
| 2014/0318799 A1 | 10/2014 | Moeller | |
| 2014/0323364 A1 | 10/2014 | Sherwood | |
| 2014/0326453 A1 | 11/2014 | Moeller | |
| 2014/0343220 A1 | 11/2014 | Sherwood | |
| 2015/0027306 A1 | 1/2015 | Tan | |
| 2015/0175750 A1 | 6/2015 | Hopkins | |
| 2015/0252166 A1 | 9/2015 | Dukes | |
| 2015/0252170 A1 | 9/2015 | Diwanji | |
| 2015/0252171 A1 | 9/2015 | Molnar | |
| 2016/0046529 A1 | 2/2016 | Bricco | |
| 2016/0102528 A1 | 4/2016 | Wise | |
| 2016/0152889 A1 | 6/2016 | Hopkins | |
| 2016/0207780 A1 | 7/2016 | Dukes | |
| 2016/0207781 A1 | 7/2016 | Dukes | |
| 2016/0207782 A1 | 7/2016 | Diwanji | |
| 2016/0207783 A1 | 7/2016 | Hopkins | |
| 2016/0207836 A1 | 7/2016 | Land | |
| 2016/0208412 A1 | 7/2016 | Sandgren | |

FOREIGN PATENT DOCUMENTS

| | | |
|---|---|---|
| WO | WO2013059793 | 4/2013 |
| WO | WO2016118704 | 7/2016 |

OTHER PUBLICATIONS

International Search Report and the Written Opinion of the International Searching Authority, PCT/US2015/021861, mailed Sep. 16, 2015.

International Search Report and the Written Opinion of the International Searching Authority, PCT/US2015/051997, mailed Mar. 3, 2016.

International Search Report and the Written Opinion of the International Searching Authority, PCT/US2016/014245, mailed Mar. 24, 2016.

International Search Report and Written Opinion of the International Searching Authority, PCT/US2012/061329, mailed Jan. 8, 2013.

International Search Report and Written Opinion of the International Searching Authority, PCT/US2014/045500, mailed Nov. 3, 2014.

International Search Report and Written Opinion of the International Searching Authority, PCT/US14/045497, mailed Nov. 4, 2014.

International Search Report and Written Opinion of the International Searching Authority, PCT/US14/045494, mailed Nov. 4, 2014.

International Search Report and Written Opinion of the International Searching Authority, PCT/US14/36522, mailed Nov. 5, 2014.

International Search Report and Written Opinion of the International Searching Authority, PCT/US14/060500, mailed Feb. 24, 2015.

International Search Report and Written Opinion of the International Searching Authority, PCT/US15/018210, mailed May 20, 2015.

International Search Report and Written Opinion of the International Searching Authority, PCT/US15/018211, mailed May 27, 2015.

EEMS, CSO 110 HT Product Data Sheet, Polycarbosiloxane liquid polymer for high temperature ceramic applications, Feb. 2010, 2 pp.

EEMS, CSO 111 HT Product Data Sheet, Stabilized polycarbosiloxane liquid polymer for high temperature ceramic applications, May 2010, 3 pp.

EEMS, CSO 121 Product Data Sheet, Polycarbosiloxane liquid polymer for fire-resistant non-ceramic applications and high temperature ceramic applications, Mar. 2010, 3 pp.

EEMS, CSO 300, 305, 310, 320 Products Data Sheet, Polycarbosiloxane liquid polymers, Jul. 10, 2010, 3 pp.

EEMS, CSO 315 Product Data Sheet, Polycarbosiloxane liquid polymer for pre-preg molding and wet lay-up processing of fiber reinforced composites, Sep. 2011, 1 pp.

EEMS, 500 Series Product Data Sheet, Liquid polymers for very high temperature ceramic applications, Jun. 2012, 3 pp.

EEMS, CSO 110 HT Material Safety Data Sheet, Feb. 26, 2010, 4 pp.

(56) References Cited

OTHER PUBLICATIONS

EEMS, CSO 121 HT Material Safety Data Sheet, Jun. 7, 2011, 4 pp.
EEMS, CSO 131 & 130 Material Safety Data Sheet, Jun. 27, 2012, 4 pp.
EEMS, CSO 230 Material Safety Data Sheet, Jun. 5, 2011, 4 pp.
EEMS, CSO 310 Material Safety Data Sheet, Jun. 7, 2010, 4 pp.
EEMS, CSO 350 Material Safety Data Sheet, Jun. 7, 2010, 4 pp.
EEMS, CSO 120 Product Data Sheet, Low-cost polycarbosiloxane liquid polymer for 2200° F. temperature stable ceramic applications, Sep. 2011, 1 pp.
EEMS, CSO 120 HT Material Safety Data Sheet, Jun. 7, 2011, 4 pp.
EEMS, CSO 230 HT Product Data Sheet, Polycarbosiloxane liquid polymer for high temperature ceramic applications, Mar. 2012, 3 pp.
EEMS, CSO 315 HT Material Safety Data Sheet, Jun. 7, 2010, 4 pp.
Applicant, Information disclosure statement of commercial activity, Jun. 28, 2016, 6 pp.
Ganesan, G., Raghukandan, K., Karthikeyan, R., Pai, B.C., Development of processing maps for 6061 Al/15% SiCp Composite Material, Materials Science and Engineering A369 (2004) 230-235, 6 pp., © 2003 Elsevier B.V.
Gao, P-C, Simon, P., Favier, F., Silicon carbide with tunable ordered mesoporosity, Microporous and Mesoporous Materials, 180 (2013) 172-177, 6 pp., journal homepage: www.elsevier.com/locate/micromeso; © 2013 Elsevier Inc.
Goela, J.S., CVD growth and characterization of [B]-SiC for IR windows, Morton Advanced Materials, 1998, 17 pp., 185 New Boston St., Woburn, MA 01801.
Goela, J.S., Taylor, R.L., Transparent SiC for mid-IR windows and domes, SPIE vol. 2286, 14 pp., Morton Advanced Materials, 185 New Boston Street, Woburn, MA 01801.
Greil, P., Advanced materials progress report on advanced engineering ceramics, Advanced Materials, Adv. Mater. 2002.14, No. 10, May 17, 8 pp., Wiley-VCH Verlag GmbH. D-69469 Weinhcim, 2002 0935-9648/02/1005-0716. © Wiley-VCH Verlag GmbH, D-69469 Weinheim, 2002.
Gumula, T., Paluszkiewicz, C., Blazewicz, S., Study on Thermal Decomposition Processes of Polysiloxane Polymers—From Polymer to Nanosized Silicon Carbide, Journal of Analytical and Applied Pyrolysis, J. Anal. Appl. Pyrolysis 86 (2009) 375-380, 6 pp., journal homepage: www.elsevier.com/locate/jaap. © 2009 Elsevier B.V.
Hamilton, H., Palladium-based membranes for , hydrogen separation, Platinum Metals Rev., 2012, 56, (2), 117-123, 7 pp., http://dx.doi.org/10.1595/147106712X632460 , © 2012 Johnson Matthey.
Handke, M., Kowalewska, A., Siloxane and silsesquioxane molecules—precursors for silicate materials, Spectrochimica Acta Part A: Molecular and Biomolecular Spectroscopy , vol. 79, Issue 4, Aug. 15, 2011, pp. 749-757., 9 pp.
Harrison, S., Marcus., H.L., Structural analysis of silicon carbide deposited by gas-phase selective area laser deposition (SALD), Institute of Materials Science, 97 North Eagleville Road , Storrs, CT 06269..3136 , (860) 486..4623 , Fax: (860) 486..4745, 471:478, 8 pp.
Hashim, J., Looney, L., Hashmi, M.S.J., The enhancement of wettability of sic particles in cast aluminum matrix composites, Journal of Materials Processing Technology 119 (2001) 329-335, 7 pp., © 2001 Elsevier Science B.V.
Hayashi, T., Hydrosilylation of carbon-carbon double bonds, Chapter 7, 15 pp., Department of Chemistry, Faculty of Science, Kyoto University, Sakyo, Kyoto 606-8502, Japan.
Hellmann, J.R., Scheetz, B.E., Final report: Evaluation of proppants derived from ion exchanged mixed glass cullet for use in gas-laden shale formations, Pennsylvania State University, 2012, Project #SWC 4312 for the period Oct. 1, 2009-May 31, 2012, Contract #DE-FE003616; subaward# 4312-TPSU-DOE-3616 , Submitted to the Stripper Well Consortium, Jun. 5, 2012 , 28 pp.
Henderson, D.A., Novel piezo motor enables positive displacement microfluidic pump, Presented at NSTI Nanotech 2007, 4 pp, (c) 2007 New Scale Technologies, Inc. I phone (585) 924-4450, www.newscaletech.com.

Holte, D., Flash vacuum pyrolysis, Baran Group Meeting, Apr. 21, 2012, 8 pp.
Howell, B.A., Alomari, M., Thermal degradation of poly(propylene oxide), 8 pp., Center for Applications in Polymer Science, Department of Chemistry, Central Michigan University , Mt. Pleasant, MI 48859-0001.
Hurwitz, F.I., Heimann, P.J., Kacik, T.A., Redistribution reactions in blackglass™ during pyrolysis and their effect on oxidative stability, Ceramic Engineering & science Proceedings, Editor John B. Wachtman, 8 pp., © 1995 The American Ceramic Society.
Hurwitz, F.I., Meador, M.A.B., Tailoring silicon oxycarbide glasses for oxidative stability, NASA Lewis Research Center, Cleveland, OH44135, 26 pp.
Hwang, Y., Riu, D-H, Kim, K-J, Chang, C-H, Porous SiOC Beads by freeze-drying polycarbosilane emulsions, Materials Letters, Mater Lett (2014), 4 pp., http://dxx.doi.org/10.1016/j.matlet.2014.05.194, © 2014 Published by Elsevier B.V.
Idesaki, A., Sugimoto, M., Yoshikawa, M., Synthesis of a porous SiC material from polycarbosilane by direct foaming and radiation curing, Innovating Processing and Manufacturing of Advanced Ceramics and Composites II, 61-69, 5 pp.
Jenšterle, J., Zornik, M., Presentation pre-development status of C. CAST brake disc material, 30 pp., MS Production, Slovenija.
Jeon, E., Kim, H., Yun, J., Preparation of silicon oxycarbide amorphous ceramics from polymer precursors and the characterization of their high temperature stability, Journal of Ceramic Processing Research, vol. 13, No. 3, pp. 239-242 (2012), 4 pp.
Johnson, J.S., Grobsky, K., Bray, D.J., Rapid fabrication of lightweight silicon carbide mirrors, Proc. SPIE vol. 4771, 2002, 11 pp., © 2002 SPIE.
Jüttke, Y., Richter, H., Voigt, I., Prasad, R.M., Bazarjani, M.S., Ghurlo, A., Riedel, R., Polymer derived ceramic membranes for gas separation, Chemical Engineering Transactions, vol. 32, 1891-1896, 2013,6 pp., A publication of The Italian Association of Chemical Engineering, Online at: www.aidic.it/cet , 2013, ISBN 978-88-95608-23-5; ISSN 1974-9791, © 2013, AIDIC Servizi S.r.l.
Kang, S-J. L., Park, J-H, Ko, S-Y, Lee, H-Y, Solid-State Conversion of Single Crystals: The Principle and the State-of-the-Art, Journal of the American Ceramic Society, vol. 98, No. 2, Feb. 2015, 13 pp., © 2015 The American Ceramic Society.
Kim, C.Y., Kim, S.H., Kim, H.S., Navamathavan, R., Choi, C.K., Formation mechanism and structural characteristics of low-dielectric-constant SiOC(-H) films deposited by using plasma-enhanced chemical-vapor deposition with DMDMS and O2 Precursors, Journal of the Korean Physical Society, vol. 50, No. 4, Apr. 2007, 1119-1124, 6 pp.
Kinowski, C., Bouazaoui, M., Bechara, R., Hench, L.L., Nedelec, J.M., Turrell, S., Kinetics of densification of porous silica gels: a structural and textural study, Journal of Non-Crystalline Solids, 291 (2001) 143-152, 10 pp., © 2001 Elsevier Science B.V.
Kleebe, H-J., Turquat, C., Phase Separation in an SiCO Glass Studied by Transmission Electron Microscopy and Electron Energy-loss Spectroscopy, Journal of the American Ceramic Society, vol. 84, No. 5, 2001, 1073-1080, 8 pp.
Kullman, J., The Complicated World of Proppant Selection, Power Point, South Dakota School of Mines & Technology, Oct. 2011, 65 pp.
Laine, R.M., Babonneau, F., Preceramic Polymer Routes to Silicon Carbide, Reviews, Chem. Mater. 1993, 5, 260-279, 20 pp.
Laine, R.M., Sellinger, A., Si-containing ceramic precursors, Chapter 39, The Chemistry of Organic Silicon Compounds, vol. 2, 2245-2316, 72 pp., © 1998 John Wiley & Sons, Ltd, ISBN: 0-471-96757-2.
Launer, P.J., Infrared Analysis of Organosilicon Compounds: Spectra-Structure Correlations, Laboratory for Materials, Inc., Burnt Hills, New York 12027, 100-103, 4 pp., Reprinted from Silicon Compounds Register and Review, Edited by B., Arkles, et al, 1987, Petrarch Systems.
Lee, R., Carbosilanes: Reactions & Mechanisms of SMP-10 Pre-Ceramic Polymers, Marshall Space Flight Center, Jacobs ESTS Group / ICRC, Jul. 2009, 23 pp.
Leslie, C.J., Kim H.J., Chen, H., Walker, K.M., Boakye, E.E., Chen, C. Carney, C.M., Cinibulk, M.K., Chen, M.-Y., Polymer-Derived

(56) References Cited

OTHER PUBLICATIONS

Ceramics for Development of Ultra-High Temperature Composites, Innovative Processing and Manufacturing of Advanced Ceramics and Composites II, 33-45, 7 pp.

Lewis, L.N., Stein, J., Gao, Y., Colborn, R.E., Hutchins, G., Platinum catalysts used in the silicones industry their synthesis and activity in hydrosilylation, Platinum Metals Rev., 1997, 41, (2), 66-75, 10 pp.

Li, Y., Wu, D., Chang, L., Shi, Y., Wu, D., Fang, Z., A Model for the Bulk Crushing Strength of Spherical Catalysts, Ind. Eng. Chem. Res. 1999, 38, 1911-1916, 6 pp.

Liang T., Li, Y-L., Su, D., Du, H.-B., Silicon oxycarbide ceramics with reduced carbon by pyrolysis of polysiloxanes in water vapor, Journal of the European Ceramic Society 30 (2010) 2677-2682, 6 pp.

Linck, C., Ionescu, E., Papendorf, B., Galuskova, D., Galusek, D., Sajgalík, P., Riedel R., Corrosion behavior of silicon oxycarbide-based ceramic nanocomposites under hydrothermal conditions, Int. J. Mat. Res. (formerly Z. Metallkd.) 103 (2012) 1, 31-39, 9 pp., International Journal of Materials Research downloaded from www.hanser-elibrary.com by Mr. Mark Land on Jan. 3, 2014 for personal use only.

Linsmeier, K. D., Technical Ceramics, The material of choice for the most demanding applications, CeramTec GmbH, 73207 Plochingen, www.ceramtec.com, Verlag Moderne Industrie, 2011, 85 pp., All rights reserved with Süddeutscher Verlag onpact GmbH, 81677 Munich, www.sv-onpact.de.

Liu, P. KT, Development of Hydrogen Selective Membranes/Modules as Reactors/Separators for Distributed Hydrogen Production, DE-FG36-05GO15092, May 18-22, 2009, 23 pp., Media and Process Technology Inc., Pittsburgh, PA 15238.

Liu, C-Y., Liao, N-B., Yang, Y., Zhang, J-L, Effect of Sputtering Power on Nano-mechanical Properties of SiCO Film, International Conference on Material Science and Application (ICMSA 2015), 1037-1041, 5 pp.

Liu, X., Li, Y-L., Hou, F., Fabrication of SiOC Ceramic Microparts and Patterned Structures from Polysiloxanes via Liquid Cast and Pyrolysis, J. Am. Ceram. Soc., 92 [1] 49-53 (2009), 5 pp., DOI: 10.1111/j.1551-2916.2008.02849.x, © 2008 The American Ceramic Society.

Liu, C., Chen, H.Z., Komarneni, S., Pantano, C.G., High Surface Area SiC/Silicon Oxycarbide Glasses Prepared from Phenyltrimethoxysilane-Tetramethoxysilane Gels, Journal of Porous Materials 2, 245-252 (1996), 8 pp., 1996 Kluwer Academic Publishers. Manufactured in The Netherlands.

Louette, P., Bodino, F., Pireaux, J-J., Poly (methyl hydrogen siloxane) (PMHS) XPS Reference Core Level and Energy Loss Spectra, Surface Science Spectra, vol. 12, 2005, 1055-5269/2005/12/133/6 © 2006 American Vacuum Society 133.

Lu., B., Zhang, Y., Densification behavior and microstructure evolution of hot-pressed SiC—SiBCN ceramics, Science Direct, Ceramics International 41(2015) 8541-8551, 11 pp., http://dx.doi.org/10.1016/j.ceramint.2015.03.0610272-8842 © 2015 Elsevier Ltd and Techna Group S.r.l.

Mack, M.G., Coker, C.E., Development and Field Testing of Advanced Ceramic Proppants, Society of Petroleum Engineers, 2013, SPE 166323, 16 pp, Prepared for presentation at the SPE Annual Technical Conference and Exhibition held in New Orleans, Louisiana, USA, Sep. 30-Oct. 2, 2013.

Malczewski, R.M., Jahn, D.A., Schoenherr, W.J., Peroxide or Platinum? Cure System Considerations for Silicone Tubing Applications, Dow Corning Healthcare, 2003, 5 pp., Dow Corning Corporation, Printed in USA Form No. 52-1077-01.

Martínez, F.L., Ruiz-Merino, R., Del Prado, A., San Andrés, E., Mártil, I., González-Díaz, G., Jeynes, C., Barradas, N.P., Wang, L., Reehal, H.S., Bonding structure and hydrogen content in silicon nitride thin films deposited by the electron cyclotron resonance plasma method, 12 pp. This work was partially supported by the Ministry of Science and Technology (Spain) under contract TIC2001/1253.

Meador, M.A.B., Hurwitz, F.I., Gonczy, S.T., NMR Study of Redistribution Reactions in Blackglas™ and Their Influence on Oxidative Stability, Ceramic Engineering & Science Proceedings, Victor Greenhut, 1996, The American Ceramic Society 394-400, 7 pp.

Meals, R.N., Hydrosilation in the synthesis of organosilanes, 141-157, 17 pp., Silicone Products Department, General Electric Co., Waterford, New York.

Mera, G., Navrotsky, A., Sen, S., Kleebed, H-J., Riedel, R., Polymer-derived SiCN and SiOC ceramics—structure and energetics at the nanoscale, Journal of Materials Chemistry A, J. Mater. Chem. A, 2013, 1, 3826-3836, 11 pp., DOI: 10.1039/c2ta00727d, © The Royal Society of Chemistry 2013, RSC Publishing.

Sahin, Y., Preparation and some properties of SiC particle reinforced aluminum alloy composites, Materials and Design 24 (2003) 671-679, 9 pp., © 2003 Elsevier Science Ltd., doi:10.1016/S0261-3069(03)00156-0.

Salemi, S., Density Functional and Monte Carlo-Based Electron Transport Simulation in 4H-SiC(0001)/SiO2 DMOSFET Transition Region, 978-1-4673-5736-4/13/, © 2013 IEEE, 180-183, 4 pp.

Schawe, J., Riesen, R., Widmann, J., Schubnel, M., Jörimann, U., UserCom 1/2000, Information for Users of Meter Toledo thermal analysis systems, Brochure, 28 pp., Redaktion, Mettler Toledo GmbH, Analytical, Sonnenbergstrasse 74, CH-8603 Schwerzenbach, Schweiz.

Schiavion, M.A., Gervais, C., Babonneau, F., Soraru, G.D., Crystallization Behavior of Novel Silicon Boron Oxycarbide Glasses, Journal of the American Ceramic Society, vol. 87, No. 2. 203-208, 6 pp.

Schiavion, M.A., Redondo, S.U.A., Pina, S.R.O., Yoshida, I.V.P., Investigation on Kinetics of Thermal Decomposition in Polysiloxane Networks Used as Precursors of Silicon Oxycarbide Glasses, Journal of Non-Crystalline Solids, Jun. 2002, DOI: 10.1016/S0022-3093(02)01009-8, Journal of Non-Crystalline Solids 304 (2002) 92-100, 10 pp.

Schiavon, M.A., Armelin, N.A., Yoshida, I.V.P., Novel poly(borosiloxane) Precursors to Amorphous SiBCO Ceramics, Materials Chemistry and Physics, vol. 112, Issue 3, Dec. 20, 2008, pp. 1047-1054.

Schoenung, J.M., Kraft, E.H., Ashkin, D., Advanced silicon nitride components: A cost analysis, Ceramic Engineering and Science Proceedings), 497-504, 8 pp., Ersan Ustundag & Gary Fischman, © 1999 The American Ceramic Society.

SEHSC, Materials handling guide: Hydrogen-bonded silicon compounds developed by the operating safety committee of the silicones environmental, 39 pp., Health and Safety Council of North America, SiH Materials Handling Guide, Aug. 2007, 39, pp.

Serra, J., González, P., Liste, S., Serra, C., Chiussi, S., León, B., Pérez-Amor, M., Ylänen, H.O., Hupa, M., FTIR and XPS studies of bioactive silica based glasses, Journal of Non-Crystalline Solids 332 (2003) 20-27, 8 pp., © 2003 Elsevier B.V.

Shao, X., Dong, D., Parkinson, G., Li, C-Z., A Microchanneled Ceramic Membrane for Highly-Efficient Oxygen Separation, 7 pp., Electronic Supplementary Material (ESI) for Journal of Materials Chemistry A, This journal is © The Royal Society of Chemistry 2013.

Shorowordi, K.M., Laoui, T., Haseeb, A.S.M.A., Celis, J.P., Froyen, L., Microstructure and interface characteristics of B4C, SiC and Al2O3 reinforced Al matrix composites: a comparative study, Journal of Materials Processing Technology 142 (2003) 738-743, 6 pp, © 2003 Elsevier B.V.

Sid Richardson Carbon Company, Making Carbon Black, Graphics by Fred Hendrickson, Slides, 37 pp.

Smoak, R.H., Kraft, E.H., Sintered Alpha Silicon Carbide: Some Aspects of the Microstructure-Strength Relationship, 9 pp., The Carborundum Company Alpha Silicon Carbide Division, Niagara Falls, New York 14302, Presented at Fall Meeting American Ceramic Society, Sep. 27, 1977, Hyannis, Massachusetts.

Sone, H, Kaneko, T., Miyakawa, N., In Situ Measurements and Growth Kinetics of Silicon Carbide Chemical Vapor Deposition From Methyltrichlorosilane, Journal of Crystal Growth 219 (2000) 245-252, 8 pp., © 2003 Elsevier Science B.V.

(56) References Cited

OTHER PUBLICATIONS

Soraru, G.D., Modena, S., Chemical durability of silicon oxycarbide glasses, J. Am. Ceram. Soc., 85 [6] 1529-36 (2002), 8 pp.
Soraru, G.D, Dallapiccola, E., D'Andrea, G., Mechanical characterization of sol-gel-derived silicon oxycarbide glasses, J. Am. Ceram. Soc., 79 [8] 2074-80 (1996), 5 pp.
Soraru, G.D., Walter, S., Brequel, H. Enzo, S., Microstructural and mechanical characterization of sol gel-derived Si—O—C Glasses, Journal of the European Ceramic Society, Dec. 2002, 22 (2002) 2389-2400, 12 pp.
Soraru, G.D, Dalcanale, F., Campostrini, R., Gaston, A., Blum, Y., Carturan, S., Aravind, P.R., Novel polysiloxane and polycarbosilane aerogels via hydrosilylation of preceramic polymers, Communication, Journal of Materials Chemistry, J. Mater. Chem., 2012, 22, 7676-7680, 5 pp.
Soraru, G.D., Pederiva, L., Latournerie, J., Raj, R., Pyrolysis kinetics for the conversion of a polymer into an amorphous silicon oxycarbide ceramic, J. Am. Ceram. Soc., 85 [9] 2181-87 (2002), 7 pp.
Soraru, G.D., Liu, Q., Interrante, L.V., Apple, T., Role of Precursor Molecular Structure on the Microstructure and High Temperature Stability of Silicon Oxycarbide Glasses Derived from Methylene-Bridged Polycarbosilanes, Chem. Mater. 1998, 10, 4047-4054, 8 pp., Published on Web Nov. 17, 1998, © American Chemical Society.
Soraru, G.D., D'Andrea, G., Campostrini, R., Babonneau, F., Mariotto, G., Structural Characterization and High-Temperature Behavior of Silicon Oxycarbide Glasses Prepared from Sol-Gel Precursors Containing Si—H Bonds, J. Am. Ceram. Soc., 78 [2] 379-87 (1995), 9 pp.
Soukiassian, P., Amy, F., Silicon Carbide Surface Oxidation, Research Highlights, NSRRC Activity Report 2002/2003, 4 pp.
Sousa, B.F, Valeria, I., Yoshida, P., Ferrari, J.L., Schiavon, M.A., Silicon Oxycarbide Glasses Derived From Polymeric Networks with Different Molecular Architecture Prepared by Hydrosilylation Reaction, J Mater Sci (2013)48:1911-1919, 9 pp., DOI 10.1007 /s 10853-0 12-6955-4, Published online: Oct. 26, 2012, Copyright Springer Science+Business Media New York 2012.
SRI International, Ceramic Composites, website jpeg, 1 pp.
Strachota, A., Cerný, M., Glogar, P., Sucharda, Z., Havelcová, M., Chlup, Z., Dlouhý, I., Kozák, V. Preparation of Silicon Oxycarbide Composites Toughened by Inorganic Fibers via Pyrolysis of Precursor Siloxane Composites, 12 Annual Conference of the Materials Research Society of Serbia, Herceg Novi, Montenegro, Sep. 6-10, 2010, ACTA Physica Polonica A, vol. 120 (2011), No. 2, 5 pp.
Su, D., Li, Y-L, An, H-J, Liu, X., Hou, F., Li, J-Y, Fu, X., Pyrolytic Transformation of Liquid Precursors to Shaped Bulk Ceramics, Journal of the European Ceramic Society, vol. 30, Issue 6, Apr. 2010, pp. 1503-1511.
Suárez, M., Fernández, A., Menéndez, J.L., Torrecillas, R., Kessel, H.U., Hennicke, J., Kirchner, R., Kessel, T., Challenges and Opportunities for Spark Plasma Sintering: A Key Technology for a New Generation of Materials, Chapter 13, 23 pp., InTech, © 2013 Suarez et al, licensee InTech.
Suh, M.H., Kwon, W-T., Kim, E.B., Kim, S-R., Bae, S.Y., Choi, D.J. Kim, Y., H2 Permeable Nanoporous SiC Membrane for an IGCC Application, Journal of Ceramic Processing Research. vol. 10, No. 3 pp. 359-363 (2009), 5 pp.
Syväjärvi, M., Yakimova, R., Tuominen, M., Kakanakova-Georgieva, A., MacMillan, M.F., Henry, A., Wahab, Q., Janzen, E., Growth of 6H and 4H—SiC by Sublimation Epitaxy, Journal of Crystal Growth 197 (1999) 155-162, 8 pp., © 1999 Elsevier Science B.V.
TATA Chemicals Europe Limited, Solubility of Sodium Bicarbonate in Water, United Kingdom, 1 pp., www.tatachemicals.com.
Transmission Electron Microscopy, 111-136, 26 pp.
Tian, H. Ma, Q-S., Pan, Y., Liu, W., Structure and Mechanical Properties of Porous Silicon Oxycarbide Ceramics Derived from Silicone Resin with Different Filler Content, SciVerse ScienceDirect, Ceramics International 39 (2013) 71-74, 4 pp., © 2012 Elsevier Ltd. and Technical Group S.r.l.
Tomar, V., Nanocomposite Ceramics—What are Nanocomposite Ceramics?, Nanotechnology Thought Leaders—Insights from the World's Leading Players, 9 pp., Saved from URL http://www.azonano.com/article_aspx? ArticleID=250t.
Toney, F.L., Mack, D.J., The Next Generation of Foam: A Field Study of Northwestern Oklahoma Foam Fracturing, SPE 21644, 113-123, 11 pp., This paper was prepared for presentation at the Production Operations Symposium held in Oklahoma City, Oklahoma, Apr. 7-9, 1991, Copyright 1991, Society of Petroleum Engineers, Inc.
Topuz, B., Simsek, D., Çiftçioğlu, M., Preparation of monodisperse silica spheres and determination of their densification behavior, Science Direct, Ceramics International 41(2015) 43-52, 10 pp., © 2014 Elsevier Ltd. and Technical Group S.r.l.
Trottier, R., Dhodapkar, S., A Guide to Characterizing Particle Size and Shape, Instrumentation, CEP, Jul. 2014, 36-46, 11 pp.
Twigg, M.V., Richardson, J.T., Fundamentals and Applications of Structured Ceramic Foam Catalysts, Ind. Eng. Chem. Res. 2007, 46, 4166-417, 16 pp., 2007 American Chemical Society, Published on Web Feb. 24, 2007.
Ujihara, T., Maekawa, R., Tanaka, R., Sasaki, K., Kuroda, K., Takeda, Y., Solution Growth of High-Quality 3C—SiC crystals, Journal of Crystal Growth 310 (2008) 1438-1442, 5 pp., Available online Jan. 15, 2008, Science Direct, © 2007 Elsevier B.V.
Vakifahmetoglu, C., Colombo, P., A Direct Method for the Fabrication of Macro-Porous SiOC Ceramics from Preceramic Polymers, Advanced Engineering Materials 2008, 10, No. 3, 4 pp., DOI: 10.1002/adem.200700330, 256, © 2008 Wiley-VCH Verlag GmbH & Co. KGaA,Weinheim.
Vakifahmetoglu, C., Menapace, I., Hirsch, A., Biasetto, L., Hauser, R., Riedel, R., Colombo, P., Highly Porous Macro-and Micro-Cellular Ceramics from a Polysilazane Precursor, Ceramics International 35 (2009) 3281-3290, 10 pp., Science Direct, Available online Jun. 18, 2009, © 2009 Elsevier Ltd. and Technical Group S.r.l.
Van Der Vlis, A.C., Haafkens, R., Schipper, B.A., Visser, W., Criteria for Proppant Placement and Fracture conductivity, Society of Petroleum Engineers of AIME, SPE 5637, 15 pp., Copyright 1975, American Institute of Mining, Metallurgical, and Petroleum Engineers, Inc.
Wacker, SILRES® MSE 100: A Unique Silicone Resin that Cures at Room Temperature, Wacker Chemie AG, 81737 München, Germany, 2 pp.
Walter, S, Soraru, G.D., Bréquel, H., Enzo, S., Microstructural and mechanical characterization of sol gel-derived Si—O—C glasses, Journal of the European Ceramic Society 22 (2002) 2389-2400, 12 pp., © 2002 Published by Elsevier Science Ltd.
Wang, F., Gill, W.N., Kirk, C.A., Apple, T., NMR characterization of postcure temperature effects on the microstructures of Blackglas™ Resin and Ceramic, Journal of Non-Crystalline Solids 275 (2000) 210-215, 6 pp, , © 2000 Published by Elsevier Science B.V.
Wang, F., Apple, T., Gill, W.M., Thermal Redistribution Reactions of Blackglas™ Ceramic, Journal of Applied Polymer Science, vol. 81, 143-152 (2001), 10 pp, © 2001 John Wiley & Sons, Inc.
Wang, S.F., Zhang, J. Luo, D.W., Gu, F., Tang, D.Y., Dong, Z.L., Tan, G.E.B., Que, W.X., Zhang, T.S., Li, S., Kong, L.B., Transparent Ceramics: Processing, Materials and Applications, Progress in Solid State Chemistry 41 (2013) 20-54, 34 pp., , © 2012 Published by Elsevier Ltd.
Wijesundara, M.B.J., Azevedo, R., SiC Materials and Processing Technology, Chapter 2, Silicon Carbide Microsystems for Harsh Environments, MEMS Reference Shelf 22, DOI 10.1007/978-1-4419-7121-0 2, 33-95, 63 pp., © Springer Science+Business Media, LLC 2011.
Wiley, John & Sons, Inc., Phenolic resins, Encyclopedia of Polymer Science and Technology, vol. 7, 322-368, 47 pp., © John Wiley & Sons, Inc.
Witucki, G.L., A silane primer: Chemistry and applications of alkoxy silanes, Back to Basics, Reprinted from Jul. 1993 Issue of the

(56) References Cited

OTHER PUBLICATIONS

Journal of Coatings Technology, vol. 65, No. 822, 57-60, 4 pp., Copyright 1993 by the Federation of Societies for Coatings Technology, Blue Bell, PA USA, Presented at the 57th Annual Meeting of the Federation of Societies of Coatings Technology on Oct. 21, 1992 in Chicago, IL.

Wright, P.V., Beevers, M.S., Preparation of cyclic polysiloxanes, Chapter 3, 25 pp.

Wu, Jiquan, Li, Y., Chen, L., Zhang, Z., Wang, D., Xu, C., Simple fabrication of micro/nano-porous SiOC foam from polysiloxane, communication, Journal of Materials Chemistry, J. Mater. Chem., 2012, 22, 6542-6545, 4 pp., © The Royal Society of Chemistry 2012.

Yazdanfar, M., Pedersen, H., Sukkaew, P., Ivanov, I.G., Danielsson, Ö., Kordina, O., Janzén, E., On the Use of Methane As a Carbon Precursor in Chemical Vapor Deposition of Silicon Carbide, Journal of Crystal Growth, 390 (2014) 24-29, 6 pp., Available online Dec. 27, 2013, © 2013 Elsevier B.V.

Yeo, I-G, Lee, T-W, Lee, W-J., Shin, B-C, Choi, J-W, Ku, K-R, Kim, Y-H, The Quality Investigation of 6H—SiC crystals Grown by a Conventional PVT Method With Various SiC Powders, Transactions on Electrical and Electronic Materials, vol. 11, No. 2, pp. 61-64, 4 pp., Apr. 25, 2010, © 2010 KIEEME.

Yilmaz, O., Buytoz, S., Abrasive wear of A12O3-reinforced aluminum-based MMCs, Composites Science and Technology 61 (2001) 2381-2392, 12 pp., © 2001 Published by Elsevier Science Ltd., PII: S0266-3538(01)00131-2.

Yoo, K-C, Ruderman, W., Growth of Single Crystal Beta Silicon Carbide, Phase I, Final Report for the period Jul. 1992 through Dec. 1992, Office of Naval Research, Washington, DC, Contract N00014-92-C-0127, INRAD, Inc. Northvale, NJ 07647, 33 pp.

Yoon, J.L., Kim, J. Il, Kim, S.R, Kwon, W.T., Shin, D-G., Kim, Y., Fabrication of SiOC/C coatings on stainless steel using poly(phenyl carbosilane) and their anti-corrosion properties, Innovative Processing and Manufacturing of Advanced Ceramics and Composites II, 71-77, 4 pp.

Zhmakin, A.I., Modelling of Heat Transfer in Single Crystal Growth, Ioffe Physical Technical Institute, Russian Academy of Sciences, St. Petersburg, Russia, Softimpact Ltd., P.O. 83, 194156 St. Petersburg, Russia, 25 pp.

Dvornic, P.R., Thermal properties of polysiloxanes, Chapter 7, R.G. Jones et al., (eds.), Silicon-Containing Po9lymers, 185-212, © 2000 Kluwer Academic Publishers. Printed in the Netherlands, 28 pp.

Abderrazak, H., Hmida, E.S.B.H., Silicon carbide: synthesis and properties, properties and application of silicone carbide, Chapter 16, Apr. 2011, Prof. Rosario Gerhardt (Ed.), ISBN: 978-953-307-201-2, 361-388, 29 pp., InTech, Available from: http://www.intechopen.com/books/properties-and-applications-of-siliconcarbide/silicon-carbide-synthesis-and-properties.

Andriot, M, Degroot, J.V., Jr., Meeks, R., Gerlach, E., Jungk, M., Wolf, A.T., Cray, S., Easton, T., Mountney, A., Leadley, S., Chao, S.H., Colas, A., De Buyl, F., Dupont, A., Garaud, J.L., Gubbels, F., Lecomte, J.P., Lenoble, B. Stassen, S., Stevens, C., Thomas, X., Shearer, G., Silicones in industrial applications, 106 pp., Dow Corning.

American National Standards Institute (ANSI) and American Petroleum Institute (API), Measurement of properties of proppants used in hydraulic fracturing and gravel-packing operations, ANSI/API Recommended Practice 19C, May 2008, First Edition, ISO 13503-2:2006 (Identical), Petroleum and natural gas Industries—Completion fluids and materials, Copyrighted Material Licensed to Bruce Bricco on Feb. 5, 2013 for licensee and #39's use only, Distributed by Thomson Reuters (Scientific), Inc., 42 pp.

American National Standards Institute (ANSI) and American Petroleum Institute (API), Measuring the long term conductivity of proppants, ANSI/API Recommended Practice 19D, First Edition, May 2008, Errata, Jul. 2008, ISO 13503-5 (Identical), Part 5: Procedures for measuring the long-term conductivity of proppants, Copyrighted Material Licensed to Bruce Bricco on Feb. 5, 2013 for licensee and #39's use only, Distributed by Thomson Reuters (Scientific), Inc., 35 pp.

Araújo, F.G., Latorre, G.P., Hench, L.L., Structural evolution of a porous type-VI sol-gel silica glass, Journal of Non-Crystalline Solids 185 (1995) 41-48, 8 pp., © 1995 Elsevier Science B.V.

Ashland, Corrosion Resistant Fiberglass Reinforced Pipe—FRP, 3 pp., http://www.ashland.com/strategic-applications/APM/corrosion-resistant-FRP.

Aud, W.W., Poulson, T.D., Burns, R.A., Rushing, T.R., Orr, W.D., Lateral proppant distribution: The good, the bad, and the ugly of putting frac jobs away, Society of Petroleum Engineers, Inc., SPE 56725, Copyright 1999, 10 pp.

Baker, R.W., Lokhandwala, K., Natural gas processing with membranes: An overview, membrane technology and research, Inc., California, Received for Review Aug. 8, 2007, Revised Manuscript Received Nov. 30, 2007, Accepted, Dec. 4, 2007, IE071083W, 13 pp.

Bakumov, V., Schwarz, M., Kroke E., Emulsion processing of polymer-derived porous Si/C/(O) ceramic bodies, Institute of Inorganic Chemistry, Germany, Accepted Apr. 2, 2009, Available online May 14, 2009, Journal of the European Ceramic Society 29 (2009) 2857-2865, 9 pp., © 2009 Elsevier Ltd.

Bannwarth, H., Gas physics and vacuum technology, Liquid Ring Vacuum Pumps, Compressors and Systems, 110 pp., © 2005 Wiley-VCH Verlag GmbH & Co. KGaA, Weinheim ISBN: 3-527-31249-8.

Bayyaa, S.S., Villalobos, G.R., Hunt, M.P., Sangheraa, J.S., Sadowski, B.M., Aggarwal, I.D., Cinibulk, M., Carney, C., Keller, K., Development of transparent polycrystalline beta-silicon carbide, Material Technologies and Applications to Optics, Structures, Components. and Sub-Systems, edited by Joseph L. Robichaud, Matthias Krodel, William A. Goodman, Proc. of SPIE vol. 8837, 88370S © 2013 SPIE CCC code' 0277-786X/13/$18 . doi: 10.1117112.2023954, 7 pp.

Bazarjani, M.S., Prasad, R.M., Schitco, C., Gurlo, A., Riedel, R., A fundamental design approach towards microporous polymer derived nanocomposites , for gas separation applications, [O5B.2], Technische Universität Darmstadt, Germany, 2 pp.

Bernardo, P., Clarizia, G., 30 years of membrane technology for gas separation, chemical engineering transactions, vol. 32 (2013), 1999-2004, DOI: 10.3303/CET1332334, ISBN 978-88-95608-23-5; ISSN 1974-9791, 6 pp., © 2013 AIDIC Servizi S.r.l. ISBN 978-88-95608-23-5; ISSN 1974-9791.

Bernardo, E., Fiocco, L., Parcianello, G., Storti, E., Colombo, P., Advanced ceramics from preceramic polymers modified at the nano-scale: A review, Materials 2014, 7, 1927-1956; doi:10.3390/ma7031927, 30 pp.

Bernardo, E., Colombo, P., Manias, E., SiOC glass modified by montmorillonite clay, Ceramics International 32 (2006) 679-686, 8 pp., © 2005 Elsevier Ltd and Techna Group S.r.l.

Berndt, F., Jahn, P., Rendtel, A., Motz, G., Ziegler, G., Monolithic SiOC ceramics with tailored porosity, Institute for Materials Research (WFN), D-2 J 502, Germany, 4 pp.

Blum, Y., Soraru, G.D., Ramaswamy, A.P., Hui, D., Carturan, S.M., Controlled mesoporosity in SiOC via chemically bonded polymeric "Spacers" (2013), Journal of the American Ceramic Society, vol. 96, No. 9, 8 pp., DOI: 10.1111/jace.12485, © 2013 The American Ceramic Society.

Boyle, M.A., Martin, C.J., Neuner, J.D., Epoxy Resins, Constituent Materials, 12 pp.

Brequei, H., Parmentier, T.J., Walter, S., Badheka, R., Trimmel, G., Masse, S., Latournerie, J., Dempsey, P., Turquat, C., Desmartin-Chomel, A., Le Neindre-Prum, L. Jayasooriya, U.A., Hourlier, D., Kleebe, H.-J., Soraru, G.D., Enzo, S., Babonneau, F., Systematic structural characterization of the high-temperature behavior of nearly stoichiometric silicon Oxycarbide Glasses, Chem. Mater. (2004) 16, 2585-2598, 14 pp., © 2004 American Chemical Society, Published on Web May 29, 2004.

Brundle, C. R., Evans, C.A., Jr., Wilson, S., Encyclopedia of materials characterization, surfaces, interfaces, thin films, This book was acquired, developed, and produced by Manning Publications Co., © 1992 by Butterworth-Heinemann, a division of Reed Pub-

(56) References Cited

OTHER PUBLICATIONS lishing (USA) Inc., Stoneham, MA02180, Manning Publications Co., Greenwich, CT 06830, 1 0 9 8 7 6 5 4 3, Printed in the USA, 782 pp.
Budden, G., Some like it hot, Dow Corning Limited, U.K., Silicone characteristics, 15 pp.
Bujalski, D.R., Grigoras, S., Lee, W-L., Wieber, G.M., Zank, G.A., Stoichiometry control of SiOC ceramics by siloxane polymer functionality, Journal of Materials Chemistry, J. Mater. Chem., 1998, 8(6), 1427-1433 1433, 7 pp.
Bunsell, A.R., Piant, A., A review of the development of three generations of small diameter silicon carbide fibres, J Mater Sci 41 (2006) 823-839, 17 pp., DOI: 1O.1007/s 10853-006-6566-z, © 2006 Springer Science + Business Media, Inc.
Casado, C.M., Cuadrado, I., Morán, M., Alonso, B., Barranco, M., Losada, J., Cyclic siloxanes and silsesquioxanes as cores and frameworks for the construction of ferrocenyl dendrimers and polymers, Applied Organometallic Chemistry, App. Organometal. Chem. 13, 245-259 (1999), 15 pp., © 1999 John Wiley & Sons, Ltd.
Chen, T., Dong, M., Wang, J., Zhang, L., Li, C., Study on properties of silicon oxycarbide thin films prepared by RF magnetron sputtering, Science and Technology on Surface Engineering Laboratory, Lanzhou Institute of Physics, Lanzhou 730000, China, 5 pp., 2nd International Conference on Electronic & Mechanical Engineering and Information Technology (EMEIT-2012), Published by Atlantis Press, Paris, France.
Cho, S.H., White, S.R., Braun, P.V., Room-temperature polydimethylsiloxane-based self-healing polymers, Chemistry of Materials, pubs.acs.org/cm, dx.doi.org/10.1021/cm302501b | Chem. Mater. 2012, 24, 4209-4214, 6 pp., © 2012 American Chemical Society.
Chung, D-W, Kim, T.G., Study on the effect of platinum catalyst for the synthesis of polydimethylsiloxane grafted with polyoxyethylene, J. Ind. Eng. Chem, vol. 13, No. 4, (2007) 571-577, 7 pp.
Clark, M.D.T., Carbon black, Chapter 9, Petroleum Specialty Products, Extensive revision and editing by Heather Wansbrough following correspondence with Steve Lipsham, 43 pp.
Colas, A., Silicones: preparation, properties, and performance, Dow Corning, Life Sciences, © 2005 Dow Corning Corporation, Printed in USA VIS2339 Form No. 01-3077-01, 14 pp.
Collins, P., Heithaus, M., Adams, C., Li, J.H., Chemical modification of carbon black for improved performance in coatings, Cabot Corporation, Coatings Business Unit, CRP-216-294, 9 pp.
Colombo, P., Raj, R, editors, Advances in polymer derived ceramics and composites, Ceramic Transactions, vol. 213, 28 pp., A Collection of Papers Presented at the 8th Pacific Rim Conference on Ceramic and Glass Technology, May 31-Jun. 5, 2009, Vancouver, British Columbia, Volume Editor, Singh, M., A John Wiley & Sons, Inc. Publication.
Colombo, P., Sglavo, V. Pippel, E., Woltersdorf, J., Joining of reaction-bonded silicon carbide using a preceramic polymer, J. Journal of Materials Science 33 (1998) 2405 2412, 8 pp., © 1998 Chapman & Hall.
Colombo, P., Mera, G., Riedel, R., Soraru, G.D., Polymer-derived ceramics: 40 years of research and innovation in advanced ceramics, J. Am. Ceram, Soc. 93 [7] 1805-1837 (2010), 33 pp., © 2010 The American Ceramics Society.
Colombo, P., Riedel, R., Soraru, G.D., Kleebe, H-J., Polymer derived ceramics from nano-structure to applications, Printed in the USA, 10 9 8 7 6 5 4 3 2, © 2010 DEStech Publications, Inc., ISBN: 978-1-60595-000-6, 475 pp.
Colombo, P., Modesti, M., Silicon oxycarbide ceramic foams from a preceramic polymer, Journal of the American Ceramic Society, vol. 82, No. 3, 573-78 (1999), 6 pp.
CoorsTek Material, Material Properties Charts, Important Information, 18 pp. CoorsTek, Inc., Golden, Colorado.
Craddock, D.L., Goza, B.T., Bishop, J.C., A case history-fracturing the morrow in southern blaine and western Canadian counties, Oklahoma, SPE 11567, 6 pp., Copyright 1983 Society of Petroleum Engineers of AIME, This paper was presented at the 1983 Production Operation Symposium held in Oklahoma City, Oklahoma, Feb. 27-Mar. 1, 1983.
Cypryk, M., Apeloig, Y., Mechanism of the acid-catalyzed Si—O bond cleavage in siloxanes and siloxanols. A theoretical study, Organometallics (2002), vol. 21, No. 11, 2165-2175 , 11 pp., Publication on Web Apr. 24, 2002, © American Chemical Society.
Dalcanale, F. Grossenbacher, J., Blugan, G., Gullo, M.R, Lauria, A., Brugger, J., Tevaearai, H., Graule,T., Niederberger, M., Kuebler, J., Influence of carbon enrichment on electrical conductivity and processing of polycarbosilane derived ceramic for MEMS applications, ScienceDirect, Journal of the European Ceramic Society 34 (2014) 3559-3570, 12 pp., © 2014 Elsevier Ltd.
Dasgupta, R., Aluminum alloy-based metal matrix composites: a potential material for wear resistant applications, Research Article, International Scholarly Research Network , ISRN Metallurgy, vol. (2012), Article ID 594573, 14 pp., doi:10.5402/2012/594573 , CSIR—Advanced Materials and Processes Research Institute (AMPRI), Hoshangabad Road, Madhya Pradesh, Bhopal 462064, India, © 2012 Rupa Dasgupta.
De Vekki, D.A., Skvortsov, N.K., Metal complex catalyzed , hydrosilylation of vinyl-with hydrosiloxanes, (A Review), Chemistry and Chemical Technology, Technology of Organic Substances, 18 pp.
De Vos, R.M., Verweij, H., High-selectivity, high-flux silica membranes for gas separation, Science 279, 1710 (1998), DOI: 10.1126/science.279.5357.1710, 3 pp., American Association for the Advancement of Science, Washington, DC 20005.
Dow Corning, Safe handling of silicon hydride containing polysiloxanes, Updated Aug. 22, 2003, 29 pp., Printed in U.S.A. FPH 33079 Form No. 24-711A-01.
Dow Corning, Xiameter® MHX-1107 Fluid 20CST and 30CST, Polymethylhydrogensiloxane, Feb. 16, 2012, 2 pp., Form No. 95-1087-01, © 2012 Dow Corning Corporation.
Dume, B., Silicon carbide shows promise for quantum computing, physicsworld.com, Nov. 4, 2011, 2 pp., Retrieved: Aug. 16, 2015: http://physicsworld.com/cws/articlelnews/2011/nov/04/silicon-carbide-shows-promise-for-quantum-computing.
Entegris, Inc., Supersic® materials, © 2011-2012 Entegris, Inc., 2 pp., Printed in USA.
Eom, J-H., Kim, Y-W., Song, I-H, Kim, H-D., Microstructure and properties of porous silicon carbide ceramics fabricated by carbothermal reduction and subsequent sintering process, Materials Science and Engineering Materials Science and Engineering, A 464 (2007) 129-134, 6 pp., © 2007 Elsevier B.V.
Fernandez, G.J., Murr, L.E., Characterization of tool wear and weld optimization in the friction-stir welding of cast aluminum Materials Characterization 359+20% SiC metal-matrix composite, Materials Characterization 52 (2004) 65-75, 11 pp., © 2004 Elsevier Inc.
Friess, M., Bill, J., Golczewski, J., Zimmermann, A., Aldinger, F., Crystallization of polymer-derived silicon carbonitride at 1873 k under nitrogen overpressure, J. Am. Ceram. Soc., 85 [10] 2587-89 (2002), 3 pp.
Gallis, S., Huang, M., Nikas, V., Kaloyeros, A. E., Nguyen, A. P. D., Stesmans, A., Afanas'ev, V. V., The origin of white luminescence from silicon oxycarbide thin films, Research Gate, Applied Physics Letters 104, 061906 (2014), DOI: 10.1063/1.4865100, 6 pp., AIP Publishing, New York.
Microsemi PPG, Gallium Nitride (GaN) versus Silicon Carbide (SiC) in the High Frequency (RF) and Power Switching Applications, 8 pp., Digikey.com.
Miracle, D. B., Donaldson, S.L., Introduction to Composites, Air Force Research Laboratory, 15 pp.
Mixing and Agitation, Chapter 10, 287-304, 18 pp.
Modern Dispersons, Insights on Carbon Black Fundamentals, 8 pp., 78 Marguerite Ave., Leonminster, MA 01453-4227 USA, www.moderndispersons.com.
Montgomery, D.C., Runger, G.C., Applied Statistics and Probability for Engineers, Third Edition, 976 pp., Copyright 2003 © John Wiley & Sons, Inc., Library of Congress Cataloging-in-Publication Data, Includes bibliographical references and index., ISBN 0-471-20454-4 (acid-free paper), 1. Statistics. 2. Probabilities. I. QA276.

(56) References Cited

OTHER PUBLICATIONS

12.M645 2002, 519.5—dc21, 2002016765, Printed in the United States of America., 10 9 8 7 6 5 4 3 2 1.

Morcos, R.M., Navrotsky, A., Varga,T., Blum, Y., Ahn, D., Poli, F., Müller, K. Raj, R., Energetics of SixOyCz polymer-derived ceramics prepared under varying conditions, Journal of the American Ceramic Society, 2008, J. Am. Ceram. Soc. 91 [9] 2969-2974 (2008), 6 pp., © 2008 The American Ceramic Society.

Moysan, C., Riedel, R., Harshe, R., Rouxel, T., Augereau, F., Mechanical characterization of a polysiloxane-derived SiOC Glass, Journal of the European Ceramic Society 27 (2007) 397-403, 7 pp.

Myers, R., Potratz, J., Moody, M., Field application of new lightweight proppant in appalachian tight gas sandstones, Society of Petroleum Engineers Inc., Sep. 2004, SPE 91469, 9 pp., Prepared for presentation at the2004 SPE Eastern Regional Meeting, Charleston, WV., Copyright 2004 Society of Petroleum Engineers.

Mynbaeva, M.G., Abramov, P.L., Lebedev, A.A., Tregubova, A.S., Litvin, D.P., Vasiliev, A.V., Chemekova, T.Y., Makarov, Y.N., Fabrication of improved-quality seed crystals for growth of bulk silicon carbide, fabrication, treatment, and testing of materials and structures, Semiconductors, vol. 45, No. 6, 2011, 828-831, 4 pp.

Narisawa, M., Iwase, A., Watase, S., Matsukawa, K., Kawai, T., Photo luminescent properties of polymer derived ceramics at near stoichiometric SiO2—xSiC—y(H) compositions, Innovative Processing and Manufacturing of Advanced Ceramics and Composites II, 79-84, 4 pp.

Narisawa, M., Silicone resin applications for ceramic precursors and composites, Review, Materials 2010, 3, 3518-3536; 19 pp., doi:10.3390/ma3063518, Materials, ISSN 1996-1944.

NextelTM, 3M, Ceramic Textiles Technical Notebook, www.3M.com/ceramics, 98-0400-5870-7, Nov. 2004, 55 pp.

Nguong, C. W., Lee, S. N. B., Sujan, D., A Review on Natural Fibre Reinforced Polymer Composites, World Academy of Science, Engineering and Technology, International Journal of Chemical, Molecular, Nuclear, Materials and Metallurgical Engineering vol. 7, No. 1, 2013, International Scholarly and Scientific Research & Innovation 7(1) 2013, 8 pp., International Science Index, vol. 7, N:1, 2013, waset.org/Publication/6783.

Norris, A., Silicones: ideal material solutions for the photovoltaic industry, Photovoltaics International, www.pv-tech.org., 3 pp., © 2008 Dow Corning.

Nyczyk-Malinowska, A., Wójcik-Bania, M., Gumula, T., Hasik, M., Cypryk, M. Olejniczak, Z., New Precursors to SiCO Ceramics Derived from Linear Poly(vinylsiloxanes) of Regular Chain Composition, Feature Article, ScienceDirect, Journal of the European Ceramic Society 34 (2014) 889-902, 14 pp., © 2013 Elsevier Ltd.

Nyczyk, A., Paluszkiewicz, C., Pyda, A., Hasik, M., Preceramic polysiloxane networks obtained by hydrosilylation of 1,3,5,7-tetravinyl-I ,3,5,7-tetramethylcyclotetrasiloxane, Spectrochimica Acta Part A: Molecular and Biomolecular Spectroscopy, Spectrochimica Acta Part A 79 (2011) 801-808, 8 pp.

Orion, Carbon Black Pigments for Industrial Coatings, Technical Information 1458, 12 pp., 2013 Orion Engineered Carbons GmbH, Dec-3146 Dec. 2013.

Oteo, J.L., Mazo, M.A., Palencia, C., Rubio, F., Rubio, J., Synthesis and characterization of silicon oxycarbide derived nanocomposites obtained through ceramic processing of TEOS/PDMS preceramic materials, Journal of Nano Research vol. 14 (2011) pp. 27-38, 15 pp., © 2011 Trans Tech Publications. Switzerland, doi: 10.4028/www.scientijic.net/JNanoR.14.27, Online available since Apr. 14, 2011 at www.scientific.net.

Palisch, T., Duenckel, R., Chapman, M., Woolfork, S., Vincent, M.C., How to Use and Misuse Proppant Crush Tests—Exposing the Top 10 Myths, SPE 119242, 15 pp., Copyright 2009, Society of Petroleum Engineers, This paper was prepared for presentation at the 2009 SPE Hydraulic Fracturing Technology Conference held in The Woodlands, Texas, USA, Jan. 19-21, 2009.

Pantano, C.G., Singh, A.K., Zhang. H., Silicon oxycarbide glasses, Journal of Sol-Gel Science and Technology 14, 7-25 (1999), 19 pp., © 1999 Kluwer Academic Publishers. Manufactured in The Netherlands.

Parameters, Basic Parameters of Silicon Carbide (SiC), SiC Silicon Carbide, 5 pp., www.ioffe.rssi.ru/SVA/NSM/Semicond/SiC/basic.html.

Park, H-K, Sung, I-K, Kim, D-P, A facile route to prepare high surface area mesoporous SiC From SiO2 sphere templates, J. Mater. Chem., 2004, 14, 3436-3439, 4 pp., First published as an Advance Article on the web Sep. 22, 2004, Purchased by davis.rand @meliorinnovations.com on Oct. 6, 2015.

Park, H.., Review on the Current Status of Magnesium Smelting, Geosystem Engineering, 11(1), 13-18 (Mar. 2008), 6 pp.

Pearson, C. M., Griffin, L., Wright, C., Weijers, L., Breaking Up Is Hard to Do: Creating Hydraulic Fracture Complexity in the Bakken Central Basin, SPE 163827, 15 pp., Copyright 2013, Society of Petroleum Engineers.

Pearson, C. M., Griffin, L., Chikaloff, J., Measuring Field Supplied Proppant Conductivity—Issues Discovered in an Operator's Multi-Year Testing Program in the Bakken Shale, SPE 168641, 12 pp., Copyright 2014, Society of Petroleum Engineers.

Pena-Alonso, R., Rubio, J., Rubio, F., Oteo, J.L., FT-IR and Porosity Study of Si—B—C—O Materials Obtained from TEOS-TEB-PDMS Derived Gel Precursors, Journal of Sol-Gel Science and Technology 26, 195-199, 5 pp., 2003, © 2003 Kluwer Academic Publishers. Manufactured in The Netherlands.

Pippel, E., Lichtenberger, O., Woltersdorf, J., Identification of silicon oxycarbide bonding in Si—C—O-glasses by EELS, 2 pp., Journal of Materials Science Letters, 19, 2000, 2059-2060, © 2000 Kluwer Academic Publishers.

Pitcher, M.W., Joray, S.J., Bianconi, P.A., Smooth Continuous Films of Stoichiometric Silicon Carbide from Poly(methylsilyne), Adv. Mater. 2004, 16, No. 8, Apr. 19, 4 pp., © 2004 Wiley-VCH Verlag GmbH & Co. KGaA, Weinheim DOI: 10.1002/adma.200306467.

Plawsky, J.L., Wang, F., Gill, W.N., Kinetic Model for the Pyrolysis of Polysiloxane Polymers to Ceramic Composites, AIChE Journal, Oct. 2002, vol. 48, No. 10, 2315-2323, 9 pp.

Poddar, P., Srivastava, V.C., De, P.K., Sahoo, K.L., Processing and mechanical properties of SiC reinforced cast magnesium matrix composites by stir casting process, Materials Science and Engineering A 460-461 (2007) 357-364, 8 pp., © 2007 Elsevier B.V.

Polymer to Ceramic Transformation, [Image], 1 pp.

Pomorski, T. A., Bittel, B. C., Lenahan, P. M., Mays, E., Ege, C., Bielefeld, J., Michalak, D., King, S. W., Defect Structure and Electronic Properties of SiOC:H Films Used for Back End of Line Dielectrics, Journal of Applied Physics 115, 234508 (2014), 21 pp., doi: 10.1063/1.4882023, AIP Publishing.

Post, T., Understanding the Real World of Mixing, CEP Mar. 2010, 25-32, 8 pp.

Pradeep, V.S., Study of silicon oxycarbide (SiOC) as anode materials for Li-ion batteries, Dec. 2013, 178 pp., Doctoral School in Materials University of Trento, Italy, Department of Industrial Engineering, Advisor: Prof. Gian Domenico Soraru, Co-Advisor: Dr.-Ing. Magdalena Graczyk-Zajac.

Qian, B., Shen, Z., Laser sintering of ceramics, Journal of Asian Ceramic Societies 1 (2013 ) 315-321, 7 pp., ScienceDirect, © 2013 The Ceramic Society of Japan and the Korean Ceramic Society, Production and Hosting by Elsevier B.V.

Raj, R., Riedel, R., Soraru, G.D., Introduction to the Special Topical Issue on Ultrahigh-Temperature Polymer-Derived Ceramics, Ultrahigh-Temperature Ceramics, J. Am. Ceram. Soc., 84 [10] 2158-59 (Oct. 2001), 2 pp.

Rangarajan, S., Aswath, P.B., Role of Precursor Chemistry on Synthesis of Si—O—C and Si—O—C—N Ceramics by Polymer Pyrolysis, Journal of Materials Science, Apr. 2011, J Mater Sci (2011) 46:2201-2211, 14 pp, DOI: 10.1007/s10853-010-5058-3, Published online: Nov. 24, 2010, Springer Science+Business Media, LLC 2010.

Rashed, A.H., Properties and Characteristics of Silicon Carbide, 22 pp., Copyright 2002 Poco Graphite, Inc., Decatur, TX 76234.

Raysoni, N. Weaver, J., Long-term proppant performance, SPE 150669, 16 pp., Copyright 2012, Society of Petroleum Engineers,

(56) References Cited

OTHER PUBLICATIONS

This paper was prepared for presentation at the SPE International Symposium and Exhibition on Formation Damage Control held in Lafayette, Louisiana, USA, Feb. 15-17, 2012.

Renlund, G.M., Prochazka, S., Doremus, R.H., Silicon oxycarbide glasses: Part I. preparation and chemistry, J. Mater. Res., vol. 6, No. 12, Dec. 1991, 2716-2722, 7 pp., © 1991 Materials Research Society.

Renlund, G.M., Prochazka, S., Doremus, R.H., Silicon oxycarbide glasses: Part II. structure and properties, J. Mater. Res., vol. 6, No. 12, Dec. 1991, 2723-2734, 12 pp.

Revis, A., Discussion Slides, Phone Conference, Aug. 4, 2015, 1:30 p.m., 20 pp.

Roewer, G., Herzog, U., Trommer, K. Müller, E., Frühauf, S., Silicon Carbide—A Survey of Synthetic Approaches, Properties and Applications, Structure and Bonding, vol. 101, 59-135, 77 pp., © Springer-Verlag Berlin Heidelberg 2002.

Rogers Corporation, Silicone Materials Selection Guide, Bisco Silicones, Brochure, High Performance Foams Division, Carol Stream, IL, USA, 9 pp., Printed in USA. 1110-1111-5.0AG, Publication #180-016.

Romero, M., Rawlings, R.D., Rincón, J.Ma., Nucleation and crystal growth in glasses from inorganic wastes from urban incineration, Journal of Non-Crystalline Solids, 271 (2000) 1-2, 106-118; DOI: 10.1016/S0022-3093(00) 00082-X, 20 pp.

Rouxel, T., Elastic Properties and Short-to Medium-Range Order in Glasses, J. Am. Ceram. Soc., 90 [10] 3019-3039 (2007), 21 pp., DOI: 10.1111/j.1551-2916.2007.01945.x, © 2007, The American Ceramic Society.

Ryan, J.V., Free Carbon Structure in Silicon Oxycarbide Thin Films, A Thesis in Materials Science and Engineering, 2007, 175 pp., The Pennsylvania State University Graduate School, Copyright © 2007 Joseph V. Ryan, Submitted in Partial Fulfillment of the Requirements for the Degree of Doctor of Philosophy, Dec. 2007.

Saha, A., Raj, R., Williamson, D.L., A Model for the nanodomains in polymer-derived SiCO, J. Am. Ceram. Soc., 89 [7] 2188-2195 (2006), 8 pp., vol. 89, No. 7., © 2006 The American Ceramic Society.

Saha, A., Raj, R., Crystallization maps for SiCO amorphous ceramics, J. Am. Ceram. Soc., 90 [2] 578 583 (Feb. 2007), 7 pp., © 2006 The American Ceramic Society.

Sahimi, M., Tsotsis, T., Rahn, L., Nanoporous membranes for hydrogen production: Experimental studies and molecular simulations, 3 pp., 2013 Annual Merit Review and Peer Evaluation Meeting, DOE Hydrogen and Fuel Cells Program.

\* cited by examiner

BLACK CERAMIC ADDITIVES, PIGMENTS, AND FORMULATIONS

This application: (i) claims under 35 U.S.C. §119(e)(1) the benefit of the filing date of Feb. 28, 2014 of U.S. provisional application Ser. No. 61/1946,598; (ii) claims under 35 U.S.C. §119(e)(1) the benefit of the filing date of Jan. 21, 2015 of U.S. provisional application Ser. No. 62/106,094; and, (iii) is a continuation-in-part of U.S. patent application Ser. No. 14/268,150 filed May 2, 2014, which claims, under 35 U.S.C. §119(e)(1), the benefit of the filing date of May 2, 2013 of U.S. provisional application Ser. No. 61/818,906 and the benefit of the filing date of May 3, 2013 of U.S. provisional application Ser. No. 61/818,981, the entire disclosures of each of which are incorporated herein by reference.

BACKGROUND OF THE INVENTION

Field of the Invention

The present inventions relate to black materials and formulations utilizing these materials. Generally, the present inventions relate to: ceramic materials having blackness, black color, and which are black; starting compositions for these ceramic materials, and methods of making these ceramic materials; and formulations, compositions, materials and devices that utilize or have these ceramic materials. In particular, embodiments of the present inventions include: black ceramics having silicon, oxygen and carbon, and methods of making these ceramics; and devices, structures and apparatus that have or utilize these formulations, plastics, paints, inks, coatings and adhesives containing these black ceramics.

As used herein, unless stated otherwise, the terms "color," "colors" "coloring" and similar such terms are be given their broadest possible meaning and would include, among other things, the appearance of the object or material, the color imparted to an object or material by an additive, methods of changing, modifying or affecting color, the reflected refracted and transmitted wavelength(s) of light detected or observed from an object or material, the reflected refracted and transmitted spectrum(s) of light detected or observed from an object or material, all colors, e.g. white, grey, black, red, violet, amber, almond, orange, aquamarine, tan, forest green, etc., primary colors, secondary colors, and all variations between, and the characteristic of light by which any two structure free fields of view of the same size and shape can be distinguish between.

As used herein, unless stated otherwise, the terms "black", "blackness", and similar such terms, are to be given there broadest possible meanings, and would include among other things, the appearance of an object, color, or material: that is substantially the darkest color owing to the absence, or essential absence of, or absorption, or essential abortion of light; where the reflected refracted and transmitted spectrum(s) of light detected or observed from an object or material has no, substantially no, and essentially no light in the visible wavelengths; the colors that are considered generally black in any color space characterization scheme, including the colors that are considered generally black in L a b color space, the colors that are considered generally black in the Hunter color space, the colors that are considered generally black in the CIE color space, and the colors that are considered generally black in the CIELAB color space; any color, or object or material, that matches or substantially matches any Pantone® color that is referred to as black, including PMS 433, Black 3, Black 4, Black 5, Black 6, Black 7, Black 2 2x, Black 3 2x, Black 4 2x, Black 5 2x, Black 6 2x, Black 7 2x, 412, 419, 426, and 423; values on a Tri-stimulus Colorimeter of X=from about 0.05 to about 3.0; Y=from about 0.05 to about 3.0, and Z=from about 0.05 to about 3.0; in non glossy formulations; a CIE L a b of L=less than about 40, less than about 20, less than about 10, less than about 1, and about zero, of "a"=of any value; of "b"=of any value; and a CIE L a b of L=less than 50 and b=less than 1.0; an L value less than 30, a "b" value less than 0.5 (including negative values) and an "a" value less than 2 (including negative values); having a jetness value of about 200 $M_y$ and greater, about 250 $M_y$ and greater, 300 $M_y$ and greater, and greater; having an L=40 or less and a My of greater than about 250; having an L=40 or less and a My of greater than about 300; having a dM value of 10; having a dM value of −15; and combinations and variations of these.

As used herein, unless stated otherwise, the term "gloss" is to be given its broadest possible meaning, and would include the appearance from specular reflection. Generally the reflection at the specular angle is the greatest amount of light reflected for any specific angle. In general, glossy surfaces appear darker and more chromatic, while matte surfaces appear lighter and less chromatic.

As used herein, unless stated otherwise, the term "Jetness" is to be given its broadest possible meaning, and would include among other things, a Color independent blackness value as measured by $M_y$ (which may also be called the "blackness value"), or $M_c$, the color dependant blackness value, and $M_y$ and $M_c$ values obtained from following DIN 55979 (the entire disclosure of which is incorporated herein by reference).

As used herein, unless stated otherwise, the term "undertone," "hue" and similar such terms are to be given their broadest possible meaning, and would include among other things.

As used herein, unless stated otherwise, the terms "visual light," "visual light source," "visual spectrum" and similar such terms refers to light having a wavelength that is visible, e.g., perceptible, to the human eye, and includes light generally in the wave length of about 390 nm to about 770 nm.

As used herein, unless stated otherwise, the term "paint" is to be given its broadest possible meaning, and would include among other things, a liquid composition that after application as a thin layer to a substrate upon drying forms a thin film on that substrate, and includes all types of paints such as oil, acrylic, latex, enamels, varnish, water reducible, alkyds, epoxy, polyester-epoxy, acrylic-epoxy, polyamide-epoxy, urethane-modified alkyds, and acrylic-urethane.

As used herein, unless stated otherwise, the term "plastic" is to be given its broadest possible meaning, and would include among other things, synthetic or semi-synthetic organic polymeric materials that are capable of being molded or shaped, thermosetting, thermoforming, thermoplastic, orientable, biaxially orientable, polyolefins, polyamide, engineering plastics, textile adhesives coatings (TAC), plastic foams, styrenic alloys, acrylonitrile butadiene styrene (ABS), polyurethanes, polystyrenes, acrylics, polycarbonates (PC), epoxies, polyesters, nylon, polyethylene, high density polyethylene (HDPE), very low density polyethylene (VLDPE), low density polyethylene (LDPE), polypropylene (PP), polyvinyl chloride (PVC), polyethylene terephthalate (PET), polybutylene terephthalate (PBT), poly ether ethyl ketone (PEEK), polyether sulfone (PES), bis maleimide, and viscose (cellulose acetate).

As used herein, unless stated otherwise, the term "ink" is to be given its broadest possible meaning, and would include among other things, a colored liquid for marking or writing, toner (solid, powder, liquid, etc.) for printers and copiers, and colored solids that are used for marking materials, pigment ink, dye ink, tattoo ink, pastes, water-based, oil-based, rubber-based, and acrylic-based.

As used herein, unless stated otherwise, the term "nail polish" and similar such terms, are to be given its broadest term, and would include all types of materials, coatings and paints that can be applied to, or form a film, e.g., a thin film, on the surface of a nail, including natural human nails, synthetic "fake" nails, and animal nails.

As used herein, unless stated otherwise, the term "adhesive" is to be given its broadest possible meaning, and would include among other things, substances (e.g., liquids, solids, plastics, etc.) that are applied to the surface of materials to hold them together, a substance that when applied to a surface of a material imparts tack or stickiness to that surface, and includes all types of adhesives, such as naturally occurring, synthetic, glues, cements, paste, mucilage, rigid, semi-rigid, flexible, epoxy, urethane, methacrylate, instant adhesives, super glue, permanent, removable, and expanding.

As used herein, unless stated otherwise, the term "coating" is to be given its broadest possible meaning, and would include among other things, the act of applying a thin layer to a substrate, any material that is applied as a layer, film, or thin covering (partial or total) to a surface of a substrate, and includes inks, paints, and adhesives, powder coatings, foam coatings, liquid coatings, and includes the thin layer that is formed on the substrate, e.g. a coating.

As used herein, unless stated otherwise, the term "sparkle" is to be given its broadest possible meaning, and would include among other things, multi angle reflections simultaneously imparted from the surface facets.

As used herein, unless stated otherwise, room temperature is 25° C. And, standard temperature and pressure is 25° C. and 1 atmosphere.

Generally, the term "about" as used herein unless specified otherwise is meant to encompass a variance or range of ±10%, the experimental or instrument error associated with obtaining the stated value, and preferably the larger of these.

SUMMARY

There has been a long-standing and unfulfilled need for, improved pigments and additives for plastics, paints, inks, coatings and adhesives, as well as a continued need for improved formulations for these coatings and materials. The present inventions, among other things, solve these needs by providing the compositions of matter, materials, articles of manufacture, devices and processes taught, disclosed and claimed herein.

There is provided a coating formulation having: a first material and a second material; wherein the first material defines a first material weight percent of the coating formulation and the second material defines a second material weight percent of the coating formulation; wherein the second material is a black polymer derived ceramic material having from about 30 weight % to about 60 weight % silicon, from about 5 weight % to about 40 weight % oxygen, and from about 3 weight % to about 35 weight % carbon; and wherein the first material weight percent is larger than the second material weight percent.

There is further provided the pigments, coatings, coating formulations and materials that have one or more of the following features: wherein 20 weight % to 80 weight % of the carbon is free carbon; wherein 20 weight % to 80 weight % of the carbon is silicon-bound-carbon; wherein the formulation is selected from the group consisting of paint, powder coat, adhesive, nail polish, and ink; wherein the black polymer derived ceramic material has a particle size of less than about 1.5 µm; wherein the black polymer derived ceramic material has a particle size $D_{50}$ of from about 1 µm to about 0.1 µm; wherein the coating defines a blackness selected from the group consisting of: PMS 433, Black 3, Black 3, Black 4, Black 5, Black 6, Black 7, Black 2 2x, Black 3 2x, Black 4 2x, Black 5 2x, Black 6 2x, and Black 7 2x; wherein the coating defines a blackness selected from the group consisting of: Tri-stimulus Colorimeter of X from about 0.05 to about 3.0, Y from about 0.05 to about 3.0, and Z from about 0.05 to about 3.0; a CIE L a b of L of less than about 40; a CIE L a b of L of less about 20; a CIE L a b of L of less than 50, b of less than 1.0 and a of less than 2; and a jetness value of at least about 200 $M_y$; wherein the formulation is essentially free of heavy metals; wherein the formulation has less than about 100 ppm of heavy metals; wherein the formulation has less than about 10 ppm heavy metals; wherein the formulation has less than about 1 ppm heavy metals; wherein the formulation has less than about 0.1 ppm heavy metals; wherein the coating is essentially free of heavy metals; wherein the coating has less than about 100 ppm of heavy metals; wherein the coating has less than about 10 ppm heavy metals; wherein the coating has less than about 1 ppm heavy metals; wherein the coating has less than about 0.1 ppm heavy metals; wherein the pigment has less than about 10 ppm heavy metals, less than about 1 ppm heavy metals, and less than about 0.1 ppm heavy metals; and wherein the heavy metals are Cr and Mn.

Yet further there is provided a paint formulation having: a resin, a solvent, and a polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

There is further provided the pigments, coatings, coating formulations and materials that have one or more of the following features: wherein the polymer derived ceramic pigment has a primary particle $D_{50}$ size of from about 0.1 µm to about 2.0 µm; wherein the polymer derived ceramic pigment is loaded at from about 1.5 pounds/gallon to about 10 pounds/gallon; wherein the resin is selected from the group of resins consisting of thermoplastic acrylic polyols, Bisphenol A diglycidal ether, silicone, oil based, and water-reducible acrylic; wherein the formulation has less than about 0.01 ppm of heavy metals; wherein the formulation has less than about 0.1 ppm of heavy metals; wherein the formulation has less than about 1 ppm of heavy metals, and the paint formulation is a very high temperature coating, wherein the paint formulation is thermally stable to greater than 700° C.; wherein the formulation has less than about 10 ppm of heavy metals, and the paint formulation is a very high temperature coating; wherein the paint formulation is a very high temperature coating, and wherein the paint formulation is thermally stable to greater than 1000° C.; wherein the first material has a system selected from the group of systems consisting of acrylics, lacquers, alkyds, latex, polyurethane, phenolics, epoxies and waterborne; wherein the first material has a material selected from the group consisting of HDPE, LDPE, PP, Acrylic, Epoxy, Linseed Oil, PU, PUR, EPDM, SBR, PVC, water based acrylic emulsions, ABS, SAN, SEBS, SBS, PVDF, PVDC, PMMA, PES, PET, NBR, PTFE, siloxanes, polyisoprene and natural rubbers; wherein the coating formulation is a paint formulation selected from the group consisting of oil, acrylic, latex, enamel, varnish, water reducible, alkyd, epoxy, polyester-epoxy, acrylic-epoxy, polyamide-epoxy, urethane-modified alkyd, and acrylic-urethane; and wherein the coating has a coating selected from the group consisting of industrial coatings, residential coatings, furnace coatings, engine component coatings, pipe coatings, and oil field coatings.

Yet moreover there is provided an ink formulation having: a first material and a black polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Furthermore there is provided a nail polish formulation, having a carrier material and a black polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Additionally there is provided a plastic material, having a first material and a second material, wherein the first material is a plastic and makes up at least 50% of the total weight of the plastic material, and the second material is a black polymer derived ceramic material having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

There is further provided the pigments, coatings, coating formulations and materials that have one or more of the following features: wherein the plastic is selected from the group consisting of HDPE, LDPE, PP, Acrylic, Epoxy, Linseed Oil, PU, PUR, EPDM, SBR, PVC, water based acrylic emulsions, ABS, SAN, SEBS, SBS, PVDF, PVDC, PMMA, PES, PET, NBR, PTFE, siloxanes, polyisoprene and natural rubbers; wherein the plastic is selected from the group consisting of thermosetting, thermoforming, thermoplastic, orientable, biaxially orientable, polyolefins, polyamide, engineering plastics, textile adhesives coatings (TAC) and plastic foams; wherein the plastic is selected from the group consisting of styrenic alloys, acrylonitrile butadiene styrene (ABS), polyurethanes, polystyrenes, acrylics, polycarbonates (PC), epoxies, polyesters, nylon, polyethylene, high density polyethylene (HDPE), very low density polyethylene (VLDPE); and wherein the plastic is selected from the group consisting of low density polyethylene (LDPE), polypropylene (PP), polyvinyl chloride (PVC), polyethylene terephthalate (PET), polybutylene terephthalate (PBT), poly ether ethyl ketone (PEEK), polyether sulfone (PES), bis maleimide, and viscose (cellulose acetate).

Still additionally there is provided a paint having: a resin and a polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Yet further there is provided an ink having: a carrier material and a black polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Moreover there is provided a nail polish formulation having: a carrier material and a black polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Yet additionally there is provided an adhesive having: a carrier material and a black polymer derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

Further there is provided a coating having: a first material and a second material; wherein the first material defines a first material weight percent of the coating formulation and the second material has a second material weight percent of the total coating formulation; and wherein the second material is a black polymer derived ceramic material having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent.

There is further provided the pigments, coatings, coating formulations and materials that have one or more of the following features: wherein the coating is a paint; wherein the coating is a powder coat; wherein the black polymer derived ceramic material has a particle size of less than about 1.5 µm; wherein the coating defines a blackness selected from the group consisting of: PMS 433, Black 3, Black 3, Black 4, Black 5, Black 6, Black 7, Black 2 2x, Black 3 2x, Black 4 2x, Black 5 2x, Black 6 2x, and Black 7 2x; wherein the coating defines a blackness selected from the group consisting of: Tri-stimulus Colorimeter of X from about 0.05 to about 3.0, Y from about 0.05 to about 3.0, and Z from about 0.05 to about 3.0; a CIE L a b of L of less than about 40; a CIE L a b of L of less about 20; a CIE L a b of L of less than 50, b of less than 1.0 and a of less than 2; and a jetness value of at least about 200 $M_y$; and wherein the paint is a paint selected from the group consisting of oil, acrylic, latex, enamel, varnish, water reducible, alkyd, epoxy, polyester-epoxy, acrylic-epoxy, polyamide-epoxy, urethane-modified alkyd, and acrylic-urethane; wherein the coating is essentially free of heavy metals; wherein the coating has less than about 10 ppm of heavy metals.

Additionally there is provided a paint having a resin and a polymer derived pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

There is further provided the pigments, coatings, coating formulations and materials that have one or more of the following features: wherein the first material has a material selected from the group of materials consisting of acrylics, lacquers, alkyds, latex, polyurethane, phenolics, epoxies and waterborne; wherein the coating is a paint selected from the group consisting of oil, acrylic, latex, enamel, varnish, water reducible, alkyd, epoxy, polyester-epoxy, acrylic-epoxy, polyamide-epoxy, urethane-modified alkyd, and acrylic-urethane; wherein the black polymer derived ceramic material has about 40 weight % to about 50 weight % silicon, and wherein about 25 weight % to about 40 weight % of the carbon is silicon-bound-carbon; wherein the black polymer derived ceramic material has about 40 weight % to about 50 weight % silicon, and wherein about 55 weight % to about 75 weight % of the carbon is free carbon; wherein the black polymer derived ceramic material has about 20 weight % to about 30 weight % oxygen, and wherein about 25 weight % to about 40 weight % of the carbon is silicon-bound-carbon; wherein the black polymer derived ceramic material has about 20 weight % to about 30 weight % oxygen, and wherein about 55 weight % to about 75 weight % of the carbon is free carbon; wherein the black polymer derived ceramic material has about 20 weight % to about 30 weight % carbon, and wherein about 25 weight % to about 40 weight % of the carbon is silicon-bound-carbon; wherein the black polymer derived ceramic material has about 20 weight % to about 30 weight % carbon, and wherein about 55 weight % to about 75 weight % of the carbon is free carbon; wherein the black polymer derived ceramic material has about 40 weight % to about 50 weight % silicon, and wherein about 25 weight % to about 40 weight % of the carbon is silicon-bound-carbon; wherein the black polymer derived ceramic material has about 40 weight % to about 50 weight % silicon, and wherein about 55 weight % to about 75 weight % of the carbon is free carbon; wherein the black polymer derived ceramic material has about 20 weight % to about 30 weight % oxygen, and wherein about 25 weight % to about 40 weight % of the carbon is silicon-bound-carbon; wherein the black polymer derived ceramic material has about 20 weight % to about 30 weight % oxygen, and wherein about 55 weight % to about 75 weight % of the carbon is free carbon; wherein the black polymer derived ceramic material has about 20 weight % to about 30 weight % carbon, and wherein about 25 weight % to about 40 weight % of the carbon is silicon-bound-carbon; and wherein the black polymer derived ceramic material has about 20 weight % to about 30 weight % carbon, and wherein about 55 weight % to about 75 weight % of the carbon is free carbon.

Furthermore there is provided a black polysilocarb derived ceramic pigment having from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon and 80 weight % to about 20 weight % of the carbon is free carbon.

There is further provided the pigments, coatings, coating formulations and materials that have one or more of the following features: wherein the pigment is a UV absorber; wherein the pigment has an absorption coefficient of greater than 500 dB/cm/(g/100 g); wherein the pigment has an absorption coefficient of greater than 500 dB/cm/(g/100 g); wherein the pigment has an absorption coefficient of greater than 1,000 dB/cm/(g/100 g); wherein the pigment has an absorption coefficient of greater than 5,000 dB/cm/(g/100 g); wherein the pigment has an absorption coefficient of greater than 10,000 dB/cm/(g/100 g); wherein the pigment has an agglomerate of primary pigment particles; wherein the agglomerate has a size $D_{50}$ of at least about 10 µm; wherein the primary pigment particles have a size $D_{50}$ of less than about 1 µm; wherein the agglomerate has a strength $A_s$ and the primary particle has a strength $PP_s$ and $PP_s$ is at least 100 times greater than $A_s$; wherein the agglomerate has a strength $A_s$ and the primary particle has a strength $PP_s$ and $PP_s$ is at least 500 times greater than $A_s$; wherein the agglomerate has a strength $A_s$ and the primary particle has a strength $PP_s$ and $PP_s$ is at least 1,000 times greater than $A_s$; wherein the pigment has an oil absorption of less than about 50 g/100 g; wherein the pigment has an oil absorption of less than about 20 g/100 g; wherein the polymer derived ceramic pigment has a primary particle $D_{50}$ size of from about 0.1 µm to about 1.5 µm; wherein the polymer derived ceramic pigment has a primary particle $D_{50}$ size of greater than about 0.1 µm; wherein the polymer derived ceramic pigment has a primary particle $D_{50}$ size of less than about 10.0 µm; wherein the polymer derived ceramic pigment has a primary particle $D_{50}$ size of from about 0.1 µm to about 3.0 µm; wherein the polymer derived ceramic pigment has a primary particle $D_{50}$ size of from about 1 µm to about 5.0 µm; wherein the pigment is microwave safe; wherein the pigment is non-conductive; wherein the pigment is hydrophilic; and wherein the pigment is hydrophobic.

DESCRIPTION OF THE PREFERRED EMBODIMENTS

Figure 1:
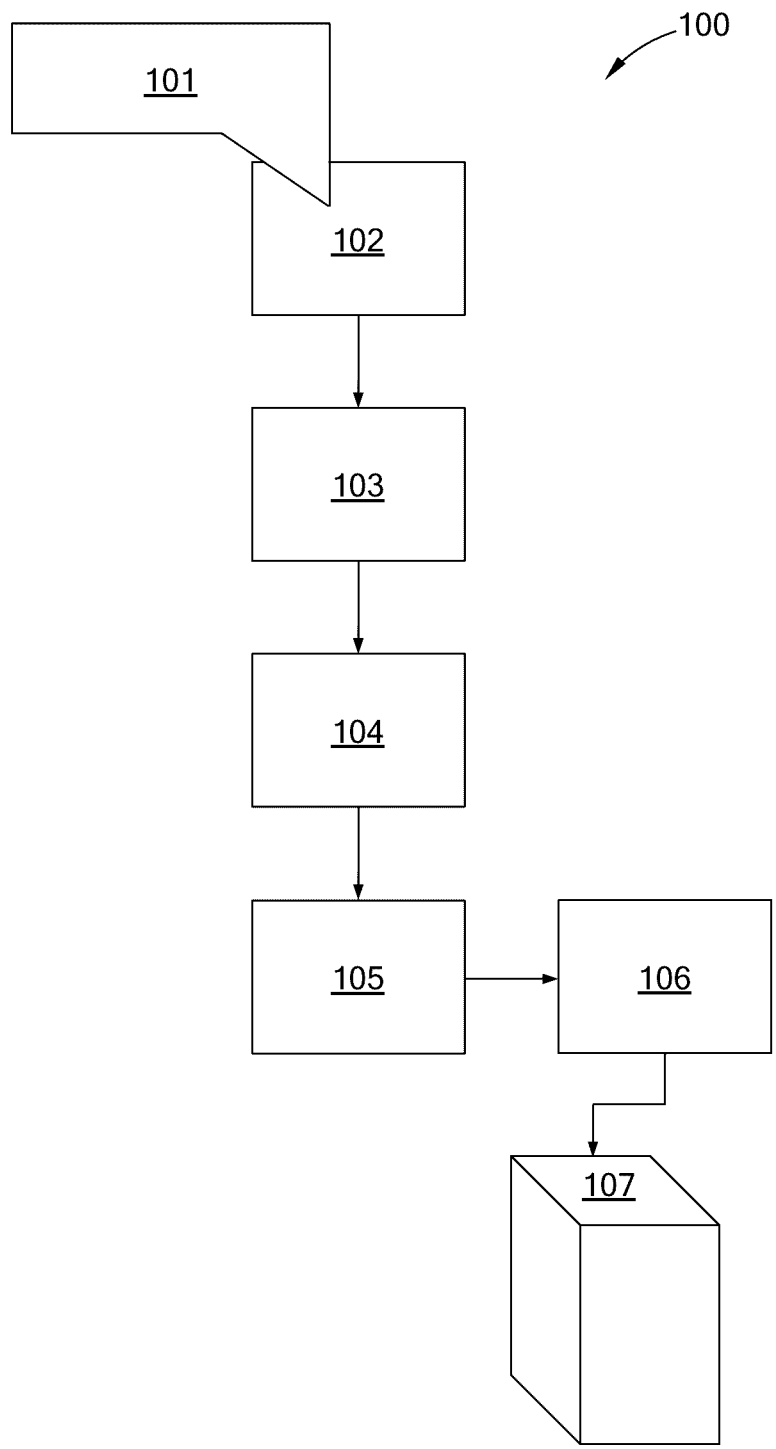
FIG. 1 is a schematic flow diagram of an embodiment of a system in accordance with the present inventions.

In general the present inventions relate to ceramic black materials for use as, or in, colorants, inks, pigments, dyes, additives and formulations utilizing these black materials. Embodiments of the present inventions, among other things, relate to ceramic materials having blackness, black color, and which are black; starting compositions for these ceramic materials, and methods of making these ceramic materials; and formulations, compositions, materials that utilize or have these ceramic materials. These various embodiments of the present inventions, in particular, relate to, or utilize, such ceramic black materials that are polymer derived ceramics. Embodiments of the present inventions also relate to black ceramics having silicon, oxygen and carbon, and methods of making these ceramics; formulations utilizing these black ceramics; and devices, structures and apparatus that have or utilize these formulations. Embodiments of the present invention in general include plastics, paints, inks, coatings, formulations, liquids and adhesives containing ceramic black materials, preferably polymer derived black ceramic materials, and more preferably polysilocarb polymer derived ceramic materials.

Polymer derived ceramics (PDC) are ceramic materials that are derived from, e.g., obtained by, the pyrolysis of polymeric materials. These materials are typically in a solid or semi-solid state that is obtained by curing an initial liquid polymeric precursor, e.g., PDC precursor, PDC precursor formulation, precursor batch, and precursor. The cured, but unpyrolized, polymer derived material can be referred to as a preform, a PDC preform, the cured material, and similar such terms. Polymer derived ceramics may be derived from many different kinds of precursor formulations, e.g., starting materials, starting formulations. PDCs may be made of, or derived from, carbosilane or polycarbosilane (Si—C), silane or polysilane (Si—Si), silazane or polysilazane (Si—N—Si), silicon carbide (SiC), carbosilazane or polycarbosilazane (Si—N—Si—C—Si), siloxane or polysiloxanes (Si—O), to name a few.

A preferred PDC is "polysilocarb", e.g., material containing silicon (Si), oxygen (O) and carbon (C). Polysilocarb materials may also contain other elements. Polysilocarb materials can be made from one or more polysilocarb precursor formulation or precursor formulation. The polysilocarb precursor formulations can contain, for example, one or more functionalized silicon polymers, other polymers, non-silicon based cross linking agents, monomers, as well as, potentially other ingredients, such as for example, inhibitors, catalysts, initiators, modifiers, dopants, fillers, reinforcers and combinations and variations of these and other materials and additives. Silicon oxycarbide materials, SiOC compositions, and similar such terms, unless specifically stated otherwise, refer to polysilocarb materials, and would include liquid materials, solid uncured materials, cured materials, and ceramic materials.

Examples of PDCs, PDC formulations and starting materials, are found in U.S. patent application Ser. Nos. 14/212,986, 14/268,150, 14/324,056, 14/514,257, 61/946,598, and 62/055,397, US Patent Publication No 2008/0095942, 2008/0093185, 2007/0292690, 2006/0230476, 2006/0069176, 2006/0004169, and 2005/0276961, and U.S. Pat. Nos. 5,153,295, 4,657,991, 7,714,092, 7,087,656 and 8,742,008, and 8,119,057, the entire disclosures of each of which are incorporated herein by reference.

Turning to FIG. 1 there is provided a process flow chart 100 for an embodiment having several embodiments of the present processes and systems. Thus, there is a precursor make-up segment 101, where the PDC precursor formulations are prepared. There is a forming segment 102 where the PDC precursor is formed into a shape, e.g., bead, slab, and particle. There is a curing segment 103, where the PDC precursor is cured to a cured material, which is substantially solid, and preferably a solid. There is a pyrolysis segment 104 where the cured material is converted to a ceramic, e.g., a PDC, which preferably is a SiOC. There is a post-processing segment 105, where the ceramic is further processed, e.g., washing, grinding, agglomeration, milling, cycloning, sieving, etc. There is a formulation segment 106 where the PDC is processed into a material formulation (e.g., paint, plastic, ink, coating and adhesive), containing the PDC, i.e., a PDC containing material formulation. PDC containing material formulations include, among other things, PDC paints, PDC plastics, PDC inks, PDC adhesives, and PDC coatings. There is an application segment 107, where a PDC containing material formulation is applied to a substrate, e.g., a refrigerator, vehicle, appliance or other items, and components of such items.

The precursor make-up segment can be any of the systems, processes and materials disclosed and taught in this specification, as well as, those disclosed and taught in U.S. patent application Ser. Nos. 14/212,986, 14/268,150, 14/324,056, 14/514,257, 61/946,598 and 62/055,397 and 62/106,094, the entire disclosure of each of which are incorporated herein by reference.

The forming segment can be any of the systems, processes and materials disclosed and taught in this specification, as well as, those disclosed and taught in U.S. patent application Ser. Nos. 14/212,986, 14/268,150, 14/324,056, 14/514,257, 61/946,598 and 62/055,397 and 62/106,094, the entire disclosure of each of which are incorporated herein by reference.

The curing segment can be any of the systems, processes and materials disclosed and taught in this specification, as well as, those disclosed and taught in U.S. patent application Ser. Nos. 14/212,986, 14/268,150, 14/324,056, 14/514,257, 61/946,598 and 62/055,397 and 62/106,094, the entire disclosure of each of which are incorporated herein by reference.

The pyrolizing segment can be any of the systems, processes and materials disclosed and taught in this specification, as well as, those disclosed and taught in U.S. patent application Ser. Nos. 14/212,986, 14/268,150, 14/324,056, 14/514,257, 61/946,598 and 62/055,397 and 62/106,094, the entire disclosure of each of which are incorporated herein by reference. By way of example, furnaces can that can be used for the pyrolizing segment include, among others: RF furnaces, Microwave furnaces, pressure furnaces, fluid bed furnaces, box furnaces, tube furnaces, crystal-growth furnaces, arc melt furnaces, induction furnaces, kilns, $MoSi_2$ heating element furnaces, gas-fired furnaces, carbon furnaces, and vacuum furnaces.

The post-processing segment can involve any type of further processing activities to enhance, effect, or modify the performance, handleability, processability, features, size, surface properties, and combinations and variations of these. Thus, for example, the post-processing step can involve a grinding step in which the PDC is reduced in size to diameters of less than about 10 μm, less than about 5 μm, less than about 1 μm, less than about 0.5 μm, and less than about 0.1 μm. The PDC can be ground, for example, by the use of a ball mill, an attrition mill, a rotor stator mill, a hammer mill, a jet-mill, a roller mill, a bead mill, a media mill, a grinder, a homogenizer, a two-plate mill, a dough mixer, and other types of grinding, milling and processing apparatus. The post-processing segment can involve, for example, an agglomeration, where smaller PDC particles are combined to form larger particles, preferably agglomerated particles having diameters of at least about 2 μm, at least about 2.5 µm, greater than 2.5 µm, at least about 3 µm, at least about 5 µm, at least about 10 µm, greater than 10 µm, and greater than 12 µm. Preferably, the agglomerated particles are sufficiently bound, or held together, to prevent the particles from falling off, e.g., separating from, the agglomeration during handling, shipping, storage, and processing, e.g., "handling strength." More preferably, the strength of the agglomerations is only slightly greater than the handling strength, and in this manner can readily be broken apart into the smaller particles for use in a PDC material formulation. For example, the agglomeration can have a strength, e.g., crush strength, that is less than about 1/2000 of the strength of the smaller particles, e.g., primary particles, that form the agglomeration, less than about 1/500 of the strength of the smaller particles, less than about 1/75 of the strength of the smaller particles, and less than 1/2 of the strength of the smaller particles. The agglomeration can, for example, be formed by using spray drying techniques. Suitable binders, including for example sizing agents, for use in spray drying techniques include for example: dispersants, surfactants, soaps, copolymers, starches, natural and synthetic polymers and saccharides, lipids, fatty acids, petroleum-derived polymers and oligomers. Sodium alginate, corn starch, potato starch, and other naturally derived starches, fructoses, sucroses, dextroses and other naturally or synthetically derived saccharides and sugars, polylactic acid and other naturally derived polymers, cellulosic byproducts, carrageenan and other natural products, poly vinyl acetate and other water-soluble polymers, wetting and dispersing agents such as polyacrylates, polyethylene oxides, polypropylene oxides, and copolymers containing them. Parrafins and other waxes, other petrochemical derivatives and petroleum based polymers. Surfactants such as Tween, Span, Brij, and other types of surfactants; Stearates, oleates, and other modified oils; linear copolymers, branched copolymers, star polymers and copolymers, hyperbranched polymers and copolymers, comb-like polymers, and combinations and variations of these.

The amount of binder used to PDC can range from about 0.01% to 5%, about 0.1% to about 2%, and preferably less than about 1% and less than about 0.5%. Agglomerates can also be formed by batch evaporation and casting, thin film evaporation, wiped-film evaporation, tray drying, oven drying, freeze drying, and other suitable evaporation methods, aggregation techniques such as sedimentation, solvent exchange and coagulation, pin mixing, filtration, and others, preferably combined with a drying technique, and combinations and variations of these. Further, processing may involve the application of a surface treatment, wash, or coating to the surface of the PDC particles to provide predetermined features to the PDCs, such as for example, enhanced antistatic, wettability, material formulation compatibility, mixability, etc. It should be noted that while surface treatments are contemplated by the present inventions to further enhance, e.g., specialize the PDC particles for a particular purpose; an advantage of the present inventions is the feature that they are more readily mixed, added, or compiled into material formations, e.g., paints, plastics, inks, coating and adhesives, than the prior art black pigments, e.g., carbon black ((ASTM Color Index) CI Black 1,6,7) or graphite (CI Black 10) or metal oxides and mixed metal oxides, including but not limited to iron oxides (CI Black 11) and Manganese Iron oxide (CI Black 26) or Iron Manganese oxide (CI Black 33), Manganese oxide (CI Black 14), Copper oxide (CI Black 13), Copper Manganese Iron oxide (CI Black 26) or Copper Chrome oxide (CI Black 28), and pigment made by ashing organic matter (CI Black 8, 9) which typically for many applications require surface treatments. Thus, an advantage of the present inventions, among other things, is the ability to use untreated PDC particles, e.g., no surface treatments, in materials formulation.

In the formulation segment, the making of the PDC material formulation takes place. Thus, for example, the PDC ceramic is mixed into, added to, or otherwise combined with the materials used to make up the material formulation. Generally, an agglomerate easily breaks down into its primary particles, e.g., the primary party state; and the primary particles are uniformly and smoothly distributed or suspended in the primary formulation material, which can be obtained in less than 60 minutes of mixing, less than 30 minutes of mixing and quicker. Typically, the PDC ceramic is much more easily mixed into the material formulation than carbon black to a fully dispersed state. For example, and by way of illustration, PDC ceramic can be easily and quickly mixed within 10 minutes into a vessel in which a simple 3 blade stirrer is mixing at 1,000 rpm tip speed. The resin, PDC Ceramic mixture will be fully dispersed which is illustrated by a reading of greater than 7 on the Hegman gauge. The Hegman gauge is a calibrated device to quickly show how fine a dispersion is made. A carbon black or oxide black pigment mixed into the resin in the same manner would produce a Hegman reading of less than 1 which indicates very large particles still in the resin, because these pigments require high energy milling to break up the aggregates in the 'as supplied' pigment. Generally, the PDC ceramic can be mixed into, added to, or otherwise combined with the material formulation in the same manner, using the same or existing equipment, that are present for use with other black pigments or colorants. Preferably, for many applications less expensive, quicker, more efficient equipment and much less expensive processes than are needed for carbon black can be used with the PDC particles.

In the application segment the PDC containing material formulation is applied to an end product, or a component that may be used in an end product. The PDC containing material formulation can typically, and preferably, be applied using the same types of techniques that are used for carbon black based formulations, e.g., brush, spray, dip, etc. Moreover, the PDC containing material formulations have applications, and the ability to be applied, in manners that could not be accomplished with a similar carbon black based formulation.

It should be understood that the various segments of the embodiment of FIG. 1 can be combined (e.g., a single piece of equipment could perform one of more of the operations of different segments, such as curing and pyrolizing), conducted serially, conducted in parallel, conducted multiple times, omitted (e.g., post-processing many not be necessary or required), conducted in a step wise or batch process (included where the segments are at different locations, separated by time, e.g., a few hours, a few days, months or longer, and both), conducted continuously, and in different orders and combinations and variations of these. Thus, for example the post-processing segment of grinding can be performed on the cured material prior to pyrolysis, and can also be performed on both the cured and pyrolized materials.

Figure 2A:
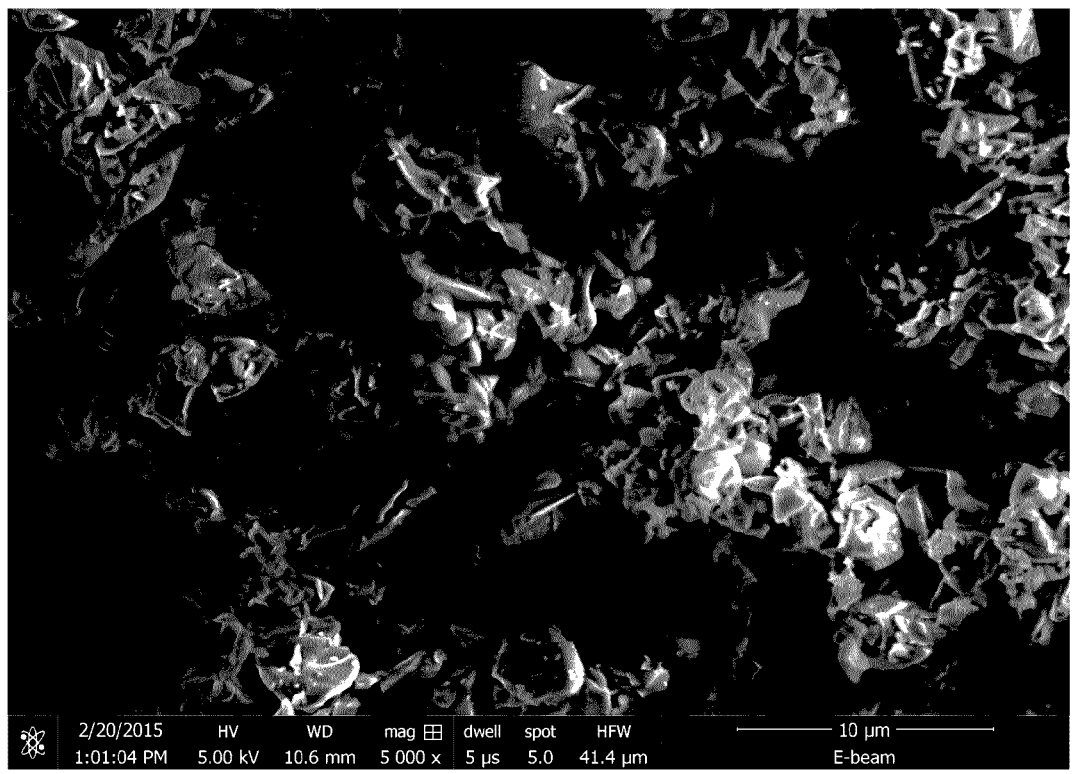
FIG. 2A is a scanning electron photomicrograph (SEPM) of an embodiment of a polysilocarb derived ceramic pigment. SEPM legend bar—HV 5.00 kV, WD 10.6 mm, magnification 5,000×, dwell 5 µs, spot 5.0, HFW 41.4 µm.
Figure 2B:
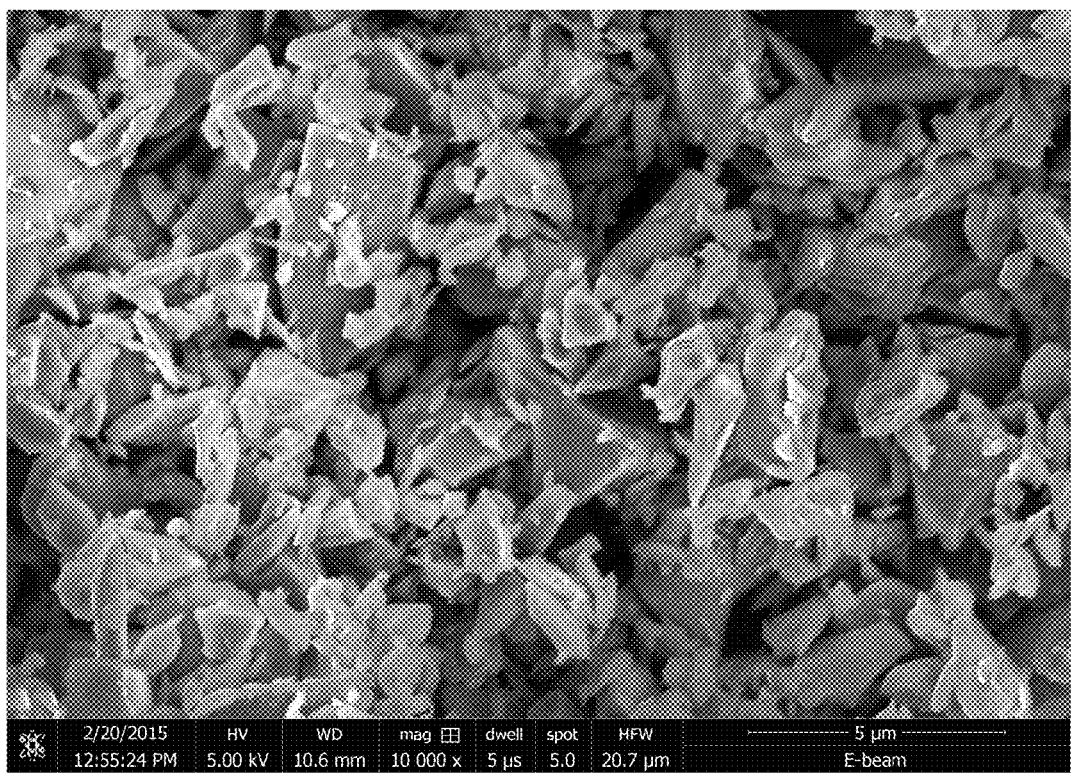
FIG. 2B is a SEPM of an embodiment of a polysilocarb derived ceramic pigment. SEPM legend bar—HV 5.00 kV, WD 10.6 mm, magnification 10,000×, dwell 5 µs, spot 5.0, HFW 20.7 µm.
Figure 3A:
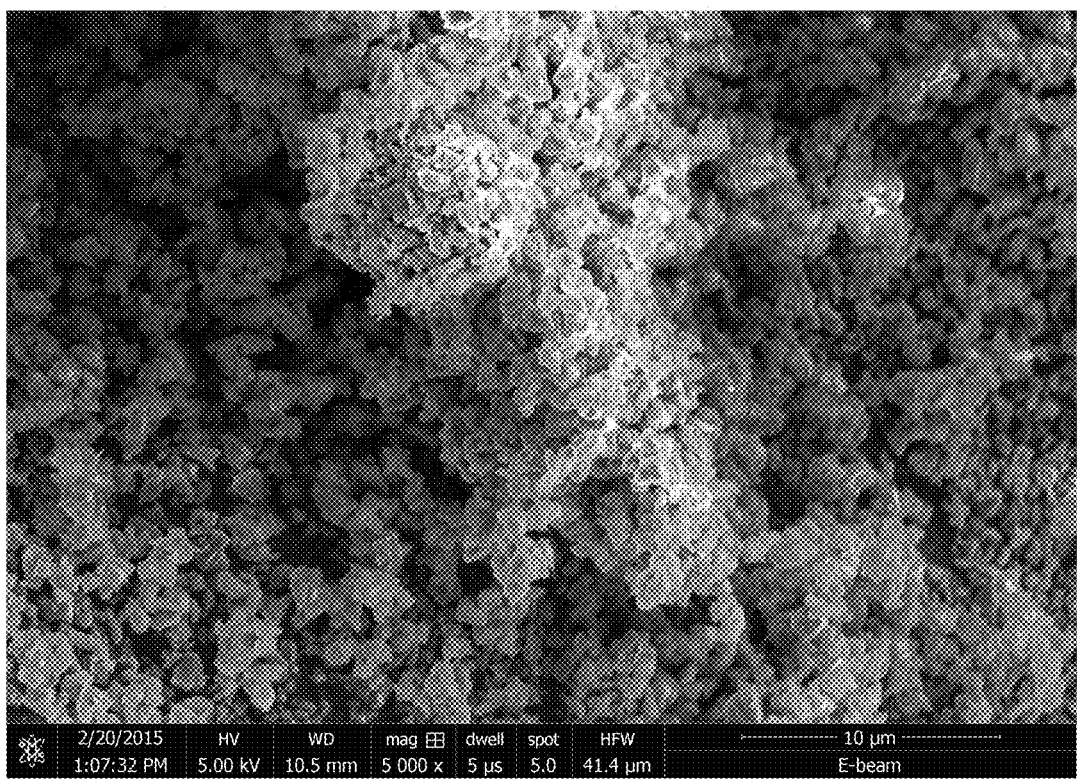
FIG. 3A is a SEPM of an embodiment of a polysilocarb derived ceramic pigment. SEPM legend bar—HV 5.00 kV, WD 10.5 mm, magnification 5,000×, dwell 5 µs, spot 5.0, HFW 41.4 µm.
Figure 3B:
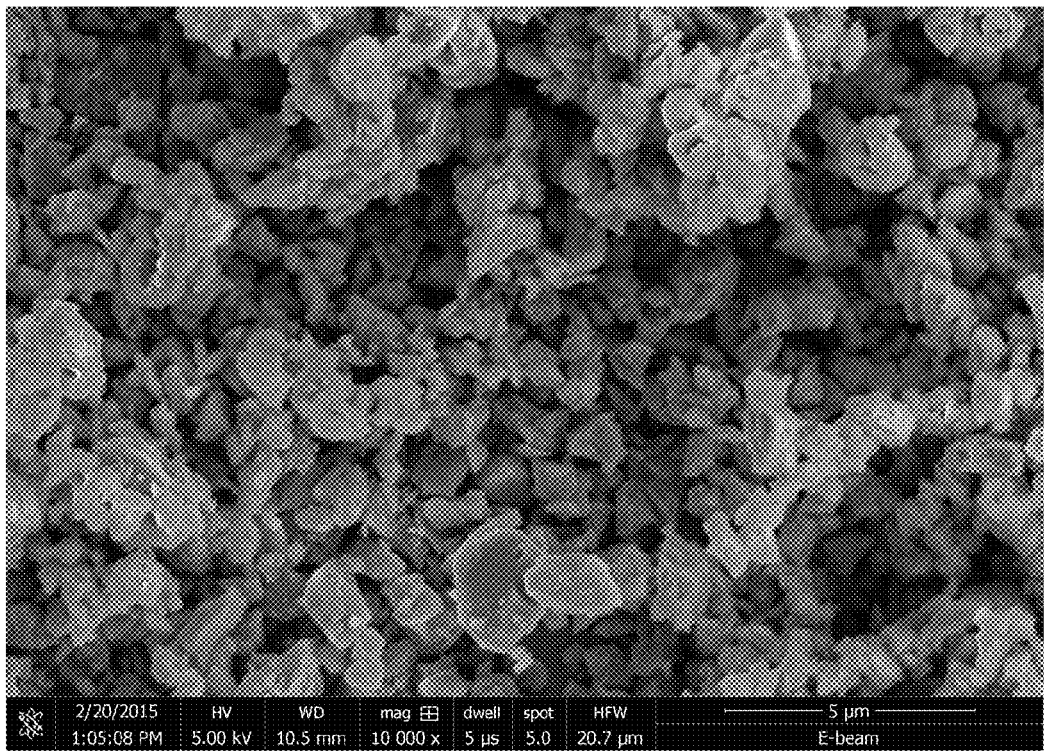
FIG. 3B is a SEPM of an embodiment of a polysilocarb derived ceramic pigment. SEPM legend bar—HV 5.00 kV, WD 10.5 mm, magnification 10,000×, dwell 5 µs, spot 5.0, HFW 20.7 µm.

FIGS. 2A and 2B, are SEPMs of an embodiment of a polysilocarb derived ceramic pigment having a primary particle size of 3 µm $D_{50}$, that was made by curing and pyrolizing the polysilocarb precursor formulation into a monolithic block, and then breaking down that block into primary particles. FIGS. 3A and 3B are SEPMs of agglomerates formed by spray drying 0.5 µm $D_{50}$ primary particles, which were obtained by further milling of the 3.0 µm primary particles shown in FIGS. 2A and 2B.

Figure 4A:
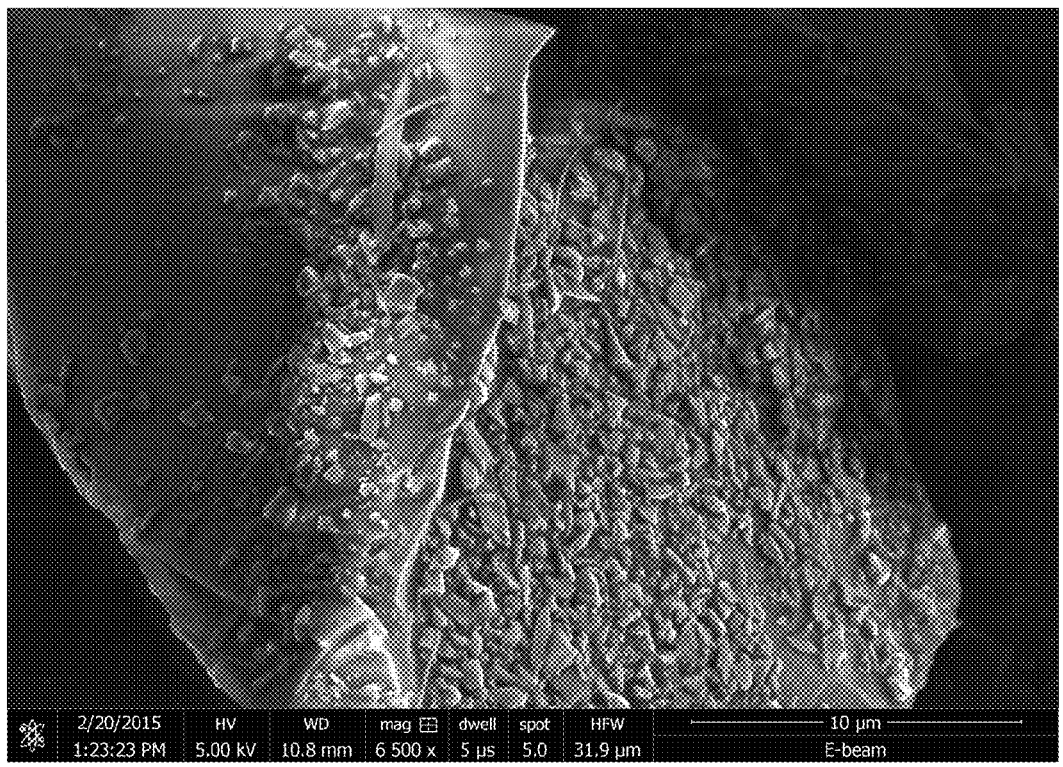
FIG. 4A is a SEPM of an embodiment of a polysilocarb derived ceramic pigment. SEPM legend bar—HV 5.00 kV, WD 10.8 mm, magnification 6,500×, dwell 5 µs, spot 5.0, HFW 31.9 µm.
Figure 4B:
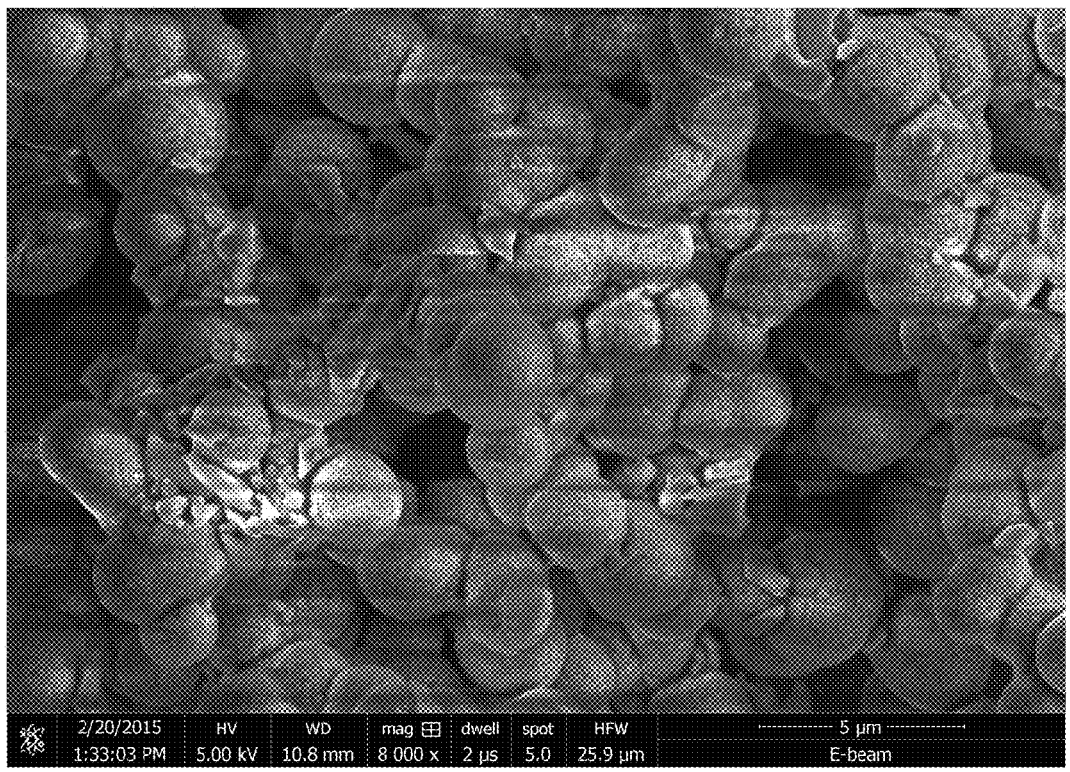
FIG. 4B is a SEPM of an embodiment of a polysilocarb derived ceramic pigment. SEPM legend bar—HV 5.00 kV, WD 10.8 mm, magnification 8,000×, dwell 2 µs, spot 5.0, HFW 25.9 µm.
Figure 4C:
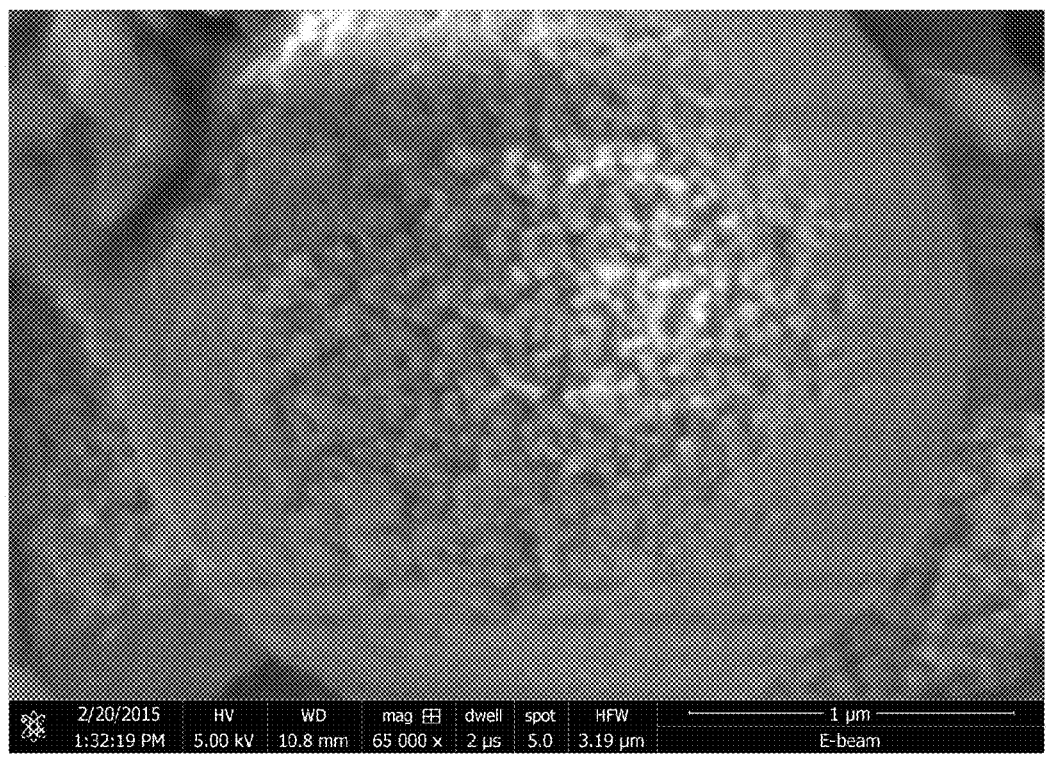
FIG. 4C is a SEPM of an embodiment of a polysilocarb derived ceramic pigment. SEPM legend bar—HV 5.00 kV, WD 10.8 mm, magnification 65,000×, dwell 5 µs, spot 5.0, HFW 31.9 µm.
Figure 5A:
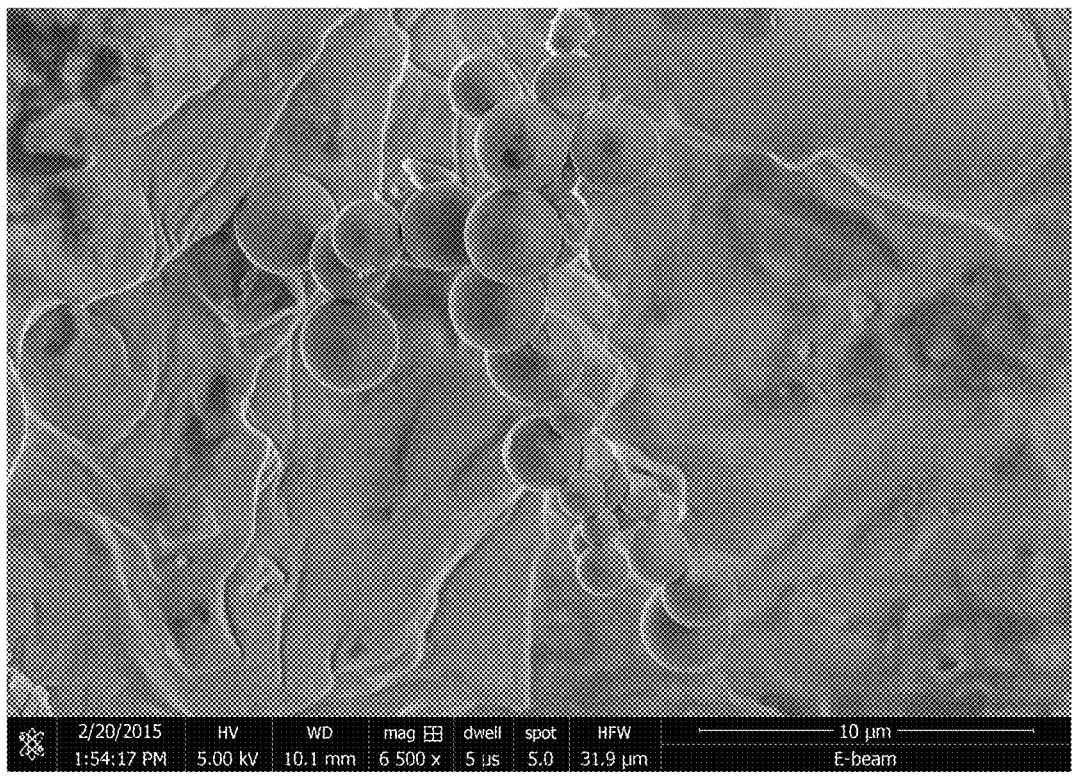
FIG. 5A is a SEPM of an embodiment of a polysilocarb derived ceramic pigment. SEPM legend bar—HV 5.00 kV, WD 10.1 mm, magnification 6,500×, dwell 5 µs, spot 5.0, HFW 31.9 µm.
Figure 5B:
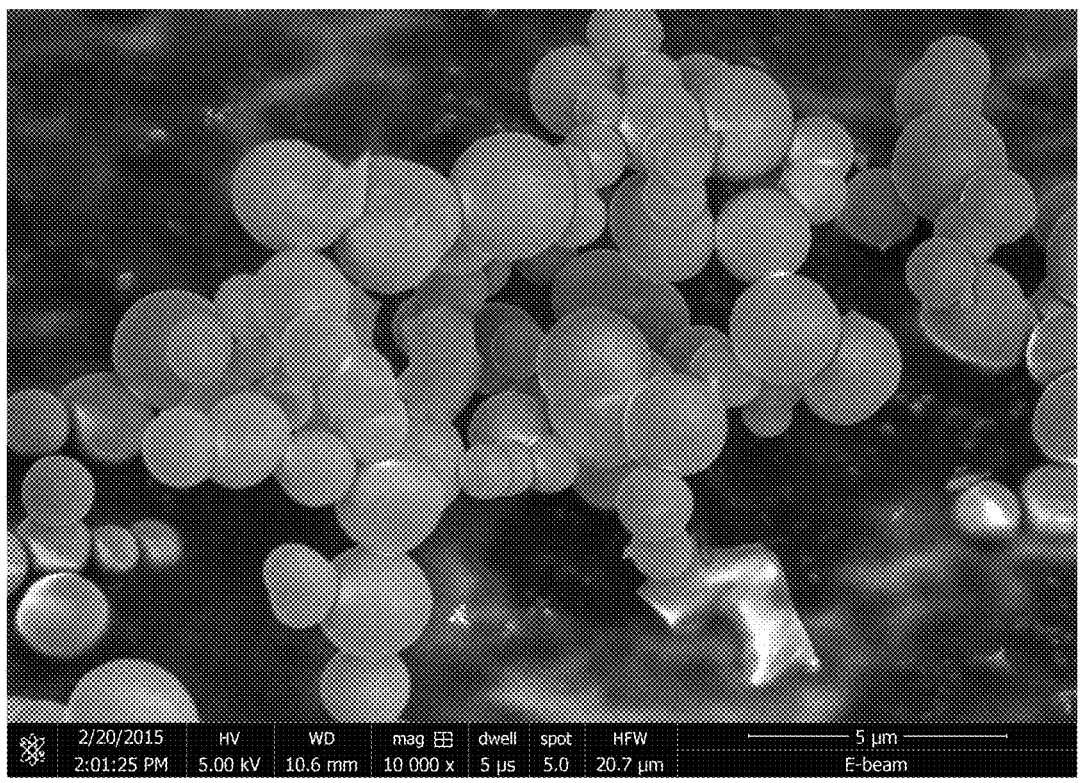
FIG. 5B is a SEPM of an embodiment of a polysilocarb derived ceramic pigment. SEPM legend bar—HV 5.00 kV, WD 10.6 mm, magnification 10,000×, dwell 5 µs, spot 5.0, HFW 20.7 µm.
Figure 5C:
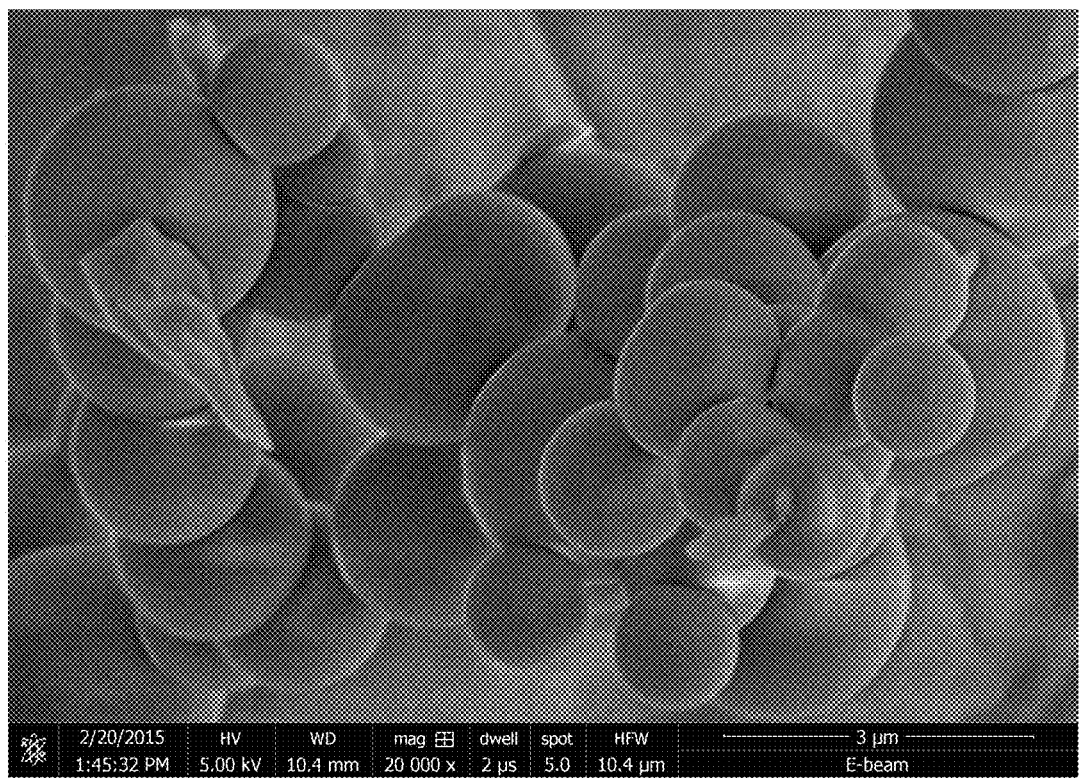
FIG. 5C is a SEPM of an embodiment of a polysilocarb derived ceramic pigment. SEPM legend bar—HV 5.00 kV, WD 10.4 mm, magnification 20,000×, dwell 2 µs, spot 5.0, HFW 10.4 µm.

FIGS. 4A, 4B and 4C, are SEPMs of 1.5 µm $D_{50}$ primary particles of an embodiment of a polysilocarb derived ceramic pigment, that were formed by a liquid-liquid system. (Liquid-liquid systems are described and set forth in detail in U.S. Patent Application Ser. No. 62/106,094, the entire disclosure of which is incorporated herein by reference) and generally involve the formation of a drop of precursor material in another liquid, and would include for example solution polymerization type systems, emulsion polymerization type systems, nano-emulsion formation type systems, and the like.) FIGS. 5A and 5B are SEPMs of the primary particles of FIGS. 4A and 4B that have been further milled down to 0.9 µm $D_{50}$.

An embodiment of a polysilocarb ceramic pigment is a colorant suitable and advantageous in multiple fields such as industrial, architectural, marine and automotive systems. The polysilocarb ceramic pigment can preferably easily disperses into acrylics, lacquers, alkyds, latex, Polyurethane, phenolics, epoxies and waterborne systems providing a durable, uniform coating and pleasant aesthetics in all types of finishes, e.g., matte and gloss.

The polysilocarb ceramic pigment can preferably be low dusting. The polysilocarb ceramic pigment does not typically accumulate charge, it is easy to clean up, and does not cling to surfaces. The polysilocarb ceramic pigment is considerably easier to clean up, and control dusting than typical carbon black. It is theorized that the typical carbon black's strong hydrophobicity, light particle weight, and very small particle size (e.g., 50 nm to 200 nm), among other things, makes carbon black much more difficult to clean up and control than the polysilocarb ceramic pigment. As such, it is preferably a non-sticking, non-clinging black pigment. These, among other features, are a significant improvement over carbon black, which is typically difficult to clean up, dusts, and clings to surfaces.

The polysilocarb ceramic pigment can have low oil absorption, leading to lower viscosities, which among other things, permits formulations to move to higher solids loading with lower VOC content. This pigment can have a diameter, for example, from about 0.1 µm to 300 µm, from about 1 µm to about 150 µm, less than 10 µm, less than 1 µm, less than 0.3 µm, and less than or equal to 0.1 µm.

An embodiment of a batch of the polysilocarb pigment, can have narrow or tight particle size (e.g., diameter) distribution. Thus, embodiments of these black ceramic pigments are particles that are within at least 90% of the targeted size, at least 95% of the targeted size, and at least 99% of the targeted size. For example, the patch of particles, can have size distributions such as at least about 90% of their size within a 10 µm range, at least about 95% of their size within a 10 µm range, at least about 98% of their size within a 10 µm range, and at least about 99% of their size within a 10 µm range. Further, and for example, the process can produce particles each of which can have at least about 90% of their size within a 5 µm range, at least about 95% of their size within a 5 µm range, at least about 98% of their size within a 5 µm range, and at least about 99% of their size within a 5 µm range. Further, and in submicron particle sized, for example, the process can produce particles each of which can have at least about 90% of their size within a 0.2 µm range, at least about 95% of their size within a 0.2 µm range, at least about 98% of their size within a 0.2 µm range, and at least about 99% of their size within a 0.2 µm range. More preferably, in sub micron sizes, embodiments these percentage tolerances can be for the 0.1 µm range, and the 0.05 µm range. Preferably, these levels of uniformity in the production of the particles are obtained without the need for filtering, sorting or screening the particles.

It should further be noted that preferably these size distributions are for particles, as used in the formulation. Thus, these particle size distributions can be agglomerated, and then upon de-agglomeration and preferably will have the same, substantially the same particle size distribution. In this manner, preferably the particle size, and size distribution after de-agglomeration are predictable and predetermined.

In a preferred embodiment the polysilocarb pigments is a black non-conductive, acid and alkali resistant, and thermally stable up to about 300° C., up to about 400° C. and up to about 500° C., or greater. In other embodiments the conductive properties of the pigment can be modified with additives and fillers, during the making of the pigment, and in this way providing a pigment that is conductive, and has a predetermined conductivity. The color and jetness of these black polysilocarb pigments is typically a function of the particle size. In a preferred embodiment of the polysilocarb pigment, mass-tone and tint strength can be comparable to, and in a further preferred embodiment can be superior to, current black pigments, e.g., carbon, carbonaceous, and oxide based black pigments. In preferred embodiments the polysilocarb pigments are non-hazardous, having no toxicological effects.

Embodiments of the black polysilocarb pigments can be used in, among other things, spray, brush-on and power coatings for applications on essentially all metal, ceramic and plastic surfaces in the industrial, marine, architectural, graphic arts & inks, and automotive fields. Embodiments of these pigments further can find applications in cosmetics, nail polish, food packaging, and pharmaceutical applications and fields, to name a few.

Embodiments of the black polymer derived ceramic pigments are easily dispersed in most media. The black polysilocarb pigments are easily and readily dispersed in most types of media, basis, resins and carriers. For example, HDPE, LDPE, PP, Acrylic, Epoxy, Linseed Oil, PU, PUR, EPDM, SBR, PVC, water based acrylic emulsions, ABS, SAN, SEBS, SBS, PVDF, PVDC, PMMA, PES, PET, NBR, PTFE, siloxanes, polyisoprene and natural rubbers, and combinations of these and others.

Embodiments of the black polymer derived ceramic pigments have very low oil absorption. The oil absorption for polysilocarb ceramic pigments can be less than about 50 (grams linseed oil per 100 grams of pigment, i.e. g/100 g), less than about 30 g/100 g, and less than about 15 g/100 g. On the other hand, typical specialty carbon black pigments have oil absorptions ranging from about 150 g/100 g to more than 200 g/100 g. Thus, embodiments of the present black polysilocarb ceramic pigments can have oil absorptions that are at least 13×, 5× or 3× lower than carbon black pigments having the same or similar blackness.

Embodiments of the black polymer derived ceramic pigments can find use in many applications and industries. For example, the polysilocarb derived ceramic pigments provide high temperature resistance capabilities, they are indoor/outdoor color fast, UV resistant, and are resistant to most chemicals, finding applications in harsh environments, such as marine and oil field environments. They are non-corrosive and non-conductive, which enables uses beyond that which most black pigments could be utilized. These uses would include Industrial and residential furnace coatings; engine components as high heat resistant plastic parts or coatings on metal parts; pipe coatings; chemical plant equipment coatings; oil field coatings; residential barbeques; aftermarket coatings; ceramic and glass inkjet inks; electronic coatings; battery anodes; gun barrel coatings; PVC siding, metal roof coatings; coloration of ceramic parts for many end uses; space craft coatings; sand coatings; microwave curable elastomers, plastics, inks and coatings; cookware; hotplates; satellite components; high heat absorbing coatings; proprietary military coatings; high heat resistant potting compound; electrical insulation; Fluoropolymer elastomers for use as seals and gaskets in extremely harsh environments; high emissivity coatings, thermal protection systems, thermal barrier coatings, thermal imaging coatings, injection-molded parts, thermoformed parts, transfer molded parts, compression molded parts, rotational molded parts, blow-molded parts, cast parts, vacuum formed parts, hot-isostatic pressed parts, sinterable parts, vacuum impregnated parts, impregnated fiber forms, woven fabrics, textiles, engineering textiles, woven fiber fabrics, fiber mats, wear resistant metal matrix composites, wear resistant ceramic matrix composites, wear resistant polymer matrix composites, mixed oxide ceramics, refractory applications, and combinations and variations of these and others.

Embodiments of the black polymer derived ceramic pigments are microwave safe, e.g., they do not absorb and are not effect by microwaves. Typical carbon black pigments, are effected by microwaves, and cannot be used in microwave environments or applications.

In an embodiment of a process to make polymer derived ceramic pigment, and preferably to make a black polymer derived ceramic pigment, in the make-up segment a precursor formulation is metered into a one cubic meter tank having an in-line mix at rate of about 0.22 cubic meters per hour along with a stream of the catalyst at a ratio of 1 part catalyst to 100 parts precursor. The in-line mix tank is equipped with a high speed mixer. Residence time in the mix tank is about twenty-five minutes. The polymerization reaction starts in the mix tank.

In this embodiment of the process, the forming and curing segments are combined. Thus, the catalyzed precursor formulation, after mixing, is continuously feed to a drum, or a moving belt, e.g., a flaker belt, and preferably a stainless steel flaker belt or other similar device. Nozzles, a drip trough, an elongated opening, or slice, or other metering and distribution apparatus can be used to preferably obtain a uniform distribution, including thickness, of the liquid precursor on the moving belt. When the precursor is laid down onto the belt, the precursor can be moving at the same speed as the belt, at a faster speed than the belt (e.g., rushed), or at a slower speed than the belt (e.g., dragged). As the liquid precursor is moved with the belt it is heated to a sufficient temperature to cure the precursor formulation to form a cured material. For example, radiant heaters may be use above the belt, tunnel dryers may be used, the belt itself may be heated, e.g., with steam or electric heaters, and combinations and variations of these and other apparatus and methods to heat and maintain the temperature of the precursor material being carried on the belt. For example, in a preferred embodiment the belt is heated to about 100-200° C. by a steam coil along the underside of the belt. The cross linking reaction, which first began in the mixing tank, continues as the precursor travels along the belt to the point that it solidifies, preferably the precursor has reached a predetermined and predicted cure amount, e.g., green cure, hard cure, final cure, by the time it reaches the end of the belt. Depending upon the precursor formulation, the amount of catalyst, the temperature and other factors, the residence time on the belt can be about 5 to about 60 minutes, more than about 10 minutes, more than about 20 minutes, about 20 minutes, and more than about 40 minutes, and greater and lesser durations.

In this embodiment, at the end of the belt, the cured precursor, e.g., green material, falls from the belt and into a chopper, which reduces the size of the green material to about ≤10 μm, about ≤100 μm, about ≤200 μm, and about ≤500 μm, as well as other sizes. The chopped cured material can be stored, in for example a storage hopper.

In this embodiment of the process, in the pyrolizing segment the polymer from the storage hopper is transferred to cars and fed to a furnace, e.g., a kiln, periodic (e.g., box) kiln, and preferably an oxygen deficient, natural gas fired tunnel kiln. The kiln is operated in an oxygen deficient regime to maintain a non-oxidizing atmosphere in the polymer. The cars move through the kiln, preferably at a constant rate, which results in a three phase, 24-hour pyrolysis process, e.g., a reforming process. In the first phase, the temperature of the polymer is raised to 1000° C. over a period of 16 hours. At the end of the 16-hour ramp period, it remains at this temperature, 1000° C., for two hours. In the final phase the material is air cooled to ambient temperature over the next six hours. Through this pyrolizing segment of the process the cured material, e.g., green material, is converted to a ceramic material. The ceramic material is removed, e.g., dumped from the kiln cars into an intermediate storage hopper awaiting further processing.

In this embodiment of the processes, throughout the pyrolizing segment, the exhaust gases from the kiln are preferably ducted away to a cleaning or waste handling system, for example to a Vapor Destruction Unit (VDU) to destroy residual combustibles. The VDU can than be followed by other cleaning systems, such as for example, a wet scrubber to remove any particulates (predominately silica). The silica can then be removed from the water effluent and recovered for reuse, sale or proper disposal. After removal of the silica, the effluent from the scrubber can be reused for example in a grey water loop, further cleaned and reused, or transferred to a waste water treatment facility for eventual discard.

In this embodiment of the process, in the post-processing segment three post processing techniques are used—jet milling, bead milling and spray drying. In many embodiments of applications for polymer derived ceramic pigments, and in particular for black polymer derived ceramic pigments, a particular particle size can be a factor, an application requirement, and in some instances a very important parameter for the pigment. In this embodiment, jet milling is the first stage of the size reduction process. Ceramic material having a particle size of about 300-500 μm, is taken from the intermediate storage; and is fed into the jet milling receiver. At the jet milling receiver the ceramic material is directed to several, e.g., two, three, four or more, parallel mills. The jet mills reduce the particle size from 300-500 μm, to about 1-20 μm, about 3 μm, and about 2 μm. The use of steam jet milling can reduce the particle size to about 1 μm, less than about 1 μm and about 0.5 μm and potentially smaller, these reductions in size can preferably be achieved un-surface treated, i.e., with out the need to provide a surface treatment to the larger particles prior to milling. The milled ceramic can then be classified and those sizes not meeting the requirements for further processing can be removed and preferably repurposed. For example, about 10% of the product can be classified and sold at an intermediate size.

The remaining 90% of the jet mill product is transferred to the bead mill receiver for further size reduction. The 1-20

μm jet milled product is fed to a slurry tank where it is mixed with a liquid phase or solvent, such as demineralized water, and a dispersant at a ratio of approximately 60 parts solids, 39 parts solvent and 1 part dispersant. The dispersant can be a soap, detergent, surfactant, fatty acid, natural oil, synthetic oil, wetting agent, dispersing agent, natural and synthetic oils, natural and synthetic glycols and polyglycols, modified waxes and hydrocarbons. Dispersants function to stabilize the particle via either steric, electrosteric, or electrostatic means and can be non-ionic, anionic, cationic, or zwitterionic. Structures can be linear polymers and copolymers, head-tail type modified polymers and copolymers, AB-block copolymers, ABA block copolymers, branched block copolymers, gradient copolymers, branched gradient copolymers, hyperbranched polymers and copolymers, star polymers and copolymers. BASF, Lubrizol, RT Vanderbilt, and BYK are all common manufacturers of dispersants. Trade names include: Lubrizol Solsperse series, Vanderbilt Darvan series, BASF Dispex series BYK DisperByk series, BYK LP-C 2XXXX series. Grades can include BYK DisperByk 162, 181, 182, 190, 193, 2200, and 2152; LP-C 22091, 22092, 22116, 22118, 22120, 22121, 22124, 22125, 22126, 22131, 22134, 22136, 22141, 22146, 22147, 22435; LP-N 22269; Solsperse 3000, Darvan C-N. A proper dispersant will provide good reduction in viscosity from a high-solids content paste with <5% additive, causing it to become a flowable liquid instead of a non-flowable paste. The ratio of dispersant to ceramic solids can range from about 0.01 wt % to 8 wt %, to 0.5 wt % to 4 wt %, 1 wt % to 3 wt %, and greater and lesser ratios. This slurry is fed, e.g., batch wise, semi-continuous or continuously, to single, to several parallel, two-stage bead milling systems, e.g., two, three, four, five or more. These mills may also have other mills serially connected to their outputs. Bead milling further reduces the particle size to less than 1 μm, and preferably for submicron applications to a particle size of about ≤0.1 μm.

In this embodiment the wet product from the bead is fed to a spray dryer, which can be steam heated, gas heated, air, inert gas, or electrically heated, where the water content is reduced to <1 percent. In the spray dryer, the 0.1 μm particles agglomerate to a 10-80 μm particle size, e.g., agglomerate size, agglomerated particle size. Preferably, a batch, lot, or shipment of the agglomerate particles has a median particle size distribution, e.g., $D_{50}$, of greater than about 10 μm, greater than about 20 μm, and greater than about 50 μm. Preferably these agglomerates are stable through the handling and shipping process and the unpacking and initial use for an application. In addition to the preferred median particle size distribution of greater than 10 μm, the mean agglomerate particle size may be from 10 μm or less, from about 10 μm to about 80 μm, and may be larger than 80 μm.

In this embodiment the exhaust from the spray dryer goes through a cyclone, followed by a bag filter to remove any particulates prior to release to the atmosphere. The collected dust is recycled to the bead mill or spray dryer feed. The water or solvent evaporated from the powder in the spray dryer is condensed, recovered and recycled to the bead mill feed slurry. The dry product from the spray dryer can be stored, packaged, shipped to users, or further processed or treated.

The product, e.g., the stored, packaged, shipped etc. pigment, can be in: a dry powered form; a dry agglomerate form; a sheet form, a block or other larger volumetric shape; a suspension having from about 20% solids (or less solids) to about 50% solids (or more), a paste, an aqueous paste, an aqueous suspension, and combinations and variations of these and other forms. For an embodiment of the product that is a dry powder, or dry agglomerate, the moisture content can be from about 0% to about 10% moisture, about less than 5%, about less than 3%, and about less than 1%.

In the foregoing embodiment of a process to make polymer derived ceramic pigment, a preferable embodiment of the polymer derived ceramic pigment is a black polysilocarb derived ceramic pigment. The black polysilocarb derived pigment can be used in many applications.

Polymer derived black ceramic pigments, and preferably black polysilocarb derived ceramic pigments have applications in, for example, coatings used on, or in, walls, appliances, automobiles, engines, pipes, grills, microwaves, cook wear, wires, printed circuit boards, human and animal nails, cosmetics, pipes, interior of components such as automobile components, food packaging and other devices, structures components and articles. They have applications in coatings that provide end use features, such as for example, corrosion protection, abrasion protection, skid resistance, decorative and astatic effects, photosensitive properties, UV protection, heat resistance and protection, and combinations and variations of these and other features. They have applications in coating that are organic, inorganic and combinations of these. They have applications in coatings that are porcelain, enamels, electroplated, to name a few others. They have applications in architectural coating, product coatings used by original equipment manufacturers ("OEM coatings"), special purpose coatings and other types of coatings. Architectural coatings would include for example paints and varnishes. Product coatings would include OEM coatings, industrial coatings, industrial finishes, boats, water craft, ships, after market coatings, and repair/refurbishing coatings, the products to which product coatings are applied is essentially endless, and would include for example automobiles, aircraft, appliances, wire, pipes, furniture, metal cans, chewing gum wrappers, packaging, equipment, etc. Specialty coatings would include for example, specialty coatings for cars, specialty marine coatings, stripping for highways, and others.

Polymer derived black ceramic pigments, and preferably black polysilocarb derived ceramic pigments have applications in coatings embodiments that contain a binder, volatile components, a pigment (which may be solely one or more polymer derived black ceramic pigments or combinations of the polymer derived black pigment and other pigments), and additives (noting that the polymer derived pigment, which may be other colors than black and preferably embodiments of polysilocarb pigments, which may be other colors than black, can function as, or are, additives). These pigments are used with all types of resin, including acrylics, alkyds, amino, cellulosics, epoxies, polyesters, urethanes, poly(vinyl acetates), poly(vinyl chlorides), and others.

The polymer derived black ceramic pigments, and preferably black polysilocarb derived ceramic pigments can have surface properties and sizes such that they do not change the rheology of existing formulations that use other types of black pigments. In this manner they can be directly substituted for some, or all of the other type of pigment in a particular formulation without changing the rheology of that formulation and providing for example improved blackness and opacity. The nature of these pigments also provides the ability to have an embodiment of these pigments that provides functionality to control, modify, and regulate the rheology of a formulation. In this manner these pigments would have a dual role in the formulation as a pigment and as a rheology control additive.

Embodiments of coatings containing black polysilocarb derived ceramic pigments provided enhanced abrasion resistance, e.g., the wearing away of a surface, and enhanced mar resistance, e.g., disturbances in the surface that alters its appearance. Abrasion and mar resistance would include resistance to scratching, gouging, wearing, and generally the resistance to the detrimental effects that occur when two surfaces are in sliding contact. Coatings using the black polysilocarb derived ceramic pigments have abrasion resistance as measured by Taber Abrasion Tester (reported as number of mg of coating worn off after 1,000 cycles) of at most 30 mg, at most 150 mg, from about 10 mg to about 200 mg, and greater than 200 mg.

Embodiment of coatings containing black polysilocarb derived ceramic pigments provided enhanced hardness. Hardness for coatings typically is measured by way of indentations, scratch, and pendulum tests. Hardness tests for coatings typically include an indentation test, the falling ball indentation Test (ASTM D-2394, which is well known to and available to the art, and the entire disclosure of which is incorporated herein by reference), a scratch test, the pencil hardness test (ASTM-D-3363-00, which is well known to and available to the art, and the entire disclosure of which is incorporated herein by reference), and a pendulum test, the Sward rocker (ASTM-2134-93), which is well known to and available to the art, and the entire disclosure of which is incorporated herein by reference).

Embodiment of Coatings using the black polysilocarb derived ceramic pigments have indentation test results of at least 100 inch pounds at least 160 inch pounds, from about 50 to about 150 inch pounds, and greater than 160 inch pounds. Coatings using the black polysilocarb derived ceramic pigments can have the same or better blackness, while having increases in indentation test results of at least about 50 inch pounds, at least about 160 inch pounds, and greater, when compared to a similar formulation using carbon black or metal oxides as the pigment.

Embodiments of coatings using the black polysilocarb derived ceramic pigments have scratch test results of at least 7B pencil, at least F pencil, from about 8B pencil to about 6H pencil, and greater than 6H pencil. Coatings using the black polysilocarb derived ceramic pigments can have the same or better blackness, while having increases in scratch test results of at least about 7B pencil, at least about F pencil, and greater, when compared to a similar formulation using carbon black or metal oxides as the pigment.

Embodiments of coatings using the black polysilocarb derived ceramic pigments have pendulum test results of at least 20 oscillations at least 25 oscillations, from about 15 to about 55 oscillations, and greater than 56 oscillations. Coatings using the black polysilocarb derived ceramic pigments can have the same or better blackness, while having increases in pendulum test results of at least about 20 oscillations, at least about 50 oscillations, and greater, when compared to a similar formulation using carbon black or metal oxides as the pigment.

The polymer derived black ceramic pigments, and preferably black polysilocarb derived ceramic pigments can be used in formulations having UV stabilizers. These pigments do not diminish or adversely affect the UV stabilizing ability performance of the UV stabilizers. It is theorized that the polysilocarb derived ceramic pigments may provide added UV stabilization to these UV stabilized formulations. The UV stabilizers can be UV absorbers, UV quenchers, and combinations of these. Typical UV stabilizes include, for example, 2-hydroxybenzophenones, 2-(2-hydroxyphenyl)-2H-benztriazoles, 2-(2-hydroxyphenyl)-4,6-phenyl-1,3,5-triazines, benzylidenemalonates, oxalanilides and others.

Typically, embodiments of the polymer derived black ceramic pigments, and preferably black polysilocarb derived ceramic pigments can function as a UV absorber, and can be added to coatings to provide these function, thus function as both a additive and a pigment. Embodiments of a 3.0 μm $D_{50}$ black polysilocarb derived ceramic pigment exhibit UV absorption (e.g., absorption coefficient, e.g., absorptivity) based upon the UV-vis data taken in diluted DI water solutions, set out in Table 1. The concentration of material is given in grams per 100 g of water (equivalently, g/100 mL). These concentrations gave a translucent solution.

TABLE 1

| | absorption coefficient | | |
|---|---|---|---|
| concentration (g/100 g) | dB/cm/ concentration @ 300 nm | dB/cm/ concentration @ 450 nm | dB/cm/ concentration @ 800 nm |
| 0.00952 | 3538.894732 | 3526.83657 | 3451.4463 |
| 0.02590 | 979.6193238 | 961.519095 | 946.46022 |

Generally, embodiments of the polysilocarb derived ceramic pigment can have absorption coefficients of greater than 500 dB/cm/(g/100 g), greater than 5,000 dB/cm/(g/100 g), greater than 10,000 dB/cm/(g/100 g), from about 500 dB/cm/(g/100 g) to about 1,000 dB/cm/(g/100 g), from about 1,000 to about 5,000 dB/cm/(g/100 g), and from about 500 dB/cm/(g/100 g) to about 10,000 dB/cm/(g/100 g). In general, the smaller the pigments size, for the same pigment the higher will be the absorption coefficients.

The polymer derived black ceramic pigments, and preferably black polysilocarb derived ceramic pigments can be used in formulations having antioxidants. These pigments do not diminish or adversely affect the anti-oxidizing performance of the antioxidants. It is theorized that the polysilocarb derived ceramic pigments may provide added anti-oxidation protection to these antioxidant containing formulations. Typical antioxidants include for example preventive antioxidants, peroxide decomposers, sulfides, phosphites, metal complex agents, and others.

The polymer derived black ceramic pigments, and preferably black polysilocarb derived ceramic pigments can be used in formulations having hinder amine light stabilizers ("HALS"), which function to prevent the photo oxidative degradation of coatings. These pigments do not diminish or adversely affect the photo-oxidizing performance of the HALS. It is theorized that the polysilocarb derived ceramic pigments may provide added photo-oxidation protection to these HALS containing formulations. Further, the black polysilocarb derived ceramic pigments in some embodiments can be used to replace some, most, and all, of the HALS in the coating.

The polymer derived black ceramic pigments, and preferably black polysilocarb derived ceramic pigments can be used in many types of coating or formulations, such as for example thermoplastic acrylic resins, thermosetting acrylic resins, hydroxy-functional acrylic resins, water reducible thermosetting acrylic resins, waterborne coatings (i.e., any coating with an aqueous media, e.g., latex coatings), water reducible coatings (i.e., a waterborne coating based on a resin having hydrophilic groups in most or all of its molecules), water soluble coatings (i.e., are soluble in water), latexes, acrylic latexes, vinyl ester latexes, thermosetting latexes, polyester resins, hydroxy-terminated polyester resins, amino resins, aminoplast resins, baked thermosetting coatings, melamine-formaldehyde resins (e.g., class I and class II), urea-formaldehyde resins, benzoguanamine-formaldehyde resins, glycoluril-formaldehyde resins, poly(meth)acrylamide-formaldehyde resins, polyurethane resins, two package solvent borne urethane coatings, epoxy resins, waterborne epoxy-amine systems, drying oil based resins, varnishes, alkyd resins, silicones, silicone rubber resins, and tetraethylorthosilicate (TEOS) based resins, among others.

The polymer derived black ceramic pigments, and preferably black polysilocarb derived ceramic pigments can be used in many types of coating or formulations that utilize different types of solvents, such as for example, weak hydrogen-bonding solvents (e.g., aliphatic and aromatic hydrocarbons), hydrogen-bond acceptor solvents (e.g., esters and ketones) and hydrogen-bond donor-acceptor solvents (e.g., alcohols and propylene glycol).

In general, the smaller the particle size, the greater the fraction of light that will be absorbed by the same quantity, i.e., weight of particles. For pigments, and generally for embodiments of the polymer derived black ceramic pigments, and preferably black polysilocarb derived ceramic pigments, the smaller the particle size of the pigment the greater the absorption of light.

The ability of a coating to hiding the substrate, i.e., hiding, is a property that can be affected by many factors. Generally, hiding increases as film or coating thickness increases at the same pigment loading. Lower hiding coatings require thicker films. Also, hiding increases as pigment particle size decreases until a maximum hiding is reached and then hiding begins to decrease. Two coatings will hide the substrate the same, one with a lower pigment loading (of smaller particle size) and one with a higher pigment loading of a larger particle size. In general, embodiments of the polymer derived black ceramic pigments, and preferably black polysilocarb derived ceramic pigments, provide higher hiding coatings, or hiding ability, for the same loading (e.g., weight of pigment to volume of coating) of black mixed metal oxide pigments and more quickly approach the hiding power of furnace carbon black.

TABLE 2

| Pigment Type | Particle size (micron) | Pigment loading to hiding |
| --- | --- | --- |
| PolySiloCarb | 2.5 to 3.5 | 1 lb/gallon to 1.5 lbs/gallon |
| PolySiloCarb | 1.5 to 2.5 | 0.8 lbs/gallon to 1 lb/gallon |
| PolySiloCarb | 1.0 to 1.5 | 0.7 to 0.8 lbs/gallon |
| PolySiloCarb | 0.8 to 1.0 | 0.6 to 0.7 lbs/gallon |
| PolySiloCarb | 0.6 to 0.8 | 0.55 to 0.60 lbs/gallon |
| PolySiloCarb | 0.4 to 0.6 | 0.45 to 0.55 lbs/gallon |
| PolySiloCarb | 0.2 to 0.4 | 0.35 to 0.45 lbs/gallon |
| PolySiloCarb | 0.1 to 0.2 | 0.25 to 0.35 lbs/gallon |
| PolySiloCarb | less than 0.1 | less than 0.25 lbs/gallon |
| CI Black 28 | about 0.5 | about 0.5 lbs/gallon |
| CI Black 26 | about 0.3 | about 0.3 lbs/gallon |
| Thermal Carbon Black | 0.25 to 0.35 | about 0.4 lbs/gallon |
| FurnaceCarbon Black | 0.03-0.05 | 0.1 to 0.2 lbs/gallon |

Pigment loading to hiding is the required weight of pigment in a 50 micron dry film coating to cover a black and white substrate such that the eye cannot differentiate a difference in color over either colored background.

In general, in using the polymer derived black ceramic pigments, and preferably the black polysilocarb derived ceramic pigments, they can be formulated, mixed or made into a concentrated composition that can typically, although not necessarily, have other ingredients. These concentrated compositions are typically liquids, although not necessarily, they typically are call mill bases, dispersions, colorants, master-batches, and similar terms, which terms for the purposes of this specification, unless specifically stated otherwise, will be used to interchangeably. The present black ceramic pigments have excellent wettability, separation properties, and stability properties in both organic and aqueous media.

Polymer derived ceramic mill bases can contain one embodiment of the present ceramic pigments, several different embodiments of the present ceramic pigments, other types of pigments, such as carbon black, and combinations and variations of these. When more than one pigment is present the mill base can be referred to as a composite grind, or composite grind mill base. Thus, for example, an embodiment of a polymer derived ceramic a composite grind mill base has a black polysilocarb ceramic pigment and one or more of the following pigments: organic pigments, such as arylamide yellow (PY 73), diarylide yellow, barium red 2B toner (PR 48.1); polycyclic pigments, such as copper phthalocyanine, dioxanzine violet (PV 23), tetrachloro thiondigo (PR 88); inorganic pigments, such as carbon black, titanium dioxide, iron oxides, azurite, cadmium sulphides.

Although in embodiments of the present black ceramic pigments, dispersants are not needed or required, they may be added to either the mill base, or with the mill base at the time it is added to the coating formulation. Dispersants such as polymeric dispersants, A-B copolymer dispersants, hyperdispersants, superdispersants, and others may be used. In general dispersants function to stabilize the particle via either steric, electrosteric, or electrostatic means and can be non-ionic, anionic, cationic, or zwitterionic. Embodiments of dispersant structures can be linear polymers and copolymers, head-tail type modified polymers and copolymers, AB-block copolymers, ABA block copolymers, branched block copolymers, gradient copolymers, branched gradient copolymers, hyperbranched polymers and copolymers, star polymers and copolymers, and combinations and various of these and others.

It being understood that the mill base can be prepared and stored for later use, shipped, or used immediately. Further the step of making a mill base may be combined with, a part of, or otherwise incorporated into the process of formulation and making the coating. Generally in making a polymer derived ceramic pigmented coating three steps typically may be used—premixing, e.g., stirring the dry pigment into a liquid vehicle and eliminating any lumps; imparting shear stress to separate the pigment aggregates, which may be done in the presence of a dispersion stabilizer; and, letting down, which entails combining the pigment dispersion, e.g., mill base, with the remainder of the ingredients for the coating formulation. It being understood that some equipment is capable of performing only one or two of the steps, while other are capable of performing all three steps.

Equipment that may be used for forming the mill base can include, for example, high-speed disk dispersers, rotor—stator mixers, ball mills, basket mills, shot mills, hammer mills, media mills (e.g., sand mills, shot mills, bead mills), three roll mills, two roll mills, extruders, kneaders, internal batch mixers, such as banbury machines, extruders, ultrasound dispersers, and others.

The polymer derived black ceramic pigments, and preferably the black polysilocarb derived ceramic pigments can be used to make tinting pastes in this manner providing an embodiment of a polymer derived tinting paste. In general tinting paste will have a high loading of pigment to a small amount of resin so that a small amount of paste will give the maximum color. The polymer derived black ceramic pigments, and preferably the black polysilocarb derived ceramic pigments improve the tint strength as the particle size decreases. In general, tinting embodiments of the polymer derived black ceramic pigments, and preferably black polysilocarb derived ceramic pigments, provide higher tinting strength in coatings, (less black pigment required to reach the same grey color with a lightness value between 72 and 75 on the CIELAB Lab scale, the lightness coming from a larger amount of $TiO_2$ white pigment which is tinted to a grey color by small additions of the black pigment). The smaller particle size polymer derived black ceramic pigment has higher tinting strength than black mixed metal oxide pigments and more quickly approaches the tinting strength of furnace carbon black. Tinting pastes can use multiple black additives, including polysilocarb materials.

TABLE 3

| Pigment Type | Particle size (micron) | Pigment loading to light grey |
|---|---|---|
| PolySiloCarb | 2.5 to 3.5 | 12 to 15 parts |
| PolySiloCarb | 1.5 to 2.5 | 11 to 12 parts |
| PolySiloCarb | 1.0 to 1.5 | 10 to 11 parts |
| PolySiloCarb | 0.8 to 1.0 | 9 to 10 parts |
| PolySiloCarb | 0.6 to 0.8 | 7.5 to 9 parts |
| PolySiloCarb | 0.4 to 0.6 | 6.5 to 7.5 parts |
| PolySiloCarb | 0.2 to 0.4 | 4.5 to 6.5 parts |
| PolySiloCarb | 0.1 to 0.2 | 2.5 to 4.5 parts |
| PolySiloCarb | less than 0.1 | less than 2.5 parts |
| CI Black 28 | about 0.5 | 7 to 8 parts |
| CI Black 26 | about 0.3 | 3.5 to 4.5 parts |
| FurnaceCarbon Black | 0.03-0.05 | 1 part |

It should be understood that the use of headings in this specification is for the purpose of clarity, reference, and is not limiting in any way. Thus, the processes compositions, and disclosures described under a heading should be read in context with the entirely of this specification, including the various examples. The use of headings in this specification should not limit the scope of protection afford the present inventions.

General Processes for Obtaining a Polysilocarb Precursor

Typically polymer derived ceramic precursor formulations, and in particular polysilocarb precursor formulations can generally be made by three types of processes, although other processes, and variations and combinations of these processes may be utilized. These processes generally involve combining precursors to form a precursor formulation. One type of process generally involves the mixing together of precursor materials in preferably a solvent free process with essentially no chemical reactions taking place, e.g., "the mixing process." The other type of process generally involves chemical reactions, e.g., "the reaction type process," to form specific, e.g., custom, precursor formulations, which could be monomers, dimers, trimers and polymers. A third type of process has a chemical reaction of two or more components in a solvent free environment, e.g., "the reaction blending type process." Generally, in the mixing process essentially all, and preferably all, of the chemical reactions take place during subsequent processing, such as during curing, pyrolysis and both.

It should be understood that these terms—reaction type process, reaction blending type process, and the mixing type process—are used for convenience and as a short hand reference. These terms are not, and should not be viewed as, limiting. For example, the reaction process can be used to create a precursor material that is then used in the mixing process with another precursor material.

These process types are described in this specification, among other places, under their respective headings. It should be understood that the teachings for one process, under one heading, and the teachings for the other processes, under the other headings, can be applicable to each other, as well as, being applicable to other sections, embodiments and teachings in this specification, and vice versa. The starting or precursor materials for one type of process may be used in the other type of processes. Further, it should be understood that the processes described under these headings should be read in context with the entirely of this specification, including the various examples and embodiments.

It should be understood that combinations and variations of these processes may be used in reaching a precursor formulation, and in reaching intermediate, end and final products. Depending upon the specific process and desired features of the product the precursors and starting materials for one process type can be used in the other. A formulation from the mixing type process may be used as a precursor, or component in the reaction type process, or the reaction blending type process. Similarly, a formulation from the reaction type process may be used in the mixing type process and the reaction blending process. Similarly, a formulation from the reaction blending type process may be used in the mixing type process and the reaction type process. Thus, and preferably, the optimum performance and features from the other processes can be combined and utilized to provide a cost effective and efficient process and end product. These processes provide great flexibility to create custom features for intermediate, end, and final products, and thus, any of these processes, and combinations of them, can provide a specific predetermined product. In selecting which type of process is preferable, factors such as cost, controllability, shelf life, scale up, manufacturing ease, etc., can be considered.

In addition to being commercially available the precursors may be made by way of an alkoxylation type process, e.g., an ethoxylation process. In this process chlorosilanes are reacted with ethanol in the presences of a catalysis, e.g., HCl, to provide the precursor materials, which materials may further be reacted to provide longer chain precursors. Other alcohols, e.g., methanol may also be used. Thus, for example $SiCl_4$, $SiCl_3H$, $SiCl_2(CH_3)_2$, $SiCl_2(CH_3)H$, $Si(CH_3)3Cl$, $Si(CH_3)ClH$, are reacted with ethanol $CH_3CH_2OH$ to form precursors. In some of these reactions phenols may be the source of the phenoxy group, which is substituted for a hydride group that has been placed on the silicon. One, two or more step reactions may need to take place.

Precursor materials may also be obtained by way of an acetylene reaction route. In general there are several known paths for adding acetylene to Si—H. Thus, for example, tetramethylcyclotetrasiloxane can be reacted with acetylene in the presence of a catalyst to produce tetramethyltetravinylcyclotetrasiloxane. This product can then be ring opened and polymerized in order to form linear vinyl,methylsiloxanes. Alternatively, typical vinyl silanes can be produced by reacting methyl,dichlorosilane (obtained from the direct process or Rochow process) with acetylene. These monomers can then be purified (because there may be some scrambling) to form vinyl, methyl, dichlorosilane. Then the vinyl monomer can be polymerized via hydrolysis to form many cyclic, and linear siloxanes, having various chain lengths, including for example various cyclotetrasiloxanes (e.g., $D_4'$) and various cyclopentasiloxanes (e.g., $D_5'$). These paths, however, are costly, and there has been a long standing and increasing need for a lower cost raw material source to produce vinyl silanes. Prior to the present inventions, it was not believed that MHF could be used in an acetylene addition process to obtain vinyl silanes. MHF is less expensive than vinyl,methyl (either linear or cyclic), and adding acetylene to MHF to make vinyl meets, among other things, the long standing need to provide a more cost effective material and at relatively inexpensive costs. In making this addition the following variables, among others, should be considered and controlled: feed ($D_4'$, linear methyl, hydrogen siloxane fluids); temperature; ratio of acetylene to Si—H; homogeneous catalysts (Karstedt's, DBT Laureate, no catalyst, Karstedt's with inhibitor); supported catalysts (Pt on carbon, Pt on alumina, Pd on alumina); flow rates (liquid feed, acetylene feed); pressure; and, catalyst concentration. Examples of embodiments of reactions providing for the addition of acetylene to MHF (cyclic and linear) are provided in Tables A and B. Table A are batch acetylene reactions. Table B are continuous acetylene reactions. It should be understood that batch, continuous, counter current flow of MHF and acetylene feeds, continuous recycle of single pass material to achieve higher conversions, and combinations and variations of these and other processes can be utilized.

TABLE A

Batch Acetylene Reactions

| Run | Si—H | Methyl Hydride (grams) | Catalyst % (rel to MeH) | Inhibitor | Solvent | Amount of Solvent (grams) | Temp (° C.) | Acetylene Flow (ccm) | Reaction Time (hrs) | Acetyl Mol % (rel to Total Hydride) |
|---|---|---|---|---|---|---|---|---|---|---|
| 1 | MHF | 400 | 0.48% | 0.00% | — | — | 80-100 | — | 0.20 | — |
| 2 | MHF | 1000 | 0.27% | 0.00% | — | — | 65-75 | 276-328 | 0.75 | 3.4% |
| 3 | MHF | 1000 | 0.00% | 0.00% | — | — | 80 100 120 | 378-729 | 6.33 | 49.4% |
| 4 | MHF | 117 | 0.20% | 0.00% | Hexane | 1000 | 60-66 | 155-242 | 4.50 | 188.0% |
| 5 | MHF | 1000 | 0.40% | 0.40% | — | — | 55-90 | 102 | 7.5 | 15.7% |
| 6 | MHF | 360 | 1.00% | 0.00% | Hexane | 392 | 65 | 102 | 6.4 | 40.3% |
| 7a | MHF | 360 | 0.40% | 0.00% | Hexane | 400 | 65 | — | 2.0 | 23.4% |
| 7b | MHF | 280 | 0.40% | 0.00% | Hexane | 454 | 68 | — | 137.0 | 23.4% |
| 8 | D4' | 1000 | 0.27% | 0.00% | — | — | 79 | 327-745 | 6.5 | 61.3% |
| 9 | MHF | 370 | 0.40% | 0.00% | Hexane | 402 | 65 | 155-412 | 8.0 | 140.3% |

TABLE B

Continuous Acetylene Reactions

| Run | Si—H | Catalyst % (rel to MeH) | Inhibitor | Silane Conc (wt %) | Solvent | Reactor Temp (° C.) | Reactor Pressure (psig) | Acetyl Mol % (rel to Total Hydride) |
|---|---|---|---|---|---|---|---|---|
| 10 | D4' | 5% Pt on Carbon | 0.00% | 100.0% | — | 60-100 | 50 | 40.0% |
| 11 | D4' | 5% Pt on Carbon | 0.00% | 100.0% | — | 50-90 | 100 | 20.0% |
| 12 | D4' | 1% Pt on Alumina | 0.00% | 100.0% | — | 40-50 | 50 | 23.8% |
| 13 | MHF | 5% Pt on Carbon | 0.00% | 100.0% | — | 55-60 | 55-60 | 13.6% |
| 14 | MHF | 0.01% Pt on Alumina | 0.00% | 20.0% | Hexane | 20-25 | 50 | 108.5% |
| 15 | MHF | 0.01% Pt on Alumina | 0.00% | 20.0% | Hexane | 60 | 50-55 | 117.1% |
| 16 | MHF | 0.01% Pt on Alumina | 0.00% | 20.0% | Hexane | 70 | 50 | 125.1% |
| 17 | MHF | 0.12% Pt on Alumina | 0.00% | 20.0% | Hexane | 60 | 50 | 133.8% |
| 18 | MHF | 0.12% Pt on Alumina | 0.00% | 4.0% | Hexane | 60 | 50 | 456.0% |

($D_4'$ is tetramethyl tetrahydride cyclotetrasiloxane)

Continuous High Pressure Reactor ("CHPR") embodiments may be advantageous for, among other reasons: reaction conversion saving more acetylene needed in liquid phase; tube reactors providing pressures which in turn increases solubility of acetylene; reaction with hexyne saving concentration and time (e.g., 100 hours); can eliminate homogeneous catalyst and thus eliminate hydrosilylation reaction with resultant vinyls once complete; and, using a heterogeneous (Solid) catalyst to maintain product integrity, increased shelf-life, increase pot-life and combinations and variations of these.

In addressing the various conditions in the acetylene addition reactions, some factors may be: crosslinking retardation by dilution, acetylene and lower catalyst concentration; and conversion (using heterogeneous catalyst) may be lower for larger linear molecules compared to smaller molecules.

The presence and quality of vinyl and vinyl conversions can be determined by, among other things: FT-IR for presence of vinyl absorptions, decrease in SiH absorption; $^1$H NMR for presence of vinyls and decrease in SiH; $^{13}$C NMR for presence of vinyls.

As used herein, unless specified otherwise the terms %, weight % and mass % are used interchangeably and refer to the weight of a first component as a percentage of the weight of the total, e.g., formulation, mixture, material or product. As used herein, unless specified otherwise "volume %" and "% volume" and similar such terms refer to the volume of a first component as a percentage of the volume of the total, e.g., formulation, material or product.

The Mixing Type Process

Precursor materials may be methyl hydrogen, and substituted and modified methyl hydrogens, siloxane backbone additives, reactive monomers, reaction products of a siloxane backbone additive with a silane modifier or an organic modifier, and other similar types of materials, such as silane based materials, silazane based materials, carbosilane based materials, phenol/formaldehyde based materials, and combinations and variations of these. The precursors are preferably liquids at room temperature, although they may be solids that are melted, or that are soluble in one of the other precursors. (In this situation, however, it should be understood that when one precursor dissolves another, it is nevertheless not considered to be a "solvent" as that term is used with respect to the prior art processes that employ non-constituent solvents, e.g., solvents that do not form a part or component of the end product, are treated as waste products, and both.)

The precursors are mixed together in a vessel, preferably at room temperature. Preferably, little, and more preferably no solvents, e.g., water, organic solvents, polar solvents, non-polar solvents, hexane, THF, toluene, are added to this mixture of precursor materials. Preferably, each precursor material is miscible with the others, e.g., they can be mixed at any relative amounts, or in any proportions, and will not separate or precipitate. At this point the "precursor mixture" or "polysilocarb precursor formulation" is compete (noting that if only a single precursor is used the material would simply be a "polysilocarb precursor" or a "polysilocarb precursor formulation" or a "formulation"). Although complete, fillers and reinforcers may be added to the formulation. In preferred embodiments of the formulation, essentially no, and more preferably no chemical reactions, e.g., crosslinking or polymerization, takes place within the formulation, when the formulation is mixed, or when the formulation is being held in a vessel, on a prepreg, or over a time period, prior to being cured.

The precursors can be mixed under numerous types of atmospheres and conditions, e.g., air, inert, $N_2$, Argon, flowing gas, static gas, reduced pressure, elevated pressure, ambient pressure, and combinations and variations of these.

Additionally, inhibitors such as cyclohexane, 1-Ethynyl-1-cyclohexanol (which may be obtained from ALDRICH), Octamethylcyclotetrasiloxane, and tetramethyltetravinylcyclotetrasiloxane, may be added to the polysilocarb precursor formulation, e.g., an inhibited polysilocarb precursor formulation. It should be noted that tetramethyltetravinylcyclotetrasiloxane may act as both a reactant and a reaction retardant (e.g., an inhibitor), depending upon the amount present and temperature, e.g., at room temperature it is a retardant and at elevated temperatures it is a reactant. Other materials, as well, may be added to the polysilocarb precursor formulation, e.g., a filled polysilocarb precursor formulation, at this point in processing, including fillers such as SiC powder, carbon black, sand, polymer derived ceramic particles, pigments, particles, nano-tubes, whiskers, or other materials, discussed in this specification or otherwise known to the arts. Further, a formulation with both inhibitors and fillers would be considered an inhibited, filled polysilocarb precursor formulation.

Depending upon the particular precursors and their relative amounts in the polysilocarb precursor formulation, polysilocarb precursor formulations may have shelf lives at room temperature of greater than 12 hours, greater than 1 day, greater than 1 week, greater than 1 month, and for years or more. These precursor formulations may have shelf lives at high temperatures, for example, at about 90° F., of greater than 12 hours, greater than 1 day, greater than 1 week, greater than 1 month, and for years or more. The use of inhibitors may further extend the shelf life in time, for higher temperatures, and combinations and variations of these. The use of inhibitors, may also have benefits in the development of manufacturing and commercial processes, by controlling the rate of reaction, so that it takes place in the desired and intended parts of the process or manufacturing system.

As used herein the term "shelf life" should be given its broadest possible meaning, unless specified otherwise, and would include, for example, the formulation being capable of being used for its intended purpose, or performing, e.g., functioning, for its intended use, at 100% percent as well as a freshly made formulation, at least about 90% as well as a freshly made formulation, at least about 80% as well as a freshly made formulation, and at least about 70% as well as a freshly made formulation.

Precursors and precursor formulations are preferably nonhazardous materials. They have flash points that are preferably above about 70° C., above about 80° C., above about 100° C. and above about 300° C., and above. Preferably, they may be noncorrosive. Preferably, they may have a low vapor pressure, may have low or no odor, and may be non- or mildly irritating to the skin.

A catalyst or initiator may be used, and can be added at the time of, prior to, shortly before, or at an earlier time before the precursor formulation is formed or made into a structure, prior to curing. The catalysis assists in, advances, and promotes the curing of the precursor formulation to form a preform.

The time period where the precursor formulation remains useful for curing after the catalysis is added is referred to as "pot life", e.g., how long can the catalyzed formulation remain in its holding vessel before it should be used. Depending upon the particular formulation, whether an inhibitor is being used, and if so the amount being used, storage conditions, e.g., temperature, low $O_2$ atmosphere, and potentially other factors, precursor formulations can have pot lives, for example, of from about 5 minutes to about 10 days, about 1 day to about 6 days, about 4 to 5 days, about 30 minutes, about 15 minutes, about 1 hour to about 24 hours, and about 12 hours to about 24 hours.

The catalyst can be any platinum (Pt) based catalyst, which can, for example, be diluted to a ranges of: about 0.01 parts per million (ppm) Pt to about 250 ppm Pt, about 0.03 ppm Pt, about 0.1 ppm Pt, about 0.2 ppm Pt, about 0.5 ppm Pt, about 0.02 to 0.5 ppm Pt, about 1 ppm to 200 ppm Pt and preferably, for some applications and embodiments, about 5 ppm to 50 ppm Pt. The catalyst can be a peroxide based catalyst with, for example, a 10 hour half life above 90 C at a concentration of between 0.1% to 3% peroxide, and about 0.5% and 2% peroxide. It can be an organic based peroxide. It can be any organometallic catalyst capable of reacting with Si—H bonds, Si—OH bonds, or unsaturated carbon bonds, these catalysts may include: dibutyltin dilaurate, zinc octoate, peroxides, organometallic compounds of for example titanium, zirconium, rhodium, iridium, palladium, cobalt or nickel. Catalysts may also be any other rhodium, rhenium, iridium, palladium, nickel, and ruthenium type or based catalysts. Combinations and variations of these and other catalysts may be used. Catalysts may be obtained from ARKEMA under the trade name LUPEROX, e.g., LUPEROX 231; and from Johnson Matthey under the trade names: Karstedt's catalyst, Ashby's catalyst, Speier's catalyst.

Further, custom and specific combinations of these and other catalysts may be used, such that they are matched to specific formulations, and in this way selectively and specifically catalyze the reaction of specific constituents. Moreover, the use of these types of matched catalyst—formulations systems may be used to provide predetermined product features, such as for example, pore structures, porosity, densities, density profiles, high purity, ultra high purity, and other morphologies or features of cured structures and ceramics.

In this mixing type process for making a precursor formulation, preferably chemical reactions or molecular rearrangements only take place during the making of the starting materials, the curing process, and in the pyrolizing process. Chemical reactions, e.g., polymerizations, reductions, condensations, substitutions, take place or are utilized in the making of a starting material or precursor. In making a polysilocarb precursor formulation by the mixing type process, preferably no and essentially no, chemical reactions and molecular rearrangements take place. These embodiments of the present mixing type process, which avoid the need to, and do not, utilize a polymerization or other reaction during the making of a precursor formulation, provides significant advantages over prior methods of making polymer derived ceramics. Preferably, in the embodiments of these mixing type of formulations and processes, polymerization, crosslinking or other chemical reactions take place primarily, preferably essentially, and more preferably solely during the curing process.

The precursor may be a siloxane backbone additive, such as, methyl hydrogen (MH), which formula is shown below.

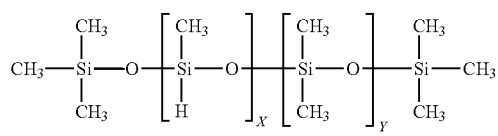

The MH may have a molecular weight ("mw" which can be measured as weight averaged molecular weight in amu or as g/mol) from about 400 mw to about 10,000 mw, from about 600 mw to about 3,000 mw, and may have a viscosity preferably from about 20 cps to about 60 cps. The percentage of methylsiloxane units "X" may be from 1% to 100%. The percentage of the dimethylsiloxane units "Y" may be from 0% to 99%. This precursor may be used to provide the backbone of the cross-linked structures, as well as, other features and characteristics to the cured preform and ceramic material. This precursor may also, among other things, be modified by reacting with unsaturated carbon compounds to produce new, or additional, precursors. Typically, methyl hydrogen fluid (MHF) has minimal amounts of "Y", and more preferably "Y" is for all practical purposes zero.

The precursor may be a siloxane backbone additive, such as vinyl substituted polydimethyl siloxane, which formula is shown below.

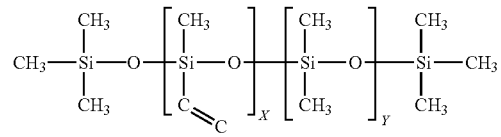

This precursor may have a molecular weight (mw) from about 400 mw to about 10,000 mw, and may have a viscosity preferably from about 50 cps to about 2,000 cps. The percentage of methylvinylsiloxane units "X" may be from 1% to 100%. The percentage of the dimethylsiloxane units "Y" may be from 0% to 99%. Preferably, X is about 100%. This precursor may be used to decrease cross-link density and improve toughness, as well as, other features and characteristics to the cured preform and ceramic material.

The precursor may be a siloxane backbone additive, such as vinyl substituted and vinyl terminated polydimethyl siloxane, which formula is shown below.

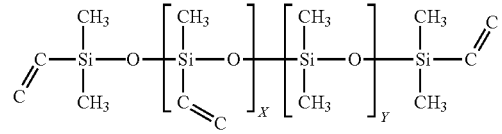

This precursor may have a molecular weight (mw) from about 500 mw to about 15,000 mw, and may preferably have a molecular weight from about 500 mw to 1,000 mw, and may have a viscosity preferably from about 10 cps to about 200 cps. The percentage of methylvinylsiloxane units "X" may be from 1% to 100%. The percentage of the dimethylsiloxane units "Y" may be from 0% to 99%. This precursor may be used to provide branching and decrease the cure temperature, as well as, other features and characteristics to the cured preform and ceramic material.

The precursor may be a siloxane backbone additive, such as vinyl substituted and hydrogen terminated polydimethyl siloxane, which formula is shown below.

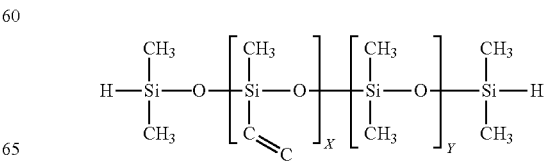

This precursor may have a molecular weight (mw) from about 300 mw to about 10,000 mw, and may preferably have a molecular weight from about 400 mw to 800 mw, and may have a viscosity preferably from about 20 cps to about 300 cps. The percentage of methylvinylsiloxane units "X" may be from 1% to 100%. The percentage of the dimethylsiloxane units "Y" may be from 0% to 99%. This precursor may be used to provide branching and decrease the cure temperature, as well as, other features and characteristics to the cured preform and ceramic material.

The precursor may be a siloxane backbone additive, such as allyl terminated polydimethyl siloxane, which formula is shown below.

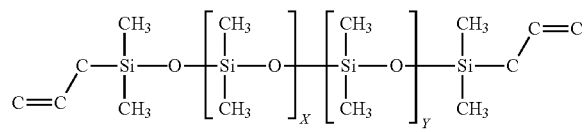

This precursor may have a molecular weight (mw) from about 400 mw to about 10,000 mw, and may have a viscosity preferably from about 40 cps to about 400 cps. The repeating units are the same. This precursor may be used to provide UV curability and to extend the polymeric chain, as well as, other features and characteristics to the cured preform and ceramic material.

The precursor may be a siloxane backbone additive, such as vinyl terminated polydimethyl siloxane, which formula is shown below.

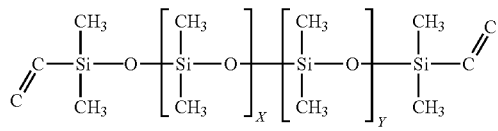

This precursor may have a molecular weight (mw) from about 200 mw to about 5,000 mw, and may preferably have a molecular weight from about 400 mw to 1,500 mw, and may have a viscosity preferably from about 10 cps to about 400 cps. The repeating units are the same. This precursor may be used to provide a polymeric chain extender, improve toughness and to lower cure temperature down to for example room temperature curing, as well as, other features and characteristics to the cured preform and ceramic material.

The precursor may be a siloxane backbone additive, such as silanol (hydroxy) terminated polydimethyl siloxane, which formula is shown below.

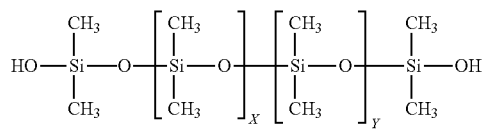

This precursor may have a molecular weight (mw) from about 400 mw to about 10,000 mw, and may preferably have a molecular weight from about 600 mw to 1,000 mw, and may have a viscosity preferably from about 30 cps to about 400 cps. The repeating units are the same. This precursor may be used to provide a polymeric chain extender, a toughening mechanism, can generate nano- and micro-scale porosity, and allows curing at room temperature, as well as other features and characteristics to the cured preform and ceramic material.

The precursor may be a siloxane backbone additive, such as silanol (hydroxy) terminated vinyl substituted dimethyl siloxane, which formula is shown below.

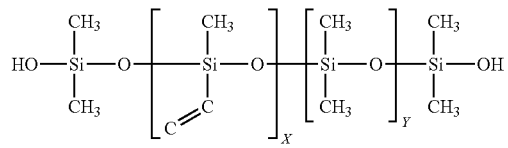

This precursor may have a molecular weight (mw) from about 400 mw to about 10,000 mw, and may preferably have a molecular weight from about 600 mw to 1,000 mw, and may have a viscosity preferably from about 30 cps to about 400 cps. The percentage of methylvinylsiloxane units "X" may be from 1% to 100%. The percentage of the dimethylsiloxane units "Y" may be from 0% to 99%. This precursor may be used, among other things, in a dual-cure system; in this manner the dual-cure can allow the use of multiple cure mechanisms in a single formulation. For example, both condensation type cure and addition type cure can be utilized. This, in turn, provides the ability to have complex cure profiles, which for example may provide for an initial cure via one type of curing and a final cure via a separate type of curing.

The precursor may be a siloxane backbone additive, such as hydrogen (hydride) terminated polydimethyl siloxane, which formula is shown below.

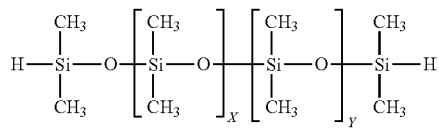

This precursor may have a molecular weight (mw) from about 200 mw to about 10,000 mw, and may preferably have a molecular weight from about 500 mw to 1,500 mw, and may have a viscosity preferably from about 20 cps to about 400 cps. The repeating units are the same. This precursor may be used to provide a polymeric chain extender, as a toughening agent, and it allows lower temperature curing, e.g., room temperature, as well as, other features and characteristics to the cured preform and ceramic material.

The precursor may be a siloxane backbone additive, such as di-phenyl terminated siloxane, which formula is shown below.

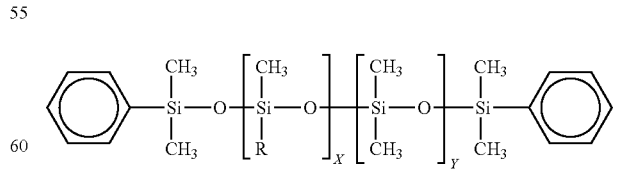

Where here R is a reactive group, such as vinyl, hydroxy, or hydride. This precursor may have a molecular weight (mw) from about 500 mw to about 2,000 mw, and may have a viscosity preferably from about 80 cps to about 300 cps. The percentage of methyl—R—siloxane units "X" may be from 1% to 100%. The percentage of the dimethylsiloxane units "Y" may be from 0% to 99%. This precursor may be used to provide a toughening agent, and to adjust the refractive index of the polymer to match the refractive index of various types of glass, to provide for example transparent fiberglass, as well as, other features and characteristics to the cured preform and ceramic material.

The precursor may be a siloxane backbone additive, such as a mono-phenyl terminated siloxane, which formulas are shown below.

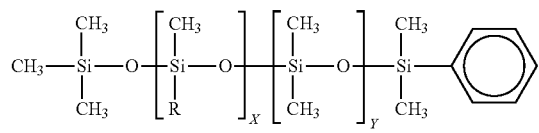

Where R is a reactive group, such as vinyl, hydroxy, or hydride. This precursor may have a molecular weight (mw) from about 500 mw to about 2,000 mw, and may have a viscosity preferably from about 80 cps to about 300 cps. The percentage of methyl—R—siloxane units "X" may be from 1% to 100%. The percentage of the dimethylsiloxane units "Y" may be from 0% to 99%. This precursor may be used to provide a toughening agent and to adjust the refractive index of the polymer to match the refractive index of various types of glass, to provide for example transparent fiberglass, as well as, other features and characteristics to the cured preform and ceramic material.

The precursor may be a siloxane backbone additive, such as diphenyl dimethyl polysiloxane, which formula is shown below.

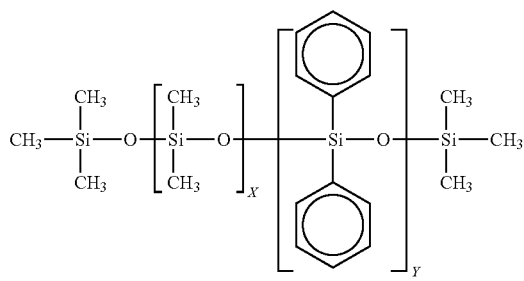

This precursor may have a molecular weight (mw) from about 500 mw to about 20,000 mw, and may have a molecular weight from about 800 to about 4,000, and may have a viscosity preferably from about 100 cps to about 800 cps. The percentage of dimethylsiloxane units "X" may be from 25% to 95%. The percentage of the diphenyl siloxane units "Y" may be from 5% to 75%. This precursor may be used to provide similar characteristics to the mono-phenyl terminated siloxane, as well as, other features and characteristics to the cured preform and ceramic material.

The precursor may be a siloxane backbone additive, such as vinyl terminated diphenyl dimethyl polysiloxane, which formula is shown below.

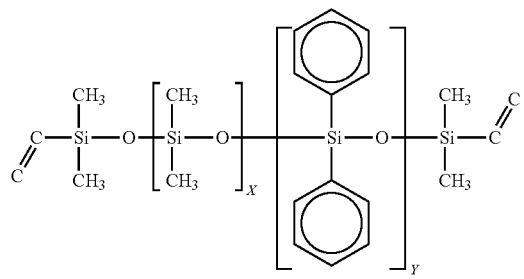

This precursor may have a molecular weight (mw) from about 400 mw to about 20,000 mw, and may have a molecular weight from about 800 to about 2,000, and may have a viscosity preferably from about 80 cps to about 600 cps. The percentage of dimethylsiloxane units "X" may be from 25% to 95%. The percentage of the diphenyl siloxane units "Y" may be from 5% to 75%. This precursor may be used to provide chain extension, toughening agent, changed or altered refractive index, and improvements to high temperature thermal stability of the cured material, as well as, other features and characteristics to the cured preform and ceramic material.

The precursor may be a siloxane backbone additive, such as hydroxy terminated diphenyl dimethyl polysiloxane, which formula is shown below.

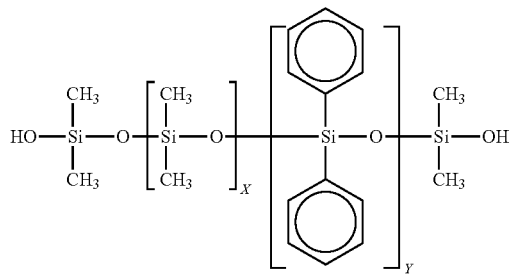

This precursor may have a molecular weight (mw) from about 400 mw to about 20,000 mw, and may have a molecular weight from about 800 to about 2,000, and may have a viscosity preferably from about 80 cps to about 400 cps. The percentage of dimethylsiloxane units "X" may be from 25% to 95%. The percentage of the diphenyl siloxane units "Y" may be from 5% to 75%. This precursor may be used to provide chain extension, toughening agent, changed or altered refractive index, and improvements to high temperature thermal stability of the cured material, can generate nano- and micro-scale porosity, as well as other features and characteristics to the cured preform and ceramic material.

A variety of cyclosiloxanes can be used as reactive molecules in the formulation. They can be described by the following nomenclature system or formula: $D_xD^*_y$, where "D" represents a dimethyl siloxy unit and "D*" represents a substituted methyl siloxy unit, where the "*" group could be vinyl, allyl, hydride, hydroxy, phenyl, styryl, alkyl, cyclopentadienyl, or other organic group, x is from 0-8, y is >=1, and x+y is from 3-8.

The precursor batch may also contain non-silicon based cross-linking agents, be the reaction product of a non-silicon based cross linking agent and a siloxane backbone additive, and combinations and variation of these. The non-silicon based cross-linking agents are intended to, and provide, the capability to cross-link during curing. For example, non-silicon based cross-linking agents that can be used include: cyclopentadiene (CP), methylcyclopentadiene (MeCP), dicyclopentadiene ("DCPD"), methyldicyclopentadiene (MeDCPD), tricyclopentadiene (TCPD), piperylene, divnylbenzene, isoprene, norbornadiene, vinylnorbornene, propenylnorbornene, isopropenylnorbornene, methylvinylnorbornene, bicyclononadiene, methylbicyclononadiene, propadiene, 4-vinylcyclohexene, 1,3-heptadiene, cycloheptadiene, 1,3-butadiene, cyclooctadiene and isomers thereof. Generally, any hydrocarbon that contains two (or more) unsaturated, C═C, bonds that can react with a Si—H, Si—OH, or other Si bond in a precursor, can be used as a cross-linking agent. Some organic materials containing oxygen, nitrogen, and sulphur may also function as cross-linking moieties.

The precursor may be a reactive monomer. These would include molecules, such as tetramethyltetravinylcyclotetrasiloxane ("TV"), which formula is shown below.

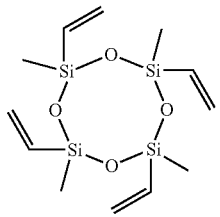 [SMILES: C=C[Si]1(C)O[Si](C)(C=C)O[Si](C)(C=C)O[Si](C)(C=C)O1]

This precursor may be used to provide a branching agent, a three-dimensional cross-linking agent, as well as, other features and characteristics to the cured preform and ceramic material. (It is also noted that in certain formulations, e.g., above 2%, and certain temperatures, e.g., about from about room temperature to about 60° C., this precursor may act as an inhibitor to cross-linking, e.g., in may inhibit the cross-linking of hydride and vinyl groups.)

The precursor may be a reactive monomer, for example, such as trivinyl cyclotetrasiloxane,

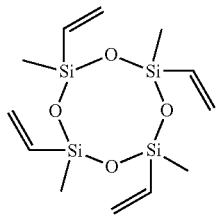 [SMILES: C=C[Si]1(C)O[Si](C)(C=C)O[Si](C)(C=C)O[Si](C)(C=C)O1]

divinyl cyclotetrasiloxane,

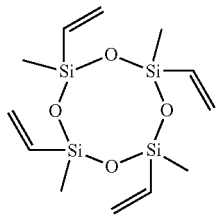 [SMILES: C=C[Si]1(C)O[Si](C)(C=C)O[Si](C)(C=C)O[Si](C)(C=C)O1]

trivinyl monohydride cyclotetrasiloxane,

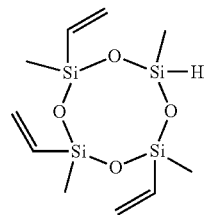 [SMILES: C=C[Si]1(C)O[SiH](C)O[Si](C)(C=C)O[Si](C)(C=C)O1]

divinyl dihydride cyclotetrasiloxane,

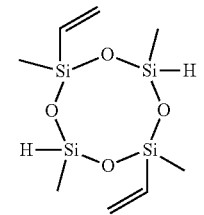 [SMILES: C=C[Si]1(C)O[SiH](C)O[Si](C)(C=C)O[SiH](C)O1]

and a hexamethyl cyclotetrasiloxane, such as,

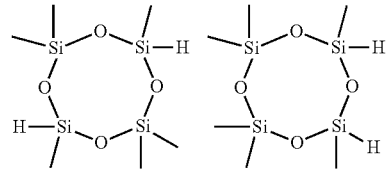

The precursor may be a silane modifier, such as vinyl phenyl methyl silane, diphenyl silane, diphenyl methyl silane, and phenyl methyl silane (some of which may be used as an end capper or end termination group). These silane modifiers can provide chain extenders and branching agents. They also improve toughness, alter refractive index, and improve high temperature cure stability of the cured material, as well as improving the strength of the cured material, among other things. A precursor, such as diphenyl methyl silane, may function as an end capping agent, that may also improve toughness, alter refractive index, and improve high temperature cure stability of the cured material, as well as, improving the strength of the cured material, among other things.

The precursor may be a reaction product of a silane modifier with a vinyl terminated siloxane backbone additive. The precursor may be a reaction product of a silane modifier with a hydroxy terminated siloxane backbone additive. The precursor may be a reaction product of a silane modifier with a hydride terminated siloxane backbone additive. The precursor may be a reaction product of a silane modifier with TV. The precursor may be a reaction product of a silane. The precursor may be a reaction product of a silane modifier with a cyclosiloxane, taking into consideration steric hindrances. The precursor may be a partially hydrolyzed tetraethyl orthosilicate, such as TES 40 or Silbond 40. The precursor may also be a methylsesquisiloxane such as SR-350 available from General Electric Company, Wilton, Conn. The precursor may also be a phenyl methyl siloxane such as 604 from Wacker Chemie AG. The precursor may also be a methylphenylvinylsiloxane, such as H62 C from Wacker Chemie AG.

The precursors may also be selected from the following: SiSiB® HF2020, TRIMETHYLSILYL TERMINATED METHYL HYDROGEN SILICONE FLUID 63148-57-2; SiSiB® HF2050 TRIMETHYLSILYL TERMINATED METHYLHYDROSILOXANE DIMETHYLSILOXANE COPOLYMER 68037-59-2; SiSiB® HF2060 HYDRIDE TERMINATED METHYLHYDROSILOXANE DIMETHYLSILOXANE COPOLYMER 69013-23-6; SiSiB® HF2038 HYDROGEN TERMINATED POLYDIPHENYL SILOXANE; SiSiB® HF2068 HYDRIDE TERMINATED METHYLHYDROSILOXANE DIMETHYLSILOXANE COPOLYMER 115487-49-5; SiSiB® HF2078 HYDRIDE TERMINATED POLY(PHENYLDIMETHYLSILOXY) SILOXANE PHENYL SILSESQUIOXANE, HYDROGEN-TERMINATED 68952-30-7; SiSiB® VF6060 VINYLDIMETHYL TERMINATED VINYLMETHYL DIMETHYL POLYSILOXANE COPOLYMERS 68083-18-1; SiSiB® VF6862 VINYLDIMETHYL TERMINATED DIMETHYL DIPHENYL POLYSILOXANE COPOLYMER 68951-96-2; SiSiB® VF6872 VINYLDIMETHYL TERMINATED DIMETHYL-METHYLVINYL-DIPHENYL POLYSILOXANE COPOLYMER; SiSiB® PC9401 1,1,3,3-TETRAMETHYL-1,3-DIVINYLDISILOXANE 2627-95-4; SiSiB® PF1070 SILANOL TERMINATED POLYDIMETHYLSILOXANE (OF1070) 70131-67-8; SiSiB® OF1070 SILANOL TERMINATED POLYDIMETHYSILOXANE 70131-67-8; OH-ENDCAPPED POLYDIMETHYLSILOXANE HYDROXY TERMINATED OLYDIMETHYLSILOXANE 73138-87-1; SiSiB® VF6030 VINYL TERMINATED POLYDIMETHYL SILOXANE 68083-19-2; and, SiSiB® HF2030 HYDROGEN TERMINATED POLYDIMETHYLSILOXANE FLUID 70900-21-9.

Thus, in additional to the forgoing type of precursors, it is contemplated that a precursor may be a compound of the following general formula.

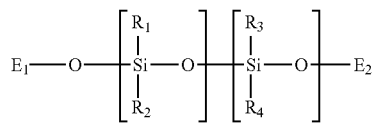

Wherein end cappers $E_1$ and $E_2$ are chosen from groups such as trimethyl silicon (—Si(CH$_3$)$_3$), dimethyl silicon hydroxy (—Si(CH$_3$)$_2$OH), dimethyl silicon hydride (—Si(CH$_3$)$_2$H), dimethyl vinyl silicon (—Si(CH$_3$)$_2$(CH=CH$_2$)), (—Si(CH$_3$)$_2$(C$_6$H$_5$)) and dimethyl alkoxy silicon (—Si(CH$_3$)$_2$(OR). The R groups $R_1$, $R_2$, $R_3$, and $R_4$ may all be different, or one or more may be the same. Thus, for example, $R_2$ is the same as $R_3$, $R_3$ is the same as $R_4$, $R_1$ and $R_2$ are different with $R_3$ and $R_4$ being the same, etc. The R groups are chosen from groups such as hydride (—H), methyl (Me)(—C), ethyl (—C—C), vinyl (—C=C), alkyl (—R)(C$_n$H$_{2n+1}$), allyl (—C—C=C), aryl ('R), phenyl (Ph) (—C$_6$H$_5$), methoxy (—O—C), ethoxy (—O—C—C), siloxy (—O—Si—R$_3$), alkoxy (—O—R), hydroxy (—O—H), phenylethyl (—C—C—C$_6$H$_5$) and methyl,phenyl-ethyl (—C—C(—C)(—C$_6$H$_5$).

In general, embodiments of formulations for polysilocarb formulations may for example have from about 0% to 50% MH, about 20% to about 99% MH, about 0% to about 30% siloxane backbone additives, about 1% to about 60% reactive monomers, about 30% to about 100% TV, and, about 0% to about 90% reaction products of a siloxane backbone additives with a silane modifier or an organic modifier reaction products.

In mixing the formulations sufficient time should be used to permit the precursors to become effectively mixed and dispersed. Generally, mixing of about 15 minutes to an hour is sufficient. Typically, the precursor formulations are relatively, and essentially, shear insensitive, and thus the type of pumps or mixing are not critical. It is further noted that in higher viscosity formulations additional mixing time may be required. The temperature of the formulations, during mixing should preferably be kept below about 45° C., and preferably about 10° C. (It is noted that these mixing conditions are for the pre-catalyzed formulations.)

The Reaction Type Process

In the reaction type process, in general, a chemical reaction is used to combine one, two or more precursors, typically in the presence of a solvent, to form a precursor formulation that is essentially made up of a single polymer that can then be, catalyzed, cured and pyrolized. This process provides the ability to build custom precursor formulations that when cured can provide plastics having unique and desirable features such as high temperature, flame resistance and retardation, strength and other features. The cured materials can also be pyrolized to form ceramics having unique features. The reaction type process allows for the predetermined balancing of different types of functionality in the end product by selecting functional groups for incorporation into the polymer that makes up the precursor formulation, e.g., phenyls which typically are not used for ceramics but have benefits for providing high temperature capabilities for plastics, and styrene which typically does not provide high temperature features for plastics but provides benefits for ceramics.

In general a custom polymer for use as a precursor formulation is made by reacting precursors in a condensation reaction to form the polymer precursor formulation. This precursor formulation is then cured into a preform through a hydrolysis reaction. The condensation reaction forms a polymer of the type shown below.

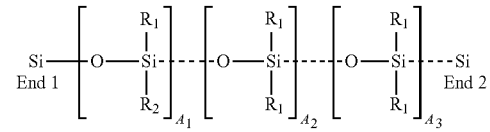

Where $R_1$ and $R_2$ in the polymeric units can be a hydride (—H), a methyl (Me)(—C), an ethyl (—C—C), a vinyl (—C=C), an alkyl (—R)(C$_n$H$_{2n+1}$), an unsaturated alkyl (—C$_n$H$_{2n-1}$), a cyclic alkyl (—C$_n$H$_{2n-1}$), an allyl (—C—C=C), a butenyl (—C$_4$H$_7$), a pentenyl (—O$_5$H$_9$), a cyclopentenyl (—O$_5$H$_7$), a methyl cyclopentenyl (—C$_5$H$_6$(CH$_3$)), a norbornenyl (—C$_X$H$_Y$, where X=7-15 and Y=9-18), an aryl ('R), a phenyl (Ph)(—C$_6$H$_5$), a cycloheptenyl (—C$_7$H$_{11}$), a cyclooctenyl (—C$_8$H$_{13}$), an ethoxy (—O—C—C), a siloxy (—O—Si—R$_3$), a methoxy (—O—C), an alkoxy, (—O—R), a hydroxy, (—O—H), a phenylethyl (—C—C—C$_6$H$_5$) a methyl,phenyl-ethyl (—C—C(—C)(—C$_6$H$_5$)) and a vinyl-phenyl-ethyl (—C—C(C$_6$H$_4$(—C=C))). $R_1$ and $R_2$ may be the same or different. The custom precursor polymers can have several different polymeric units, e.g., $A_1$, $A_2$, $A_n$, and may include as many as 10, 20 or more units, or it may contain only a single unit, for example, MHF made by the reaction process may have only a single unit.

Embodiments may include precursors, which include among others, a triethoxy methyl silane, a diethoxy methyl phenyl silane, a diethoxy methyl hydride silane, a diethoxy methyl vinyl silane, a dimethyl ethoxy vinyl silane, a diethoxy dimethyl silane. an ethoxy dimethyl phenyl silane, a diethoxy dihydride silane, a triethoxy phenyl silane, a diethoxy hydride trimethyl siloxane, a diethoxy methyl trimethyl siloxane, a trimethyl ethoxy silane, a diphenyl diethoxy silane, a dimethyl ethoxy hydride siloxane, and combinations and variations of these and other precursors, including other precursors set forth in this specification.

The end units, Si End 1 and Si End 2, can come from the precursors of dimethyl ethoxy vinyl silane, ethoxy dimethyl phenyl silane, and trimethyl ethoxy silane. Additionally, if the polymerization process is properly controlled a hydroxy end cap can be obtained from the precursors used to provide the repeating units of the polymer.

In general, the precursors are added to a vessel with ethanol (or other material to absorb heat, e.g., to provide thermal mass), an excess of water, and hydrochloric acid (or other proton source). This mixture is heated until it reaches its activation energy, after which the reaction typically is exothermic. Generally, in this reaction the water reacts with an ethoxy group of the silicon of the precursor monomer, forming a hydroxy (with ethanol as the byproduct). Once formed this hydroxy becomes subject to reaction with an ethoxy group on the silicon of another precursor monomer, resulting in a polymerization reaction. This polymerization reaction is continued until the desired chain length(s) is built.

Control factors for determining chain length, among others, are: the monomers chosen (generally, the smaller the monomers the more that can be added before they begin to coil around and bond to themselves); the amount and point in the reaction where end cappers are introduced; and the amount of water and the rate of addition, among others. Thus, the chain lengths can be from about 180 mw (viscosity about 5 cps) to about 65,000 mw (viscosity of about 10,000 cps), greater than about 1000 mw, greater than about 10,000 mw, greater than about 50,000 mw and greater. Further, the polymerized precursor formulation may, and typically does, have polymers of different molecular weights, which can be predetermined to provide formulation, cured, and ceramic product performance features.

Upon completion of the polymerization reaction the material is transferred into a separation apparatus, e.g., a separation funnel, which has an amount of deionized water that, for example, is from about 1.2x to about 1.5x the mass of the material. This mixture is vigorously stirred for about less than 1 minute and preferably from about 5 to 30 seconds. Once stirred the material is allowed to settle and separate, which may take from about 1 to 2 hours. The polymer is the higher density material and is removed from the vessel. This removed polymer is then dried by either warming in a shallow tray at 90° C. for about two hours; or, preferably, is passed through a wiped film distillation apparatus, to remove any residual water and ethanol. Alternatively, sodium bicarbonate sufficient to buffer the aqueous layer to a pH of about 4 to about 7 is added. It is further understood that other, and commercial, manners of mixing, reacting and separating the polymer from the material may be employed.

Preferably a catalyst is used in the curing process of the polymer precursor formulations from the reaction type process. The same polymers, as used for curing the precursor formulations from the mixing type process can be used. It is noted that, generally unlike the mixing type formulations, a catalyst is not necessarily required to cure a reaction type polymer. Inhibitors may also be used. However, if a catalyst is not used, reaction time and rates will be slower. The curing and the pyrolysis of the cured material from the reaction process is essentially the same as the curing and pyrolysis of the cured material from the mixing process and the reaction blending process.

The reaction type process can be conducted under numerous types of atmospheres and conditions, e.g., air, inert, $N_2$, Argon, flowing gas, static gas, reduced pressure, ambient pressure, elevated pressure, and combinations and variations of these.

The Reaction Blending Type Process

In the reaction blending type process precursor are reacted to from a precursor formulation, in the absence of a solvent.

For example, an embodiment of a reaction blending type process has a precursor formulation that is prepared from MHF and Dicyclopentadiene ("DCPD"). Using the reactive blending process a MHF/DCPD polymer is created and this polymer is used as a precursor formulation. (It can be used alone to form a cured or pyrolized product, or as a precursor in the mixing or reaction processes.) MHF of known molecular weight and hydride equivalent mass; "P01" (P01 is a 2% Pt(0) tetravinylcyclotetrasiloxane complex (e.g., tetramethyltetravinylcyclotetrasiloxane) in tetravinylcyclotetrasiloxane, diluted 20+ with tetravinylcyclotetrasiloxane to 0.1% of Pt(0) complex. In this manner 10 ppm Pt is provided for every 1% loading of bulk cat.) catalyst 0.20 wt % of MHF starting material (with known active equivalent weight), from 40 to 90%; and Dicyclopentadiene with 83% purity, from 10 to 60% are utilized. In an embodiment of the process, a sealable reaction vessel, with a mixer, can be used for the reaction. The reaction is conducted in the sealed vessel, in air; although other types of atmosphere can be utilized. Preferably, the reaction is conducted at atmospheric pressure, but higher and lower pressures can be utilized. Additionally, the reaction blending type process can be conducted under numerous types of atmospheres and conditions, e.g., air, inert, $N_2$, Argon, flowing gas, static gas, reduced pressure, ambient pressure, elevated pressure, and combinations and variations of these.

In an embodiment, 850 grams of MHF (85% of total polymer mixture) is added to reaction vessel and heated to about 50° C. Once this temperature is reached the heater is turned off, and 0.20% by weight P01 Platinum catalyst is added to the MHF in the reaction vessel. Typically, upon addition of the catalyst bubbles will form and temp will initially rise approximately 2-20° C.

When the temperature begins to fall, about 150 g of DCPD (15 wt % of total polymer mixture) is added to the reaction vessel. The temperature may drop an additional amount, e.g., around 5-7° C.

At this point in the reaction process the temperature of the reaction vessel is controlled to, maintain a predetermined temperature profile over time, and to manage the temperature increase that may be accompanied by an exotherm. Preferably, the temperature of the reaction vessel is regulated, monitored and controlled throughout the process.

In an embodiment of the MHF/DCPD embodiment of the reaction process, the temperature profile can be as follows: let temperature reach about 80° C. (may take ~15-40 min, depending upon the amount of materials present); temperature will then increase and peak at ~104° C., as soon as temperature begins to drop, the heater set temperature is increased to 100° C. and the temperature of the reaction mixture is monitored to ensure the polymer temp stays above 80° C. for a minimum total of about 2 hours and a maximum total of about 4 hours. After 2-4 hours above 80°

C., the heater is turned off, and the polymer is cooled to ambient. It being understood that in larger and smaller batches, continuous, semi-continuous, and other type processes the temperature and time profile may be different.

In larger scale, and commercial operations, batch, continuous, and combinations of these, may be used. Industrial factory automation and control systems can be utilized to control the reaction, temperature profiles and other processes during the reaction.

Table C sets forth various embodiments of reaction blending processes.

In making the precursor formulation into a structure, or preform, the precursor formulation, e.g., polysilocarb formulation, can be, for example, formed using the following techniques: spraying, spray drying, atomization, nebulization, phase change separation, flowing, thermal spraying, drawing, dripping, forming droplets in liquid and liquid-surfactant systems, painting, molding, forming, extruding, spinning, ultrasound, vibrating, solution polymerization, emulsion polymerization, micro-emulsion polymerization, injecting, injection molding, or otherwise manipulated into essentially any volumetric shape. These volumetric shapes

TABLE C

| Material Name | degree of polymerization | Equivalents Si/mole | Equivalents O/mole | Equivalents H/mol | Equivalents Vi/mol | Equivalents methyl/mole | Equivalents C/mole | MW | grams/ mole of vinyl |
|---|---|---|---|---|---|---|---|---|---|
| tetramethylcyclotetrasiloxane ($D_4$) | 4 | 4 | 4 | 4 | 0 | 4 | 4 | 240.51 | |
| MHF | 33 | 35 | 34 | 33 | 0 | 39 | 39 | 2145.345 | |
| VMF | 5 | 7 | 6 | 0 | 5 | 11 | 21 | 592.959 | 118.59 |
| TV | 4 | 4 | 4 | 0 | 4 | 4 | 12 | 344.52 | 86.13 |
| VT 0200 | 125 | 127 | 126 | 0 | 2 | 254 | 258 | 9451.206 | 4725.60 |
| VT 0020 | 24 | 26 | 25 | 0 | 2 | 52 | 56 | 1965.187 | 982.59 |
| VT 0080 | 79 | 81 | 80 | 0 | 2 | 162 | 166 | 6041.732 | 3020.87 |
| Styrene | | | | | 2 | | | 104.15 | 52.08 |
| Dicyclopentadiene | | | | | 2 | | | 132.2 | 66.10 |
| 1,4-divinylbenzene | | | | | 2 | | | 130.19 | 65.10 |
| isoprene | | | | | 2 | | | 62.12 | 31.06 |
| 1,3 Butadiene | | | | | 2 | | | 54.09 | 27.05 |
| Catalyst 10 ppm Pt | | | | | | | | | |
| Catalyst LP 231 | | | | | | | | | |

In the above table, the "degree of polymerization" is the number of monomer units, or repeat units, that are attached together to form the polymer. "Equivalents _/mol" refers to the molar equivalents. "Grams/mole of vinyl" refers to the amount of a given polymer needed to provide 1 molar equivalent of vinyl functionality. "VMH" refers to methyl vinyl fluid, a linear vinyl material from the ethoxy process, which can be a substitute for TV. The numbers "0200" etc. for VT are the viscosity in centipoise for that particular VT.

Curing and Pyrolysis

Precursor formulations, including the polysilocarb precursor formulations from the above types of processes, as well as others, can be cured to form a solid, semi-sold, or plastic like material. Typically, the precursor formulations are spread, shaped, or otherwise formed into a preform, which would include any volumetric structure, or shape, including thin and thick films. In curing, the polysilocarb precursor formulation may be processed through an initial cure, to provide a partially cured material, which may also be referred to, for example, as a preform, green material, or green cure (not implying anything about the material's color). The green material may then be further cured. Thus, one or more curing steps may be used. The material may be "end cured," i.e., being cured to that point at which the material has the necessary physical strength and other properties for its intended purpose. The amount of curing may be to a final cure (or "hard cure"), i.e., that point at which all, or essentially all, of the chemical reaction has stopped (as measured, for example, by the absence of reactive groups in the material, or the leveling off of the decrease in reactive groups over time). Thus, the material may be cured to varying degrees, depending upon its intended use and purpose. For example, in some situations the end cure and the hard cure may be the same. Curing conditions such as atmosphere and temperature may affect the composition of the cured material.

may include for example, the following: spheres, pellets, rings, lenses, disks, panels, cones, frustoconical shapes, squares, rectangles, trusses, angles, channels, hollow sealed chambers, hollow spheres, blocks, sheets, coatings, films, skins, particulates, beams, rods, angles, slabs, columns, fibers, staple fibers, tubes, cups, pipes, and combinations and various of these and other more complex shapes, both engineering and architectural.

The forming step, the curing steps, and the pyrolysis steps may be conducted in batch processes, serially, continuously, with time delays (e.g., material is stored or held between steps), and combinations and variations of these and other types of processing sequences. Further, the precursors can be partially cured, or the cure process can be initiated and on going, prior to the precursor being formed into a volumetric shape. These steps, and their various combinations may be, and in some embodiments preferably are, conducted under controlled and predetermined conditions (e.g., the material is exposed to a predetermined atmosphere, and temperature profile during the entirely of its processing, e.g., reduced oxygen, temperature of cured preform held at about 140° C. prior to pyrolysis). It should be further understood that the system, equipment, or processing steps, for forming, curing and pyrolyzing may be the same equipment, continuous equipment, batch and linked equipment, and combinations and variations of these and other types of industrial processes. Thus, for example, a spray drying technique could form cured particles that are feed directly into a fluidized bed reactor for pyrolysis.

The polysilocarb precursor formulations can be made into neat, non-reinforced, non-filled, composite, reinforced, and filled structures, intermediates, end products, and combinations and variations of these and other compositional types of materials. Further, these structures, intermediates and end products can be cured (e.g., green cured, end cured, or hard cured), uncured, pyrolyzed to a ceramic, and combinations and variations of these (e.g., a cured material may be filled with pyrolized material derived from the same polysilocarb as the cured material).

The precursor formulations may be used to form a "neat" material, (by "neat" material it is meant that all, and essentially all of the structure is made from the precursor material or unfilled formulation; and thus, there are no fillers or reinforcements).

The polysilocarb precursor formulations may be used to coat or impregnate a woven or non-woven fabric, made from for example carbon fiber, glass fibers or fibers made from a polysilocarb precursor formulation (the same or different formulation), to from a prepreg material. Thus, the polysilocarb precursor formulations may be used to form composite materials, e.g., reinforced products. For example, the formulation may be flowed into, impregnated into, absorbed by or otherwise combined with a reinforcing material, such as carbon fibers, glass fiber, woven fabric, grapheme, carbon nanotubes, thin films, precipitates, sand, non-woven fabric, copped fibers, fibers, rope, braided structures, ceramic powders, glass powders, carbon powders, graphite powders, ceramic fibers, metal powders, carbide pellets or components, staple fibers, tow, nanostructures of the above, polymer derived ceramics, any other material that meets the temperature requirements of the process and end product, and combinations and variations of these. The reinforcing material may also be made from, or derived from the same material as the formulation that has been formed into a fiber and pyrolized into a ceramic, or it may be made from a different precursor formulation material, which has been formed into a fiber and pyrolized into a ceramic.

The polysilocarb precursor formulation may be used to form a filled material. A filled material would be any material having other solid, or semi-solid, materials added to the polysilocarb precursor formulation. The filler material may be selected to provide certain features to the cured product, the ceramic product and both. These features may relate to, or be, for example, aesthetic, tactile, thermal, density, radiation, chemical, cost, magnetic, electric, and combinations and variations of these and other features. These features may be in addition to strength. Thus, the filler material may not affect the strength of the cured or ceramic material, it may add strength, or could even reduce strength in some situations. The filler material could impart color, magnetic capabilities, fire resistances, flame retardance, heat resistance, electrical conductivity, anti-static, optical properties (e.g., reflectivity, refractivity and iridescence), aesthetic properties (such as stone like appearance in building products), chemical resistivity, corrosion resistance, wear resistance, reduced cost, abrasions resistance, thermal insulation, UV stability, UV protective, and other features that may be desirable, necessary, and both, in the end product or material. Thus, filler materials could include carbon black, copper lead wires, thermal conductive fillers, electrically conductive fillers, lead, optical fibers, ceramic colorants, pigments, oxides, sand, dyes, powders, ceramic fines, polymer derived ceramic particles, pore-formers, carbosilanes, silanes, silazanes, silicon carbide, carbosilazanes, siloxane, powders, ceramic powders, metals, metal complexes, carbon, tow, fibers, staple fibers, boron containing materials, milled fibers, glass, glass fiber, fiber glass, and nanostructures (including nanostructures of the forgoing) to name a few.

The polysilocarb formulation and products derived or made from that formulation may have metals and metal complexes. Filled materials would include reinforced materials. In many cases, cured, as well as pyrolized polysilocarb filled materials can be viewed as composite materials. Generally, under this view, the polysilocarb would constitute the bulk or matrix phase, (e.g., a continuous, or substantially continuous phase), and the filler would constitute the dispersed (e.g., non-continuous), phase. Depending upon the particular application, product or end use, the filler can be evenly distributed in the precursor formulation, unevenly distributed, distributed over a predetermined and controlled distribution gradient (such as from a predetermined rate of settling), and can have different amounts in different formulations, which can then be formed into a product having a predetermined amounts of filler in predetermined areas (e.g., striated layers having different filler concentration). It should be noted, however, that by referring to a material as "filled" or "reinforced" it does not imply that the majority (either by weight, volume, or both) of that material is the polysilcocarb. Thus, generally, the ratio (either weight or volume) of polysilocarb to filler material could be from about 0.1:99.9 to 99.9:0.1.

The polysilocarb precursor formulations may be used to form non-reinforced materials, which are materials that are made of primarily, essentially, and preferably only from the precursor materials; but may also include formulations having fillers or additives that do not impart strength.

The curing may be done at standard ambient temperature and pressure ("SATP", 1 atmosphere, 25° C.), at temperatures above or below that temperature, at pressures above or below that pressure, and over varying time periods. The curing can be conducted over various heatings, rate of heating, and temperature profiles (e.g., hold times and temperatures, continuous temperature change, cycled temperature change, e.g., heating followed by maintaining, cooling, reheating, etc.). The time for the curing can be from a few seconds (e.g., less than about 1 second, less than 5 seconds), to less than a minute, to minutes, to hours, to days (or potentially longer). The curing may also be conducted in any type of surrounding environment, including for example, gas, liquid, air, water, surfactant containing liquid, inert atmospheres, $N_2$, Argon, flowing gas (e.g., sweep gas), static gas, reduced $O_2$, reduced pressure, elevated pressure, ambient pressure, controlled partial pressure and combinations and variations of these and other processing conditions. For high purity materials, the furnace, containers, handling equipment, atmosphere, and other components of the curing apparatus and process are clean, essentially free from, and do not contribute any elements or materials, that would be considered impurities or contaminants, to the cured material. In an embodiment, the curing environment, e.g., the furnace, the atmosphere, the container and combinations and variations of these can have materials that contribute to or effect, for example, the composition, catalysis, stoichiometry, features, performance and combinations and variations of these in the preform, the ceramic and the final applications or products.

Preferably, in embodiments of the curing process, the curing takes place at temperatures in the range of from about 5° C. or more, from about 20° C. to about 250° C., from about 20° C. to about 150° C., from about 75° C. to about 125° C., and from about 80° C. to 90° C. Although higher and lower temperatures and various heating profiles, (e.g., rate of temperature change over time ("ramp rate", e.g., Δ degrees/time), hold times, and temperatures) can be utilized.

The cure conditions, e.g., temperature, time, ramp rate, may be dependent upon, and in some embodiments can be predetermined, in whole or in part, by the formulation to match, for example the size of the preform, the shape of the preform, or the mold holding the preform to prevent stress cracking, off gassing, or other phenomena associated with the curing process. Further, the curing conditions may be such as to take advantage of, preferably in a controlled manner, what may have previously been perceived as problems associated with the curing process. Thus, for example, off gassing may be used to create a foam material having either open or closed structure. Similarly, curing conditions can be used to create or control the microstructure and the nanostructure of the material. In general, the curing conditions can be used to affect, control or modify the kinetics and thermodynamics of the process, which can affect morphology, performance, features and functions, among other things.

Upon curing the polysilocarb precursor formulation a cross linking reaction takes place that provides in some embodiments a cross-linked structure having, among other things, an —$R_1$—Si—C—C—Si—O—Si—C—C—Si—$R_2$— where $R_1$ and $R_2$ vary depending upon, and are based upon, the precursors used in the formulation. In an embodiment of the cured materials they may have a cross-linked structure having 3-coordinated silicon centers to another silicon atom, being separated by fewer than 5 atoms between silicons.

During the curing process some formulations may exhibit an exotherm, i.e., a self heating reaction, that can produce a small amount of heat to assist or drive the curing reaction, or that may produce a large amount of heat that may need to be managed and removed in order to avoid problems, such as stress fractures. During the cure off gassing typically occurs and results in a loss of material, which loss is defined generally by the amount of material remaining, e.g., cure yield. Embodiments of the formulations, cure conditions, and polysilocarb precursor formulations of embodiments of the present inventions can have cure yields of at least about 90%, about 92%, about 100%. In fact, with air cures the materials may have cure yields above 100%, e.g., about 101-105%, as a result of oxygen being absorbed from the air. Additionally, during curing the material typically shrinks, this shrinkage may be, depending upon the formulation, cure conditions, and the nature of the preform shape, and whether the preform is reinforced, filled, neat or unreinforced, from about 20%, less than 20%, less than about 15%, less than about 5%, less than about 1%, less than about 0.5%, less than about 0.25% and smaller.

Curing of the preform may be accomplished by any type of heating apparatus, or mechanisms, techniques, or morphologies that has the requisite level of temperature and environmental control, for example, heated water baths, electric furnaces, microwaves, gas furnaces, furnaces, forced heated air, towers, spray drying, falling film reactors, fluidized bed reactors, lasers, indirect heating elements, direct heating, infrared heating, UV irradiation, RF furnace, in-situ during emulsification via high shear mixing, in-situ during emulsification via ultrasonication.

The cured preforms, either unreinforced, neat, filled or reinforced, may be used as a stand alone product, an end product, a final product, or a preliminary product for which later machining or processing may be performed on. The preforms may also be subject to pyrolysis, which converts the preform material into a ceramic.

In pyrolizing the preform, or cured structure, or cured material, it is heated to about 600° C. to about 2,300° C.; from about 650° C. to about 1,200° C., from about 800° C. to about 1300° C., from about 900° C. to about 1200° C. and from about 950° C. to 1150° C. At these temperatures typically all organic structures are either removed or combined with the inorganic constituents to form a ceramic. Typically at temperatures in the about 650° C. to 1,200° C. range the resulting material is an amorphous glassy ceramic. When heated above about 1,200° C. the material typically may from nano crystalline structures, or micro crystalline structures, such as SiC, $Si_3N_4$, SiCN, β SiC, and above 1,900° C. an αSiC structure may form, and at and above 2,200° C. α SiC is typically formed. The pyrolized, e.g., ceramic materials can be single crystal, polycrystalline, amorphous, and combinations, variations and subgroups of these and other types of morphologies.

The pyrolysis may be conducted under many different heating and environmental conditions, which preferably include thermo control, kinetic control and combinations and variations of these, among other things. For example, the pyrolysis may have various heating ramp rates, heating cycles and environmental conditions. In some embodiments, the temperature may be raised, and held a predetermined temperature, to assist with known transitions (e.g., gassing, volatilization, molecular rearrangements, etc.) and then elevated to the next hold temperature corresponding to the next known transition. The pyrolysis may take place in reducing atmospheres, oxidative atmospheres, low $O_2$, gas rich (e.g., within or directly adjacent to a flame), inert, $N_2$, Argon, air, reduced pressure, ambient pressure, elevated pressure, flowing gas (e.g., sweep gas, having a flow rate for example of from about from about 15.0 GHSV to about 0.1 GHSV, from about 6.3 GHSV to about 3.1 GHSV, and at about 3.9 GHSV), static gas, and combinations and variations of these.

The pyrolysis is conducted over a time period that preferably results in the complete pyrolysis of the preform. For high purity materials, the furnace, containers, handling equipment, and other components of the pyrolysis apparatus are clean, essentially free from, free from and do not contribute any elements or materials, that would be considered impurities or contaminants, to the pyrolized material. A constant flow rate of "sweeping" gas can help purge the furnace during volatile generation. In an embodiment, the pyrolysis environment, e.g., the furnace, the atmosphere, the container and combinations and variations of these, can have materials that contribute to or effect, for example, the composition, stoichiometry, features, performance and combinations and variations of these in the ceramic and the final applications or products.

During pyrolysis material may be lost through off gassing. The amount of material remaining at the end of a pyrolysis step, or cycle, is referred to as char yield (or pyrolysis yield). The formulations and polysilocarb precursor formulations of embodiments of the present formulations can have char yields for SiOC formation of at least about 60%, about 70%, about 80%, and at least about 90%, at least about 91% and greater. In fact, with air pyrolysis the materials may have char yields well above 91%, which can approach 100%. In order to avoid the degradation of the material in an air pyrolysis (noting that typically pyrolysis is conducted in inert atmospheres, reduced oxygen atmosphere, essentially inert atmosphere, minimal oxygen atmospheres, and combinations and variations of these) specifically tailored formulations can be used. For example, formulations high in phenyl content (at least about 11%, and preferably at least about 20% by weight phenyls), formulations high in allyl content (at least about 15% to about 60%) can be used for air pyrolysis to mitigate the degradation of the material.

The initial or first pyrolysis step for SiOC formation, in some embodiments and for some uses, generally yields a structure that is not very dense, and for example, may not reached the density required for its intended use. However, in some examples, such as the use of lightweight spheres, proppants, pigments, and others, the first pyrolysis may be, and is typically sufficient. Thus, generally a reinfiltration process may be performed on the pyrolized material, to add in additional polysilocarb precursor formulation material, to fill in, or fill, the voids and spaces in the structure. This reinfiltrated material may then be cured and repyrolized. (In some embodiments, the reinfiltrated materials is cured, but not pyrolized.) This process of pyrolization, reinfiltration may be repeated, through one, two, three, and up to 10 or more times to obtain the desired density of the final product.

In some embodiments, upon pyrolization, graphenic, graphitic, amorphous carbon structures and combinations and variations of these are present in the Si—O—C ceramic. A distribution of silicon species, consisting of SiOxCy structures, which result in SiO4, SiO3C, SiO2C2, SiOC3, and SiC4 are formed in varying ratios, arising from the precursor choice and their processing history. Carbon is generally bound between neighboring carbons and/or to a Silicon atom. In general, in the ceramic state, carbon is largely not coordinated to an oxygen atom, thus oxygen is largely coordinated to silicon The pyrolysis may be conducted in any heating apparatus that maintains the request temperature and environmental controls. Thus, for example pyrolysis may be done with gas fired furnaces, electric furnaces, direct heating, indirect heating, fluidized beds, kilns, tunnel kilns, box kilns, shuttle kilns, coking type apparatus, lasers, microwaves, and combinations and variations of these and other heating apparatus and systems that can obtain the request temperatures for pyrolysis.

Custom and predetermined control of when chemical reactions, arrangements and rearrangements, occur in the various stages of the process from raw material to final end product can provide for reduced costs, increased process control, increased reliability, increased efficiency, enhanced product features, increased purity, and combinations and variation of these and other benefits. The sequencing of when these transformations take place can be based upon the processing or making of precursors, and the processing or making of precursor formulations; and may also be based upon cure and pyrolysis conditions. Further, the custom and predetermined selection of these steps, formulations and conditions, can provide enhanced product and processing features through the various transformations, e.g., chemical reactions; molecular arrangements and rearrangements; and microstructure arrangements and rearrangements.

At various points during the manufacturing process, the polymer derived ceramic structures, e.g., polysilocarb structures, intermediates and end products, and combinations and variations of these, may be machined, milled, molded, shaped, drilled, etched, or otherwise mechanically processed and shaped.

Starting materials, precursor formulations, polysilocarb precursor formulations, as well as, methods of formulating, making, forming, curing and pyrolizing, precursor materials to form polymer derived materials, structures and ceramics, are set forth in Published US Patent Applications, Publication Nos. 2014/0343220, 2014/0274658, and 2014/0326453, and US Patent Applications, Ser. Nos. 61/946,598, 62/055,397 and 62/106,094, the entire disclosures of each of which are incorporated herein by reference.

In preferred embodiments of the polysilocarb derived ceramic pigments the amounts of Si, 0, C for the total amount of pigment are set forth in the Table 4.

TABLE 4

|  | Si | | O | | C | |
| --- | --- | --- | --- | --- | --- | --- |
|  | Lo | Hi | Lo | Hi | Lo | Hi |
| Wt % | 35.00% | 50.00% | 10.00% | 35.00% | 5.00% | 30.00% |
| Mole Ratio | 1.000 | 1.429 | 0.502 | 1.755 | 0.334 | 2.004 |
| Mole % | 15.358% | 63.095% | 8.821% | 56.819% | 6.339% | 57.170% |

In general, embodiments of the pyrolized ceramic polysilocarb pigments can have about 30% to about 60% Si, can have about 5% to about 40% O, and can have about 3% to about 35% carbon. Greater and lesser amounts are also contemplated.

The type of carbon present in preferred embodiments of the polysilocarb derived ceramic pigments can be free carbon, (e.g., turbostratic, amorphous, graphenic, graphitic forms of carbon) and Carbon that is bound to Silicon. Embodiments having preferred amounts of free carbon and Silicon-bound-Carbon (Si—C) are set forth in Table 5.

TABLE 5

| Embodiment | % Free Carbon | % Si—C type |
| --- | --- | --- |
| 1 | 64.86 | 35.14 |
| 2 | 63.16 | 36.85 |
| 3 | 67.02 | 32.98 |
| 4 | 58.59 | 41.41 |
| 5 | 65.70 | 31.66 |
| 6 | 62.72 | 30.82 |
| 7 | 61.68 | 34.44 |
| 8 | 69.25 | 27.26 |
| 9 | 60.00 | 27.54 |

Generally, embodiments of polysilocarb derived ceramic pigments can have from about 20% free carbon to about 80% free carbon, and from about 20% Si—C bonded carbon to about 80% Si—C bonded carbon. Greater and lesser amounts are also contemplated.

Typically, embodiments of the pyrolized ceramic polysilocarb pigments can have other elements present, such as Nitrogen and Hydrogen. Embodiments can have the amounts of these other materials as set out in Table 6. (Note that these are typical for embodiments of net materials. If fillers, additives, or other materials are combined with or into the precursor formulation; then such materials can generally be present to a greater or lesser extent in the pyrolized ceramic material)

TABLE 6

|  | H | | N | |
| --- | --- | --- | --- | --- |
|  | Lo | Hi | Lo | Hi |
| Wt % | 0.00% | 2.20% | 0% | 2% |
| Mole Ratio | 0.000 | 1.751 | 0 | 0.1 |
| Mole % | 0.000% | 48.827% | 0% | 3% |

The polysilocarb derived ceramic pigments can exhibit sparkle, and impart sparkle to a coating. The degree and effect of sparkle can be predetermined by such factors as for example the surface exposure during pyrolysis, heat profile, and the type of gas (nitrogen, argon etc.) used during pyrolysis.

EXAMPLES

The following examples are provided to illustrate various embodiments of, among other things, precursor formulations, processes, methods, apparatus, articles, compositions, and applications of the present inventions. These examples are for illustrative purposes, and should not be viewed as, and do not otherwise limit the scope of the present inventions. The percentages used, unless specified otherwise, are weight percent of the total batch, pigment, formulation or structure.

Example 1

A polymer derived ceramic black pigment having 41% Si, 31% O, and 27% C (with 27.5% of the carbon being the Si—C bonded type, and the remaining carbon being the graphitic type) has the following properties.

Physical and Chemical Properties

| | |
|---|---|
| Particle Size (D50) capabilities | 1-150 μm |
| Specific Gravity | 2.10 |
| Bulk Density, lbs/ft$^3$ | 78 |
| g/cc | 1.25 |
| Morphology | Angular - Fragmented |
| Solubility in 12/3 HCL/HF Acid (% weight loss) | 0.4 |

Masstone (Typical) 800 Series

| | |
|---|---|
| DFT (mil/μ) | 0.8/20 |
| Gloss 20° | 74.6 |
| Gloss 60° | 97.4 |
| Color Development* | |
| L* | 4.64 |
| a* | 0.25 |
| B* | 0.95 |

*commercial automotive binder system.

Weather Test 500 hr.

| | |
|---|---|
| Chalking | none |
| Blistering | none |
| Whitening | none |
| Color Development* | |
| L (init./final) | 4.64/4.51 |
| a (init./final) | 0.25/0.17 |
| b (init./final) | 0.95/0.97 |
| Gloss Retention | 98.4% |

*QUV per ASTM G154.

Environmental Properties

| | |
|---|---|
| Salt Spray (500 hrs.) | Pass |
| Conductivity (δ) | <10$^{-3}$ |
| Scratch resistance (ISO 1518 stylus) To 5 Kg weight | No cut (pass) |
| Pencil Hardness | HB |

Example 2

A polymer derived ceramic black pigment having 45% Si, 22% O, and 33% C (with 34.4% of the carbon being the Si—C bonded type, and the remaining carbon being the graphitic type) and an agglomerate size of 10 μm and a particle size of 0.1 μm.

Example 3

A polymer derived ceramic black pigment having 44% Si, 31% O, and 25% C (with 27.3% of the carbon being the Si—C bonded type, and the remaining carbon being the graphitic type) and an agglomerate size of 15 μm and a particle size of 1 μm.

Example 4

A polymer derived ceramic black pigment having 50% Si, 20% O, and 30% C (with 25% of the carbon being the Si—C bonded type, and the remaining carbon being the graphitic type) and an agglomerate size of 10 μm and a particle size of 0.5 μm.

Example 5

A polysilocarb batch having 75% MH, 15% TV, 10% VT and 1% catalyst (10 ppm platinum and 0.5% Luperox 231 peroxide) is cured and pyrolized to form black ceramic pigment.

Example 6

A polysilocarb batch having 70% MH, 20% TV, 10% VT and 1% catalyst (10 ppm platinum and 0.5% Luperox 231 peroxide) is cured and pyrolized to form black ceramic pigment.

Example 7

A polysilocarb batch having 50% by volume carbon black is added to a polysilocarb batch having 70% MH, 20% TV, 10% VT and 1% catalyst (10 ppm platinum and 0.5% Luperox 231 peroxide) is cured and pyrolized to form black ceramic filled pigment.

Example 8

A polysilocarb batch having 70% of the MH precursor (molecular weight of about 800) and 30% of the TV precursor is cured and pyrolized to form black ceramic pigment.

Example 9

A polysilocarb batch having 10% of the MH precursor (molecular weight of about 800), 73% of the methyl terminated phenylethyl polysiloxane precursor (molecular weight of about 1,000), and 16% of the TV precursor, and 1% of the OH terminated is cured and pyrolized to form black ceramic pigment.

Example 10

A polysilocarb reaction blend batch having 85/15 MHF/DCPD is cured and pyrolized in a single heating step in a gas rich furnace at 1,100° C. to form black ceramic pigment.

Example 11

A polysilocarb reaction blend batch having 85/15 MHF/DCPD with 1% P01 catalyst and 1% peroxide catalyst is cured at 100° C. in a reduced oxygen atmosphere and the cure material is then pyrolized in a reduced pressure argon flowing environment at 1,200° C. to form black ceramic pigment.

Example 12

A polysilocarb reaction blend batch having 85/15 MHF/DCPD with 1% P01 catalyst and 3% TV (which functions as a curie rate accelerator) is cured and pyrolized to form a black ceramic pigment.

Example 13

A polysilocarb reaction blend batch having 65/35 MHF/DCPD is cured and pyrolized to form a black ceramic pigment.

Example 14

A polysilocarb reaction blend batch having 70/30 MHF/DCPD is cured and pyrolized to form a black ceramic pigment.

Example 15

A polysilocarb reaction blend batch having 60/40 MHF/DCPD is cured and pyrolized to form a black ceramic pigment.

Example 16

A polysilocarb batch having 50-65% MHF; 5-10% Tetravinyl; and 25-40% Diene (Diene=Dicyclopentadiene or Isoprene or Butadiene), preferably catalyzed with P01 or other Platinum catalyst is cured and pyrolized to form a black ceramic pigment.

Example 17

A polysilocarb batch having 60-80% MHF and 20-40% Isoprene, preferably catalyzed with P01 or other Platinum catalyst is cured and pyrolized to form a black ceramic pigment.

Example 18

A polysilocarb batch having 50-65% MHF and 35-50% Tetravinyl, preferably catalyzed with P01 or other Platinum catalyst is cured and pyrolized to form a black ceramic pigment.

Example 19

A polysilocarb reaction blend batch having 85/15 MHF/DCPD, and preferably using P01 and Luperox® 231 catalysts is cured and pyrolized to form a black ceramic pigment.

Example 20

A polysilocarb reaction blend batch having 65/35 MHF/DCPD, and preferably using P01 and Luperox® 231 catalysts is cured and pyrolized to form a black ceramic pigment.

Example 21

A polysilocarb batch having 46% MHF and 34% TV and 20 VT, with P01 catalyst is cured and pyrolized to form a black ceramic pigment.

Example 22

A polysilocarb reaction blend batch having 50/50 MHF/DCPD with 4% TV and 5 ppm Pt catalyst is cured and pyrolized to form a black ceramic pigment.

Example 23

Using the reaction type process a precursor formulation was made using the following formulation. The temperature of the reaction was maintained at 61° C. for 21 hours.

| Reactant or Solvent | Mass | % of Total | MW | Moles of Reactant/solvent | % of Total Moles of Silane | Moles of Si | Moles of EtOH |
|---|---|---|---|---|---|---|---|
| Methyltriethoxysilane | 120.00 | 19.5% | 178.30 | 0.67 | 47.43% | 0.67 | 2.02 |
| Phenylmethyldiethoxysilane | 0.00 | 0.0% | 210.35 | — | 0.00% | — | — |
| Dimethyldiethoxysilane | 70.00 | 11.4% | 148.28 | 0.47 | 33.27% | 0.47 | 0.94 |
| Methyldiethoxysilane | 20.00 | 3.3% | 134.25 | 0.15 | 10.50% | 0.15 | 0.30 |
| Vinylmethyldiethoxysilane | 20.00 | 3.3% | 160.29 | 0.12 | 8.79% | 0.12 | 0.25 |
| Trimethyethoxysilane | 0.00 | 0.0% | 118.25 | — | 0.00% | — | — |
| Hexane in hydrolyzer | 0.00 | 0.0% | 86.18 | — | | | |
| Acetone in hydrolyzer | 320.00 | 52.0% | 58.08 | 5.51 | | | |
| Ethanol in hydrolyzer | 0.00 | 0.0% | 46.07 | — | | | |
| Water in hydrolyzer | 64.00 | 10.4% | 18.00 | 3.56 | | | |
| HCl | 0.36 | 0.1% | 36.00 | 0.01 | | | |
| Sodium bicarbonate | 0.84 | 0.1% | 84.00 | 0.01 | | | |

Is cured and pyrolized to form a black ceramic pigment.

Example 24

Using the reaction type process a precursor formulation was made using the following formulation. The temperature of the reaction was maintained at 72° C. for 21 hours.

| Reactant or Solvent | Mass | % of Total | MW | Moles of Reactant/ solvent | % of Total Moles of Silane | Moles of Si | Moles of EtOH |
|---|---|---|---|---|---|---|---|
| Phenyltriethoxysilane | 234.00 | 32.0% | 240.37 | 0.97 | 54.34% | 0.97 | 2.92 |
| Phenylmethyldiethoxysilane | 90.00 | 12.3% | 210.35 | 0.43 | 23.88% | 0.43 | 0.86 |
| Dimethyldiethoxysilane | 0.00 | 0.0% | 148.28 | — | 0.00% | — | — |
| Methyldiethoxysilane | 28.50 | 3.9% | 134.25 | 0.21 | 11.85% | 0.21 | 0.42 |
| Vinylmethyldiethoxysilane | 28.50 | 3.9% | 160.29 | 0.18 | 9.93% | 0.18 | 0.36 |
| Trimethyethoxysilane | 0.00 | 0.0% | 118.25 | — | 0.00% | — | — |
| Acetone in hydrolyzer | 0.00 | 0.0% | 58.08 | — | | | |
| Ethanol in hydrolyzer | 265.00 | 36.3% | 46.07 | 5.75 | | | |
| Water in hydrolyzer | 83.00 | 11.4% | 18.00 | 4.61 | | | |
| HCl | 0.36 | 0.0% | 36.00 | 0.01 | | | |
| Sodium bicarbonate | 0.84 | 0.1% | 84.00 | 0.01 | | | |

Is cured and pyrolized to form a black ceramic pigment.

Example 25

Using the reaction type process a precursor formulation was made using the following formulation. The temperature of the reaction was maintained at 61° C. for 21 hours.

| Reactant or Solvent | Mass | % of Total | MW | Moles of Reactant/ solvent | % of Total Moles of Silane | Moles of Si | Moles of EtOH |
|---|---|---|---|---|---|---|---|
| Phenyltriethoxysilane | 142.00 | 21.1% | 240.37 | 0.59 | 37.84% | 0.59 | 1.77 |
| Phenylmethyldiethoxysilane | 135.00 | 20.1% | 210.35 | 0.64 | 41.11% | 0.64 | 1.28 |
| Dimethyldiethoxysilane | 0.00 | 0.0% | 148.28 | — | 0.00% | — | — |
| Methyldiethoxysilane | 24.00 | 3.6% | 134.25 | 0.18 | 11.45% | 0.18 | 0.36 |
| Vinylmethyldiethoxysilane | 24.00 | 3.6% | 160.29 | 0.15 | 9.59% | 0.15 | 0.30 |
| Trimethyethoxysilane | 0.00 | 0.0% | 118.25 | — | 0.00% | — | — |
| Acetone in hydrolyzer | 278.00 | 41.3% | 58.08 | 4.79 | | | |
| Ethanol in hydrolyzer | 0.00 | 0.0% | 46.07 | — | | | |
| Water in hydrolyzer | 69.00 | 10.2% | 18.00 | 3.83 | | | |
| HCl | 0.36 | 0.1% | 36.00 | 0.01 | | | |
| Sodium bicarbonate | 0.84 | 0.1% | 84.00 | 0.01 | | | |

Is cured and pyrolized to form a black ceramic pigment.

Example 26

Using the reaction type process a precursor formulation was made using the following formulation. The temperature of the reaction was maintained at 72° C. for 21 hours.

| Reactant or Solvent | Mass | % of Total | MW | Moles of Reactant/ solvent | % of Total Moles of Silane | Moles of Si | Moles of EtOH |
|---|---|---|---|---|---|---|---|
| Methyltriethoxysilane | 0.00 | 0.0% | 178.30 | — | 0.00% | — | — |
| Phenylmethyldiethoxysilane | 0.00 | 0.0% | 210.35 | — | 0.00% | — | — |
| Dimethyldiethoxysilane | 56 | 7.2% | 148.28 | 0.38 | 17.71% | 0.38 | 0.76 |
| Methyldiethoxysilane | 182 | 23.2% | 134.25 | 1.36 | 63.57% | 1.36 | 2.71 |
| Vinylmethyldiethoxysilane | 64 | 8.2% | 160.29 | 0.40 | 18.72% | 0.40 | 0.80 |
| Triethoxysilane | 0.00 | 0.0% | 164.27 | — | 0.00% | — | — |
| Hexane in hydrolyzer | 0.00 | 0.0% | 86.18 | — | | | |
| Acetone in hydrolyzer | 0.00 | 0.0% | 58.08 | — | | | |
| Ethanol in hydrolyzer | 400.00 | 51.1% | 46.07 | 8.68 | | | |
| Water in hydrolyzer | 80.00 | 10.2% | 18.00 | 4.44 | | | |

-continued

| Reactant or Solvent | Mass | % of Total | MW | Moles of Reactant/solvent | % of Total Moles of Silane | Moles of Si | Moles of EtOH |
|---|---|---|---|---|---|---|---|
| HCl | 0.36 | 0.0% | 36.00 | 0.01 | | | |
| Sodium bicarbonate | 0.84 | 0.1% | 84.00 | 0.01 | | | |

Is cured and pyrolized to form a black ceramic pigment.

Example 27

Using the reaction type process a precursor formulation was made using the following formulation. The temperature of the reaction was maintained at 61° C. for 21 hours.

| Reactant or Solvent | Mass | % of Total | MW | Moles of Reactant/solvent | % of Total Moles of Silane | Moles of Si | Moles of EtOH |
|---|---|---|---|---|---|---|---|
| Phenyltriethoxysilane | 198.00 | 26.6% | 240.37 | 0.82 | 52.84% | 0.82 | 2.47 |
| Phenylmethyldiethoxysilane | 0.00 | 0.0% | 210.35 | — | 0.00% | — | — |
| Dimethyldiethoxysilane | 109.00 | 14.6% | 148.28 | 0.74 | 47.16% | 0.74 | 1.47 |
| Methyldiethoxysilane | 0.00 | 0.0% | 134.25 | — | 0.00% | — | — |
| Vinylmethyldiethoxysilane | 0.00 | 0.0% | 160.29 | — | 0.00% | — | — |
| Trimethyethoxysilane | 0.00 | 0.0% | 118.25 | — | 0.00% | — | — |
| Acetone in hydrolyzer | 365.00 | 49.0% | 58.08 | 6.28 | | | |
| Ethanol in hydrolyzer | 0.00 | 0.0% | 46.07 | — | | | |
| Water in hydrolyzer | 72.00 | 9.7% | 18.00 | 4.00 | | | |
| HCl | 0.36 | 0.0% | 36.00 | 0.01 | | | |
| Sodium bicarbonate | 0.84 | 0.1% | 84.00 | 0.01 | | | |

Is cured and pyrolized to form a black ceramic pigment.

Example 28

Using the reaction type process a precursor formulation was made using the following formulation. The temperature of the reaction was maintained at 72° C. for 21 hours.

| Reactant or Solvent | Mass | % of Total | MW | Moles of Reactant/solvent | % of Total Moles of Silane | Moles of Si | Moles of EtOH |
|---|---|---|---|---|---|---|---|
| Phenyltriethoxysilane | 180.00 | 22.7% | 240.37 | 0.75 | 44.10% | 0.75 | 2.25 |
| Phenylmethyldiethoxysilane | 50.00 | 6.3% | 210.35 | 0.24 | 14.00% | 0.24 | 0.48 |
| Dimethyldiethoxysilane | 40.00 | 5.0% | 148.28 | 0.27 | 15.89% | 0.27 | 0.54 |
| Methyldiethoxysilane | 30.00 | 3.8% | 134.25 | 0.22 | 13.16% | 0.22 | 0.45 |
| Vinylmethyldiethoxysilane | 35.00 | 4.4% | 160.29 | 0.22 | 12.86% | 0.22 | 0.44 |
| Trimethyethoxysilane | 0.00 | 0.0% | 118.25 | — | 0.00% | — | — |
| Hexane in hydrolyzer | 0.00 | 0.0% | 86.18 | — | | | |
| Acetone in hydrolyzer | 0.00 | 0.0% | 58.08 | — | | | |
| Ethanol in hydrolyzer | 380.00 | 48.0% | 46.07 | 8.25 | | | |
| Water in hydrolyzer | 76.00 | 9.6% | 18.00 | 4.22 | | | |
| HCl | 0.36 | 0.0% | 36.00 | 0.01 | | | |
| Sodium bicarbonate | 0.84 | 0.1% | 84.00 | 0.01 | | | |

Is cured and pyrolized to form a black ceramic pigment.

Example 29

A polysilocarb formulation has 95% MHF and 5% TV is cured and pyrolized to form a black ceramic pigment.

Example 30

A polysilocarb formulation has 90% MHF, 5% TV, and 5% VT is cured and pyrolized to form a black ceramic pigment.

Example 31

A polysilocarb formulation has 0-20% MHF, 0-30% TV, 50-100% H62 C and 0-5% a hydroxy terminated dimethyl polysiloxane is cured and pyrolized to form a black ceramic pigment.

Example 32

Mill bases using the pigment of Examples 1, 2, 8, 10 and 12 are made. The mill bases have a thermoplastic acrylic polyol resin, a solvent Methyl amyl ketone and has a pigment loading of 1.5 to 6.0 pounds per gallon. The mill bases exhibits Newtonian flow characteristics.

Example 33

Mill bases using the pigment of Examples 2-4, 5, 6, 11, and 13 are made. The mill bases have a thermoplastic acrylic polyol resin, a solvent Methyl Amyl ketone and has a pigment loading of 1.5 to 6.0 pounds/gallon. The mill bases exhibits Newtonian flow characteristics.

Example 34

Mill bases using the pigment of Examples 1, 13, 14, 16 and 23 are made. The mill bases have a thermoplastic acrylic polyol resin, a solvent methyl amyl ketone and has a pigment loading of 1.5 to 6.0 pounds per gallon. The mill bases exhibits Newtonian flow characteristics.

Example 35

A mill base using any of the pigments of Examples 1 to 31 is made. The mill base has a thermoplastic acrylic polyol resin, a solvent methyl amyl ketone and has a pigment loading of 1.5 to 6.0 pounds/gallon.

Example 36

Mill bases using the pigment of Examples 1, 2, 8, 10 and 12 are made. The mill bases have a thermoplastic acrylic emulsion, a solvent water and has a pigment loading of 1.5 to 6 pounds/gallon Example 37

Mill bases using the pigment of Examples 1, 2, 8, 10 and 12 are made. The mill bases have a low molecular weight Bisphenol A diglycidal ether resin, a solvent xylene, and has a pigment loading of 1.5 to 6.0 pounds/gallon Example 38

Mill bases using the pigment of Examples 1, 2, 8, 10 and 12 are made. The mill bases have a modified hydroxyl ethyl cellulose, surfactant, and water and has a pigment loading of 1.5 to 8.0 pounds/gallon Example 39

Mill bases using the pigment of Examples 1, 2, 8, 10 and 12 are made. The mill bases have a silicone resin, a solvent xylene and has a pigment loading of 1.5 to 5.0 pounds/gallon Example 40

Mill bases using the pigment of Examples 1, 2, 8, 10 and 12 are made. The mill bases have a mineral oil based resin, a solvent mineral spirits and has a pigment loading of 1.5 to 8 pounds/gallon.

Example 41

Mill bases using the pigment of Examples 1, 2, 8, 10 and 12 are made. The mill bases have a mineral oil based resin, a solvent mineral spirits and has a pigment loading of 2 pounds/gallon.

Example 42

Black polysilocarb derived ceramic pigment is loaded at 1 g/Kg of a thermoplastic acrylic resin having the composition of S/MMA/BA/HEA (where S is styrene, MMA is methyl methacrylate, BA is n-butyl acrylate, and HEA is 2-hydroxyethyl acrylate). The resin has a weight ratio for S:MMA:BA:HEA of 15:14:40:30.

Example 43

Black polysilocarb derived ceramic pigment is loaded at 30 g/Kg of a thermoplastic acrylic resin having the composition of S/MMA/BA/HEA (where S is styrene, MMA is methyl methacrylate, BA is n-butyl acrylate, and HEA is 2-hydroxyethyl acrylate). The resin has a weight ratio for S:MMA:BA:HEA of 15:14:40:30.

Example 44

Black polysilocarb derived ceramic pigment is loaded at 100 g/Kg of a thermoplastic acrylic resin having the composition of S/MMA/BA/HEA (where S is styrene, MMA is methyl methacrylate, BA is n-butyl acrylate, and HEA is 2-hydroxyethyl acrylate). The resin has a weight ratio for S:MMA:BA:HEA of 15:14:40:30.

Example 45

Black polysilocarb derived ceramic pigments of Example 1-6, 8 10, and 12 are loaded at 6 pounds/gallon of a water-reducible acrylic resin having the composition of MMA/BA/HEMA/AA (where HEMA is 2-hydroxyethyl methacrylate, and AA is acrylic acid). The resin has a weight ratio for MMA:BA:HEMA:AA of 60:22.2:10:7.8.

Example 46

Black polysilocarb derived ceramic pigment is loaded at 5 pounds/gallon of a water-reducible acrylic resin having the composition of MMA/BA/HEMA/AA (where HEMA is 2-hydroxyethyl methacrylate, and AA is acrylic acid). The resin has a weight ratio for MMA:BA:HEMA:AA of 60:22.2:10:7.8.

Example 47

Black polysilocarb derived ceramic pigments of Example 1-31 are loaded at 1.5 to 8 pounds/gallon of a water-reducible acrylic resin having the composition of MMA/BA/HEMA/AA (where HEMA is 2-hydroxyethyl methacrylate, and AA is acrylic acid). The resin has a weight ratio for MMA:BA:HEMA:AA of 60:22.2:10:7.8.

Example 48

A very high temperature coating (VHTC) having a silicon based resin and having polysilocarb ceramic pigment, size 0.25 µm, and a loading of 0.3 lbs/gal (23.97 g/L) has the following characteristics Good hiding power, excellent heat stability, jet black masstone, excellent UV stability and outdoor weather resistance, excellent humidity resistance, excellent corrosion resistance and hardness.

Example 49

A very high temperature coating having a silicon based resin and having polysilocarb ceramic pigment, size 0.5 µm, and a loading of 0.5 lbs/gal (59.91 g/L) has the following characteristics Good hiding power, excellent heat stability, jet black masstone, excellent UV stability and outdoor weather resistance, excellent humidity resistance, excellent corrosion resistance and hardness.

Example 50

A very high temperature coating having a silicon based resin and having polysilocarb ceramic pigment, size 0.1 µm, and a loading of 0.2 lbs/gal (11.83 g/L) has the following characteristics Good hiding power, excellent heat stability, jet black masstone, excellent UV stability and outdoor weather resistance, excellent humidity resistance, excellent corrosion resistance and hardness.

Example 51

The VHTCs of Examples 48-50 are essentially free of heavy metals, having less than about 1 ppm Mn, Cr, or other heavy metals, having less than about 0.1 ppm Mn, Cr, or other heavy metals, having less than about 0.01 ppm Mn, Cr, or other heavy metals, less than about 0.001 ppm heavy metals, and having less than 0.0001 ppm heavy metals, and still more preferably being free from any detectable heavy metals, using standard and established testing methods know to the industry. The PDC pigments used in the formulations can have less than about 100 ppm heavy metals, less than about 10 ppm heavy metals, less than about 1 ppm heavy metals and less than about 0.1 heavy metals.

Example 52

A high-solids acrylic enamel mill base having 25% solvent (butyl acetate), 20%≤2 μm polysilocarb ceramic pigment, and 55% resin. The mill base is then added to an acrylic isocyanate base at a ratio of 1:3. The acrylic enamel is sprayed onto a metal substrate and exhibits the following features Gloss 20 degrees 95%, Gloss 60 degrees 99%, Color Development L 25, a 0, b −0.5

Example 53

A polysilocarb ceramic pigment of Examples 1-31 is a colorant suitable and advantageous in multiple industrial, architectural, marine and automotive systems. The pigment is low dusting and easily disperses into acrylics, lacquers, alkyds, latex, polyurethane, phenolics, epoxies and waterborne systems providing a durable, uniform coating and pleasant aesthetic in both matte and gloss finishes. The polysilocarb ceramic pigment has low oil absorption, which among other things, permits formulations to move to higher solids loading with lower VOC content. The pigment is substantially free, and preferably entirely free from heavy metals.

Example 54

An embodiment of the polysilocarb ceramic pigment of Examples 1-31 is a colorant suitable and advantageous in multiple industrial settings and is non-conductive, acid, alkali resistant, and thermally stable up to 700° C., and 800° C. and 900° C. and 1000° C.

Example 55

An embodiment of the polysilocarb ceramic pigment of Examples 1-31, has added to the precursors a filler that provides conductivity to the pyrolized pigment, is a colorant suitable and advantageous in multiple industrial settings and is conductive, acid, alkali resistant, and thermally stable up to the melting temperature of the conductive filler.

Example 56

The polysilocarb ceramic pigment of Examples 1-6, 8, and 10-16 added at sufficient levels to obtain the required coverage by the appliance manufacturer and applied to the interior of a microwave oven. The interior polysilocarb pigment coating has good gloss, hiding and is non-arching during microwave use.

Example 57

A polysilocarb ceramic pigment has added to the precursor formulations carbon black. The pyrolized filled polysilocarb pigment has the superior wettability and dispersion performance of the net polysilocarb pigments, while having the cheaper carbon black material. The carbon black filler is a cheaper extender for the polysilocarb material.

Example 57a

The pigments of Example 57 have 20% carbon black filler.

Example 57b

The pigments of Example 57 have 30% carbon black filler.

Example 57c

The pigments of Example 57 have 40% carbon black filler.

Example 57d

The pigments of Example 57 have 50% carbon black filler.

Example 57e

The pigments of Example 57 have 60% carbon black filler.

Example 58

A polysilocarb formulation is cured to into the volumetric shape of a bead. The end cured polysilocarb derived beads are, for example, added to paints, glues, plastics, and building materials, such as dry wall, sheet rock, gypsum board, MDF board, plywood, plastics and particleboard. The end cured polysilocarb derived beads, as additives, can provide, among other things, binding (e.g., serve as a binder), water resistivity, fire resistance, fire retardation, fire protection and strength; as well as, abrasion resistance, wear resistance, corrosion resistance and UV resistance, if located at or near the surface of the shape.

Example 58a

In addition to a beads of Example 58, the polysilocarb additives can be in the form of a fine powder, fines, a power or other dispersible forms. The dispersible form can be obtained by grinding or crushing larger cured structures. They also may be obtained through the curing process if done under conditions that cause the structure to fracture, crack or break during curing. These dispersible forms may also be obtained by other processing techniques, for example, spray curing or drying.

Example 59

A polysilocarb formulation is cured to into the volumetric shape of a bead. The beads are then pyrolized to for a polysilocarb derived ceramic bead. The polysilocarb derived ceramic beads are added, for example, to paints, glues, plastics, and building materials, such as dry wall, sheet rock, gypsum board, MDF board, plywood, plastics and particleboard. The ceramic polysilocarb beads, as additives, can provide, among other things, fire resistance, fire retardation, fire protection and strength.

In addition to a bead the polysilocarb additives can be in the form of a fine power, fines, a power or other dispersible forms. The dispersible form can be obtained by grinding or crushing larger cured or pyrolized structures. They also may be obtained through the curing or pyrolysis process if done under conditions that cause the structure to fracture, crack or break during curing or pyrolysis.

Example 60

A polysilocarb formulation is pyrolized in the form of a volumetric structure. The ceramic polysilocarb derived volumetric structure exhibits reflective and refractive optical properties, such as opalescence, shine, twinkle, and sparkle. These optical properties are present when the structure is black in color, (e.g., no colorant has been added to the formulation); or if the structure is colored (e.g., any color other than black, e.g., white, yellow, red, etc.).

Example 61

The volumetric structure of Example 60 is a work surface, such as a table top, a bench top, an insert, or a kitchen counter top, to name a few.

Example 62

The volumetric structure of Example 61 has other colorings or additive to provide simulated granite like appearance.

Example 63

The volumetric structures of Example 60 are small beads that are black and exhibit a twinkle, opalescence or shin. These beads are incorporated into a paint formulation. The patent formulation is for example applied to automobiles or appliances. It provides a flat or matte finish, which is for example popular on newer BMWs and Mercedes, but adds to that matte finish an inner sparkle or luster. Thus, the polysiloxane based paint formulation provides a sparkle matte finish to an automobile, appliance or other article.

Example 64

Pyrolized polysilocarb beads having a size of from about 100 to about 1,000 microns are added to a paint formulation at a loading of from about 1% to about 40%.

Example 65

The paint of Example 64 in which the paint formulation, is an automotive paint, and is colored blue and the beads are the same blue color as the paint, and have size of 350 microns (+/−5%) and a loading of about 25%.

Example 66

The paint of Example 64 in which the beads are not colored, i.e., they are black, and have a size ranging from about 300-500 microns, and the paint is a black, although not necessarily the same black as the beads.

Example 67

A latex paint formulation having pyrolized polysilocarb power added into the formulation, the power has a size range of about 0.5-100 microns, and the powder has a loading of about 15%.

Example 68

The paint formulation of Example 66 is an enamel.

Example 69

The polysilocarb ceramic pigments can be made from the pyrolysis of any polysilocarb batches that are capable of being pyrolized. The polysilocarb pigment material can be provided, for example, as beads, powder, flakes, fines, or other forms that are capable of being dispersed or suspended in the paint formulation (e.g., platelets, spheres, crescents, angular, blocky, irregular or amorphous shapes). Beads can have a size of from about 100 to about 1,000 microns in diameter. Powders can have a particle size range of from about 0.5 to about 100 microns in diameter. Any subset range within these ranges can create the desired effect or color. Larger and smaller sizes may also provide the desired effects in other formulations. For example: 300-500 micron range beads; 350 (+/−5%) micron beads; 5-15 micron range powder. Particle size ranges for a particular polysilocarb ceramic pigment preferably range as tight as +/−10% and more preferably +/−5%. The range may also be broader in certain applications, e.g., 100-1000 for beads, and e.g., 0.5-100 for powders. The density and hardness of the polysilocarb ceramic pigment can be varied, controlled and predetermined by the precursor formulations used, as well as the curing and pyrolyzing conditions. The polysilocarb ceramic pigments can provided enhanced corrosion resistance, scratch resistance and color (UV) stability to paint formulations. Optical properties or effects of the polysilocarb ceramic pigment can, among other ways, be controlled by the use of different gases and gas mixtures, as well as other curing and pyrolysis conditions. The polysilocarb ceramic pigment loading can be used anywhere from a 1% to a 40% in order to achieve the desired effect. Further, the use of the polysilocarb ceramic pigments can provide enhanced flame retardant benefits. The polysilocarb ceramic pigments have a further advantage of being low dusting, and easily mixed into any type of paint formulations, e.g., latex, enamel, polyurethanes, automotive OEM and refinish, alkyd, waterborne, acrylic and polyol coatings formulations. The polysilocarb ceramic pigments can also be used as a fine colorant in inks and graphic arts formulations.

Example 70a

A ceramic ink comprising 10-30% polysilocarb black ceramic pigment, 10-60% zinc or bismuth submicron glass frit, 10-20% Sucrose acetate isobutyrate, 4-15% hydrocarbon resin, 5-15% ethylene glycol.

Example 70b

A packaging ink comprising 2-30% polysilocarb black ceramic pigment, 5-15% nitrocellulose resin, 25-35% ethanol solvent, 10-20% ethyl acetate solvent, 1-2% citrate plasticizer, 1% polyethylene wax solution, 5-10% additives.

Example 71a

A plastic comprising of 75-80% Polypropylene copolymer, 1-6% polysilocarb black ceramic pigment, 15-20% talc

Example 71b

A plastic comprising of 94-98% HDPE plastic and 2-6% polysilocarb black ceramic pigment

Example 71c

A plastic comprising 94-98% polycarbonate and 2-6% polysilocarb black ceramic pigment

Example 71d

A plastic comprising 94-99% polyamide and 1-6% polysilocarb black pigment

Example 71e

A rubber comprising of 55-65% EPDM elastomer, 10-40% polysilocarb black ceramic pigment, 5-10% paraffinic extender oil, 3% zinc oxide, 0.5% stearic acid, 0.9% sulfur, 0.9% tetramethyl thiuram monosulphide, 0.5% antioxidant, 0.3% mercaptobenzothiazole.

Example 71f

A rubber based on 60-70% Fluoroelastomer, 10-20% polysilocarb black ceramic pigment, 1-2% dimethyl-di(t-butyl peroxy)hexane, 1-1.5% triallyl iscocyanurate, 1-1.5% Zinc oxide.

Example 71g

A plastic comprising 75-80% ABS plastic, 2-6% polysilocarb black ceramic pigment, 15-20% talc.

Example 71h

A phenolic molding compound comprising 50% phenolic resin, 35-45% talc, 5-15% polysilocarb black ceramic pigment.

Example 71i

A Thermoplastic olefin compound comprising 60% polypropylene copolymer, 10-15% polyolefin elastomer, 2-6% polysilocarb black ceramic pigment, 10% talc, 0.2% antioxidant.

Example 71j

A siloxane compound comprising 75-95% siloxane, 1-18% fumed silica, and 1-5% polysilocarb black ceramic pigment.

Example 71k

A siloxane compound comprising 50-80% siloxane, 1-20% fumed silica, 1-20% talc or other white filler, and 0.5-5% polysilocarb black pigment.

Example 72

A lawnmower piston assembly made from A phenolic molding compound comprising 50% phenolic resin, 35-45% talc, 5-15% polysilocarb black ceramic pigment.

Example 73

A car dashboard made from a plastic comprising of 75-80% Polypropylene copolymer, 1-6% polysilocarb black ceramic pigment, 15-20% talc.

Example 74

A car bumper made from a thermoplastic olefin compound having 60% polypropylene copolymer, 10-15% polyolefin elastomer, 2-6% polysilocarb black ceramic pigment, 10% talc, 0.2% antioxidant

Example 75

A high temperature stable pump housing coating having 30-35% silicone resin, 8-30% micronized mica filler, 1-15% polysilocarb black ceramic pigment, 35-50% xylene solvent.

Example 76

An adhesive comprising 7-10% chlorinated rubber, 5-7% polysilocarb ceramic black pigment, 4-5% phenol formaldehyde resin, 1-2% fumed silica, 1-2% zinc oxide, 50-6-% methyl ethyl ketone solvent, 5-10% xylene solvent.

The primary focus of the specification is on black pigment and additives. It should be understood, however, that other colors of polymer derived ceramic pigments and preferably polysilocarb derived ceramic pigments can be utilized. These embodiments can have colorants, or fillers that impart different colors to the ceramic pigment. Such colorants can be for example glazes or other fillers or additives that maintain their color properties under pyrolysis conditions.

It is noted that there is no requirement to provide or address the theory underlying the novel and groundbreaking processes, materials, performance or other beneficial features and properties that are the subject of, or associated with, embodiments of the present inventions. Nevertheless, various theories are provided in this specification to further advance the art in this area. These theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the function-features of embodiments of the methods, articles, materials, devices and system of the present inventions; and such later developed theories shall not limit the scope of protection afforded the present inventions.

The various embodiments of formulations, batches, materials, compositions, devices, systems, apparatus, operations activities and methods set forth in this specification may be used in the various fields where pigments and additives find applicability, as well as, in other fields, where pigments, additives and both, have been unable to perform in a viable manner (either cost, performance or both). Additionally, these various embodiments set forth in this specification may be used with each other in different and various combinations. Thus, for example, the configurations provided in the various embodiments of this specification may be used with each other; and the scope of protection afforded the present inventions should not be limited to a particular embodiment, configuration or arrangement that is set forth in a particular embodiment, example, or in an embodiment in a particular Figure.

The invention may be embodied in other forms than those specifically disclosed herein without departing from its spirit or essential characteristics. The described embodiments are to be considered in all respects only as illustrative and not restrictive.

What is claimed:

1. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein 20 weight % to 80 weight % of the carbon is free carbon.

2. The coating formulation of claim 1, wherein the formulation is selected from the group consisting of paint, powder coat, adhesive, nail polish, and ink.

3. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein 20 weight % to 80 weight % of the carbon is silicon-bound-carbon.

4. The coating formulation of claim 3, wherein the formulation is selected from the group consisting of paint, powder coat, adhesive, nail polish, and ink.

5. The coating formulation of claim 3, wherein the black polymer derived ceramic material has a particle size of less than about 1.5 µm.

6. The coating formulation of claim 3, wherein the black polymer derived ceramic material has a particle size $D_{50}$ of from about 1 µm to about 0.1 µm.

7. The coating formulation of claim 3, wherein the coating defines a blackness selected from the group consisting of: PMS 433, Black 3, Black 3, Black 4, Black 5, Black 6, Black 7, Black 2 2x, Black 3 2x, Black 4 2x, Black 5 2x, Black 6 2x, and Black 7 2x.

8. The coating formulation of claim 3, wherein the coating defines a blackness selected from the group consisting of: Tri-stimulus Colorimeter of X from about 0.05 to about 3.0, Y from about 0.05 to about 3.0, and Z from about 0.05 to about 3.0; a CIE L a b of L of less than about 40; a CIE L a b of L of less about 20; a CIE L a b of L of less than 50, b of less than 1.0 and a of less than 2; and a jetness value of at least about 200 $M_y$.

9. The coating formulation of claim 3, wherein the formulation is essentially free of heavy metals.

10. The coating formulation of claim 3, wherein the formulation has less than about 10 ppm of heavy metals.

11. A paint formulation comprising: a resin, a solvent, and a polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

12. The paint formulation of claim 11, wherein the polymer derived ceramic pigment has a primary particle $D_{50}$ size of from about 0.1 µm to about 2.0 µm.

13. The paint formulation of claim 12, wherein the polymer derived ceramic pigment is loaded at from about 1.5 pounds/gallon to about 10 pounds/gallon.

14. The paint formulation of claim 12, wherein the resin is selected from the group of resins consisting of thermoplastic acrylic polyols, Bisphenol A diglycidal ether, silicone, oil based, and water-reducible acrylic.

15. The paint formulation of claim 11, wherein the formulation has less than about 0.01 ppm of heavy metals.

16. The paint formulation of claim 12, wherein the formulation has less than about 0.1 ppm of heavy metals.

17. The paint formulation of claim 11, wherein the formulation has less than about 1 ppm of heavy metals, and the paint formulation is a very high temperature coating, wherein the paint formulation is thermally stable to greater than 700° C.

18. The paint formulation of claim 12, wherein the formulation has less than about 10 ppm of heavy metals, and the paint formulation is a very high temperature coating.

19. The paint formulation of claim 11, wherein the paint formulation is a very high temperature coating, and wherein the paint formulation is thermally stable to greater than 1000° C.

20. An ink formulation comprising: a first material and a black polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

21. A nail polish formulation, comprising a carrier material and a black polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

22. A plastic material, comprising a first material and a second material, wherein the first material is a plastic and makes up at least 50% of the total weight of the plastic material, and the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

23. The plastic material of claim 22, wherein the plastic is selected from the group consisting of HDPE, LDPE, PP, Acrylic, Epoxy, Linseed Oil, PU, PUR, EPDM, SBR, PVC, water based acrylic emulsions, ABS, SAN, SEBS, SBS, PVDF, PVDC, PMMA, PES, PET, NBR, PTFE, siloxanes, polyisoprene and natural rubbers.

24. The plastic material of claim 22, wherein the plastic is selected from the group consisting of thermosetting, thermoforming, thermoplastic, orientable, biaxially orientable, polyolefins, polyamide, engineering plastics, textile adhesives coatings (TAC) and plastic foams.

25. The plastic material of claim 22, wherein the plastic is selected from the group consisting of styrenic alloys, acrylonitrile butadiene styrene (ABS), polyurethanes, polystyrenes, acrylics, polycarbonates (PC), epoxies, polyesters, nylon, polyethylene, high density polyethylene (HDPE), very low density polyethylene (VLDPE).

26. The plastic material of claim 22, wherein the plastic is selected from the group consisting of low density polyethylene (LDPE), polypropylene (PP), polyvinyl chloride (PVC), polyethylene terephthalate (PET), polybutylene terephthalate (PBT), poly ether ethyl ketone (PEEK), polyether sulfone (PES), bis maleimide, and viscose (cellulose acetate).

27. A paint comprising: a resin and a polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

28. An ink comprising: a carrier material and a black polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

29. An adhesive comprising: a carrier material and a black polymer derived ceramic pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

30. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating is a paint.

31. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating is a powder coat.

32. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material has a particle size of less than about 1.5 µm.

33. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating defines a blackness selected from the group consisting of: PMS 433, Black 3, Black 3, Black 4, Black 5, Black 6, Black 7, Black 2 2x, Black 3 2x, Black 4 2x, Black 5 2x, Black 6 2x, and Black 7 2x.

34. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating defines a blackness selected from the group consisting of: Tri-stimulus Colorimeter of X from about 0.05 to about 3.0, Y from about 0.05 to about 3.0, and Z from about 0.05 to about 3.0; a CIE L a b of L of less than about 40; a CIE L a b of L of less about 20; a CIE L a b of L of less than 50, b of less than 1.0 and a of less than 2; and a jetness value of at least about 200 $M_y$.

35. The coating of claim 30, wherein the paint is a paint selected from the group consisting of oil, acrylic, latex, enamel, varnish, water reducible, alkyd, epoxy, polyester-epoxy, acrylic-epoxy, polyimide-epoxy, urethane-modified alkyd, and acrylic-urethane.

36. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating is essentially free of heavy metals.

37. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating has less than about 10 ppm of heavy metals.

38. A paint comprising a resin and a polymer derived pigment comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon.

39. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the first material comprises a material selected from the group of materials consisting of acrylics, lacquers, alkyds, latex, polyurethane, phenolics, epoxies and waterborne.

40. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the coating is a paint selected from the group consisting of oil, acrylic, latex, enamel, varnish, water reducible, alkyd, epoxy, polyester-epoxy, acrylic-epoxy, polyamide-epoxy, urethane-modified alkyd, and acrylic-urethane.

41. A coating comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight; and, wherein the black polymer derived ceramic material comprises about 40 weight % to about 50 weight % silicon, and wherein about 25 weight % to about 40 weight % of the carbon is silicon-bound-carbon.

42. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon, and wherein the first material weight percent is larger than the second material weight percent; and, wherein the black polymer derived ceramic material comprises about 40 weight % to about 50 weight % silicon, and wherein about 55 weight % to about 75 weight % of the carbon is free carbon.

43. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein the black polymer derived ceramic material comprises about 20 weight % to about 30 weight % oxygen, and wherein about 25 weight % to about 40 weight % of the carbon is silicon-bound-carbon.

44. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein the black polymer derived ceramic material comprises about 20 weight % to about 30 weight % oxygen, and wherein about 55 weight % to about 75 weight % of the carbon is free carbon.

45. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein the black polymer derived ceramic material comprises about 20 weight % to about 30 weight % carbon, and wherein about 25 weight % to about 40 weight % of the carbon is silicon-bound-carbon.

46. A coating formulation comprising: a first material and a second material; wherein the first material defines a first material weight percent of the coating formulation and the second material defines a second material weight percent of the coating formulation; wherein the second material is a black polymer derived ceramic material comprising from about 30 weight % to about 60 weight % silicon, from about 5 weight % to about 40 weight % oxygen, and from about 3 weight % to about 35 weight % carbon; and wherein the first material weight percent is larger than the second material weight percent; and, wherein the black polymer derived ceramic material comprises about 20 weight % to about 30 weight % carbon, and wherein about 55 weight % to about 75 weight % of the carbon is free carbon.

47. A coating comprising: a first material and a second material; wherein the first material defines a first material weight percent of the coating formulation and the second material comprises a second material weight percent of the coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon; and wherein 20 weight % to 80 weight % of the carbon is silicon-bound-carbon, and the first material weight percent is larger than the second material weight percent; and, wherein the black polymer derived ceramic material comprises about 40 weight % to about 50 weight % silicon, and wherein about 25 weight % to about 40 weight % of the carbon is silicon-bound-carbon.

48. A coating comprising: a first material and a second material; wherein the first material defines a first material weight percent of the coating formulation and the second material comprises a second material weight percent of the coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material comprises about 40 weight % to about 50 weight % silicon, and wherein about 55 weight % to about 75 weight % of the carbon is free carbon.

49. A coating comprising: a first material and a second material; wherein the first material defines a first material weight percent of the coating formulation and the second material comprises a second material weight percent of the coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material comprises about 20 weight % to about 30 weight % oxygen, and wherein about 25 weight % to about 40 weight % of the carbon is silicon-bound-carbon.

50. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material comprises about 20 weight % to about 30 weight % oxygen, and wherein about 55 weight % to about 75 weight % of the carbon is free carbon.

51. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material comprises about 20 weight % to about 30 weight % carbon, and wherein about 25 weight % to about 40 weight % of the carbon is silicon-bound-carbon.

52. A coating comprising: a first material and a second material; wherein the first material defines a first material weight percent of the coating formulation and the second material comprises a second material weight percent of the total coating formulation; and wherein the second material is a black polymer derived ceramic material comprising from about 30 weight % to about 60 weight % silicon, from about 5 weight % to about 40 weight % oxygen, and from about 3 weight % to about 35 weight % carbon, and wherein 20 weight % to 80 weight % of the carbon is silicon-bound-carbon, and the first material weight percent is larger than the second material weight percent; and, wherein the black polymer derived ceramic material comprises about 20 weight % to about 30 weight % carbon, and wherein about 55 weight % to about 75 weight % of the carbon is free carbon.

* * * * *